(12) United States Patent
Wang et al.

(10) Patent No.: US 12,324,647 B2
(45) Date of Patent: Jun. 10, 2025

(54) METHOD, APPARATUS, AND SYSTEM FOR ENHANCED WIRELESS MONITORING OF VITAL SIGNS

(71) Applicants: Beibei Wang, Clarksville, MD (US); Sakila Sandeepani Jayaweera Samaranayake Arachchige Dona, College Park, MD (US); Xiaolu Zeng, Beijing (CN); Wei-Hsiang Wang, College Park, MD (US); K. J. Ray Liu, Potomac, MD (US); Oscar Chi-Lim Au, Greenbelt, MD (US)

(72) Inventors: Beibei Wang, Clarksville, MD (US); Sakila Sandeepani Jayaweera Samaranayake Arachchige Dona, College Park, MD (US); Xiaolu Zeng, Beijing (CN); Wei-Hsiang Wang, College Park, MD (US); K. J. Ray Liu, Potomac, MD (US); Oscar Chi-Lim Au, Greenbelt, MD (US)

(73) Assignee: ORIGIN RESEARCH WIRELESS, INC., Rockville, MD (US)

( * ) Notice: Subject to any disclaimer, the term of this patent is extended or adjusted under 35 U.S.C. 154(b) by 0 days.

(21) Appl. No.: 17/960,080

(22) Filed: Oct. 4, 2022

(65) Prior Publication Data
US 2023/0021342 A1    Jan. 26, 2023

Related U.S. Application Data

(63) Continuation-in-part of application No. 16/790,610, filed on Feb. 13, 2020, and a continuation-in-part of
(Continued)

(51) Int. Cl.
*A61B 5/00* (2006.01)
*H04B 17/309* (2015.01)

(52) U.S. Cl.
CPC ......... *A61B 5/0002* (2013.01); *H04B 17/309* (2015.01)

(58) Field of Classification Search
CPC ........ G01S 13/003; G01S 7/006; G01S 7/415; G01S 13/343; G01S 13/42; G01S 13/50;
(Continued)

(56) References Cited

U.S. PATENT DOCUMENTS

2006/0077306 A1* 4/2006 Suyambukesan ...... H04N 5/144
348/E5.064
2020/0200887 A1* 6/2020 Hubbert .................. G01S 13/20

FOREIGN PATENT DOCUMENTS

CN     109684941     *  4/2019     ......... G06F 18/2148

OTHER PUBLICATIONS

Liu et al., "Tracking Vital Signs During Sleep Leveraging Off-the-shelf WiFi", 2015, MobiHoc'15, pp. 267-276 (Year: 2015).*
(Continued)

*Primary Examiner* — Zhiyu Lu

(57) ABSTRACT

Methods, apparatus and systems for enhanced wireless monitoring of vital signs are described. In one example, a described system comprises: a transmitter configured to transmit a wireless signal through a wireless channel of a venue; a receiver configured to receive the wireless signal through the wireless channel; and a processor. The received wireless signal differs from the transmitted wireless signal due to the wireless channel that is impacted by a periodic motion of a vital sign of an object in the venue. The processor is configured for: obtaining a time series of channel information (CI) of the wireless channel based on the received wireless signal, computing a two dimensional (2D) decomposition of the time series of CI (TSCI), enhanc-
(Continued)

ing the 2D decomposition, and monitoring the periodic motion of the vital sign based on the enhanced 2D decomposition.

20 Claims, 7 Drawing Sheets

Related U.S. Application Data application No. 16/871,000, filed on May 10, 2020, now Pat. No. 11,500,056, and a continuation-in-part of application No. 16/871,004, filed on May 10, 2020, and a continuation-in-part of application No. 16/909,913, filed on Jun. 23, 2020, and a continuation-in-part of application No. 17/019,270, filed on Sep. 13, 2020, and a continuation-in-part of application No. 17/113,023, filed on Dec. 5, 2020, and a continuation-in-part of application No. 17/149,625, filed on Jan. 14, 2021, and a continuation-in-part of application No. 17/149,667, filed on Jan. 14, 2021, and a continuation-in-part of application No. 17/180,763, filed on Feb. 20, 2021, which is a continuation-in-part of application No. 16/798,343, filed on Feb. 22, 2020, now Pat. No. 11,340,345, which is a continuation-in-part of application No. 16/798,337, filed on Feb. 22, 2020, now Pat. No. 10,845,463, application No. 17/960,080 is a continuation-in-part of application No. 17/180,762, filed on Feb. 20, 2021, now Pat. No. 11,531,087, and a continuation-in-part of application No. 17/180,766, filed on Feb. 20, 2021, and a continuation-in-part of application No. 17/214,841, filed on Mar. 27, 2021, now Pat. No. 11,500,058, and a continuation-in-part of application No. 17/214,836, filed on Mar. 27, 2021, now Pat. No. 11,500,057, and a continuation-in-part of application No. 17/352,185, filed on Jun. 18, 2021, and a continuation-in-part of application No. 17/352,306, filed on Jun. 20, 2021, and a continuation-in-part of application No. 17/537,432, filed on Nov. 29, 2021, and a continuation-in-part of application No. 17/539,058, filed on Nov. 30, 2021, and a continuation-in-part of application No. 17/540,156, filed on Dec. 1, 2021, and a continuation-in-part of application No. 17/827,902, filed on May 30, 2022, which is a continuation-in-part of application No. 17/492,598, filed on Oct. 2, 2021, now Pat. No. 11,448,728, application No. 17/960,080 is a continuation-in-part of application No. 17/492,642, filed on Oct. 3, 2021, and a continuation-in-part of application No. 17/838,228, filed on Jun. 12, 2022, and a continuation-in-part of application No. 17/838,231, filed on Jun. 12, 2022, and a continuation-in-part of application No. 17/838,244, filed on Jun. 12, 2022, and a continuation-in-part of application No. 17/888,429, filed on Aug. 15, 2022, and a continuation-in-part of application No. 17/891,037, filed on Aug. 18, 2022, and a continuation-in-part of application No. 17/945,995, filed on Sep. 15, 2022.

(60) Provisional application No. 63/253,083, filed on Oct. 6, 2021, provisional application No. 63/276,652, filed on Nov. 7, 2021, provisional application No. 63/281,043, filed on Nov. 18, 2021, provisional application No. 63/293,065, filed on Dec. 22, 2021, provisional application No. 63/308,927, filed on Feb. 10, 2022, provisional application No. 63/332,658, filed on Apr. 19, 2022, provisional application No. 63/349,082, filed on Jun. 4, 2022, provisional application No. 63/300,042, filed on Jan. 16, 2022, provisional application No. 63/354,184, filed on Jun. 21, 2022, provisional application No. 63/388,625, filed on Jul. 12, 2022.

(58) Field of Classification Search
CPC ....... G01S 13/56; H04W 48/08; H04W 48/16; H04W 56/001; H04W 84/18; H04W 4/027; H04W 4/029; B60R 2325/101; B60R 2325/106; B60R 25/31; A61B 2503/22; A61B 5/0002; A61B 5/002; A61B 5/0507; A61B 5/0816; A61B 5/7235; A61B 5/7253; H04B 17/17; H04B 17/309; G06F 21/32; G06F 21/552; G06F 2218/04; G06F 2218/10; G06F 2218/12; G06F 2221/2111
See application file for complete search history.

(56) References Cited

OTHER PUBLICATIONS

Xu et al., "Attention-based Walking Gait and Direction Recognition in Wi-Fi Networks", Jan. 2019, arXiv (Year: 2019).*

* cited by examiner

METHOD, APPARATUS, AND SYSTEM FOR ENHANCED WIRELESS MONITORING OF VITAL SIGNS

CROSS-REFERENCE TO RELATED APPLICATIONS

The present application is related to U.S. patent application with docket number OWI-0052US18, entitled "METHOD, APPARATUS, AND SYSTEM FOR VOICE ACTIVITY DETECTION BASED ON RADIO SIGNALS," filed on Oct. 4, 2022, which is expressly incorporated by reference herein in its entirety.

The present application hereby incorporates by reference the entirety of the disclosures of, and claims priority to, each of the following cases:

(a) U.S. patent application Ser. No. 16/790,610, entitled "METHOD, APPARATUS, AND SYSTEM FOR WIRELESS GAIT RECOGNITION", filed Feb. 13, 2020, (b) U.S. patent application Ser. No. 16/871,000, entitled "METHOD, APPARATUS, AND SYSTEM FOR WIRELESS TRACKING WITH GRAPH-BASED PARTICLE FILTERING", filed on May 10, 2020, (c) U.S. patent application Ser. No. 16/871,004, entitled "METHOD, APPARATUS, AND SYSTEM FOR PEOPLE COUNTING AND RECOGNITION BASED ON RHYTHMIC MOTION MONITORING", filed on May 10, 2020, (d) U.S. patent application Ser. No. 16/909,913, entitled "METHOD, APPARATUS, AND SYSTEM FOR IMPROVING TOPOLOGY OF WIRELESS SENSING SYSTEMS", filed on Jun. 23, 2020, (e) U.S. patent application Ser. No. 17/019,270, entitled "METHOD, APPARATUS, AND SYSTEM FOR VEHICLE WIRELESS MONITORING", filed on Sep. 13, 2020, (f) U.S. patent application Ser. No. 17/113,023, entitled "METHOD, APPARATUS, AND SYSTEM FOR ACCURATE WIRELESS MONITORING", filed on Dec. 5, 2020, (g) U.S. patent application Ser. No. 17/492,642, entitled "METHOD, APPARATUS, AND SYSTEM FOR MOVEMENT TRACKING", filed on Oct. 3, 2021, (h) U.S. patent application Ser. No. 17/149,625, entitled "METHOD, APPARATUS, AND SYSTEM FOR WIRELESS MONITORING WITH MOTION LOCALIZATION", filed on Jan. 14, 2021, (i) U.S. patent application Ser. No. 17/149,667, entitled "METHOD, APPARATUS, AND SYSTEM FOR WIRELESS MONITORING WITH FLEXIBLE POWER SUPPLY", filed on Jan. 14, 2021, (j) U.S. patent application Ser. No. 17/180,763, entitled "METHOD, APPARATUS, AND SYSTEM FOR WIRELESS WRITING TRACKING", filed on Feb. 20, 2021,
  (1) which is a Continuation-in-Part of U.S. patent application Ser. No. 16/798,343, entitled "METHOD, APPARATUS, AND SYSTEM FOR WIRELESS OBJECT TRACKING", filed on Feb. 22, 2020, issued as U.S. Pat. No. 11,340,345 on May 24, 2022,
    a. which is a Continuation-in-Part of U.S. patent application Ser. No. 16/798,337, entitled "METHOD, APPARATUS, AND SYSTEM FOR WIRELESS OBJECT SCANNING", filed Feb. 22, 2020, issued as U.S. Pat. No. 10,845,463 on Nov. 24, 2020, (k) U.S. patent application Ser. No. 17/180,762, entitled "METHOD, APPARATUS, AND SYSTEM FOR FALL-DOWN DETECTION BASED ON A WIRELESS SIGNAL", filed on Feb. 20, 2021, (l) U.S. patent application Ser. No. 17/180,766, entitled "METHOD, APPARATUS, AND SYSTEM FOR WIRELESS MOTION RECOGNITION", filed on Feb. 20, 2021, (m) U.S. patent application Ser. No. 17/214,841, entitled "METHOD, APPARATUS, AND SYSTEM FOR WIRELESS PROXIMITY SENSING", filed on Mar. 27, 2021, (n) U.S. patent application Ser. No. 17/214,836, entitled "METHOD, APPARATUS, AND SYSTEM FOR WIRELESSLY TRACKING KEYSTROKES", filed on Mar. 27, 2021, (o) U.S. patent application Ser. No. 17/352,185, entitled "METHOD, APPARATUS, AND SYSTEM FOR WIRELESS MICRO MOTION MONITORING", filed on Jun. 18, 2021, (p) U.S. patent application Ser. No. 17/352,306, entitled "METHOD, APPARATUS, AND SYSTEM FOR WIRELESS MONITORING TO ENSURE SECURITY", filed on Jun. 20, 2021, (q) U.S. Provisional Patent application 63/253,083, entitled "METHOD, APPARATUS, AND SYSTEM FOR WIRELESS SENSING, DETECTION AND TRACKING", filed on Oct. 6, 2021, (r) U.S. Provisional Patent application 63/276,652, entitled "METHOD, APPARATUS, AND SYSTEM FOR WIRELESSLY MONITORING VITAL SIGN AND PERIODIC MOTIONS", filed on Nov. 7, 2021, (s) U.S. Provisional Patent application 63/281,043, entitled "METHOD, APPARATUS, AND SYSTEM FOR SENSING", filed on Nov. 18, 2021, (t) U.S. patent application Ser. No. 17/537,432, entitled "METHOD, APPARATUS, AND SYSTEM FOR AUTOMATIC AND ADAPTIVE WIRELESS MONITORING AND TRACKING", filed on Nov. 29, 2021, (u) U.S. patent application Ser. No. 17/539,058, entitled "METHOD, APPARATUS, AND SYSTEM FOR HUMAN IDENTIFICATION BASED ON HUMAN RADIO BIOMETRIC INFORMATION", filed on Nov. 30, 2021, (v) U.S. patent application Ser. No. 17/540,156, entitled "METHOD, APPARATUS, AND SYSTEM FOR POSITIONING AND POWERING A WIRELESS MONITORING SYSTEM", filed on Dec. 1, 2021, (w) U.S. Provisional Patent application 63/293,065, entitled "METHOD, APPARATUS, AND SYSTEM FOR SPEECH ENHANCEMENT AND SEPARATION", filed on Dec. 22, 2021, (x) U.S. Provisional Patent application 63/300,042, entitled "METHOD, APPARATUS, AND SYSTEM FOR WIRELESS SENSING AND SLEEP TRACKING", filed on Jan. 16, 2022, (y) U.S. Provisional Patent application 63/308,927, entitled "METHOD, APPARATUS, AND SYSTEM FOR WIRELESS SENSING BASED ON MULTIPLE GROUPS OF WIRELESS DEVICES", filed on Feb. 10, 2022, (z) U.S. Provisional Patent application 63/332,658, entitled "METHOD, APPARATUS, AND SYSTEM FOR WIRELESS SENSING", filed on Apr. 19, 2022, (aa) U.S. patent application Ser. No. 17/827,902, entitled "METHOD, APPARATUS, AND SYSTEM FOR SPEECH ENHANCEMENT AND SEPARATION BASED ON AUDIO AND RADIO SIGNALS", filed on May 30, 2022,
  (1) which is a Continuation-in-Part of U.S. patent application Ser. No. 17/492,598, entitled "METHOD, APPARATUS, AND SYSTEM FOR SOUND SENSING BASED ON WIRELESS SIGNALS", filed Oct. 2, 2021, issued as U.S. Pat. No. 11,448,728 on Sep. 20, 2022,
(bb) U.S. Provisional Patent application 63/349,082, entitled "METHOD, APPARATUS, AND SYSTEM FOR WIRELESS SENSING VOICE ACTIVITY DETECTION", filed on Jun. 4, 2022,
(cc) U.S. patent application Ser. No. 17/838,228, entitled "METHOD, APPARATUS, AND SYSTEM FOR WIRELESS SENSING BASED ON CHANNEL INFORMATION", filed on Jun. 12, 2022,
(dd) U.S. patent application Ser. No. 17/838,231, entitled "METHOD, APPARATUS, AND SYSTEM FOR IDENTIFYING AND QUALIFYING DEVICES FOR WIRELESS SENSING", filed on Jun. 12, 2022,
(ee) U.S. patent application Ser. No. 17/838,244, entitled "METHOD, APPARATUS, AND SYSTEM FOR WIRELESS SENSING BASED ON LINKWISE MOTION STATISTICS", filed on Jun. 12, 2022,
(ff) U.S. Provisional Patent application 63/354,184, entitled "METHOD, APPARATUS, AND SYSTEM FOR MOTION LOCALIZATION AND OUTLIER REMOVAL", filed on Jun. 21, 2022,
(gg) U.S. Provisional Patent application 63/388,625, entitled "METHOD, APPARATUS, AND SYSTEM FOR WIRELESS SENSING AND INDOOR LOCALIZATION", filed on Jul. 12, 2022,
(hh) U.S. patent application Ser. No. 17/888,429, entitled "METHOD, APPARATUS, AND SYSTEM FOR RADIO BASED SLEEP TRACKING", filed on Aug. 15, 2022,
(ii) U.S. patent application Ser. No. 17/891,037, entitled "METHOD, APPARATUS, AND SYSTEM FOR MAP RECONSTRUCTION BASED ON WIRELESS TRACKING", filed on Aug. 18, 2022.
(jj) U.S. patent application Ser. No. 17/945,995, entitled "METHOD, APPARATUS, AND SYSTEM FOR WIRELESS VITAL MONITORING USING HIGH FREQUENCY SIGNALS", filed on Sep. 15, 2022.

TECHNICAL FIELD

The present teaching generally relates to vital sign monitoring. More specifically, the present teaching relates to wireless monitoring vital signs by processing, decomposing and enhancing wireless channel information (CI).

BACKGROUND

Continuous monitoring of respiration as well as heart rate is critical for early detection and prevention of potentially fatal diseases. Current solutions usually require users to wear dedicated devices such as wrist-worn sensors or chest straps, which require to contact human body during the monitoring, making them less convenient and comfortable. With the rapid development of Internet of Things (IoT), wireless sensing has received increasing attention in recent years because of the ubiquitous deployment of wireless devices. It has been proved that the presence of human will affect wireless signal propagation, enabling the functionality of wirelessly monitoring human subjects by analyzing the electromagnetic (EM) wave.

In addition, vehicle monitoring has become a very important application with the ubiquitous deployment of wireless devices in vehicles. For example, by occupant awareness, the vehicle monitoring may enable the identification of the motion and breathing of a pet (pet awareness), identification of subtle motion and breathing of a child (child awareness), detection of motion within the trunk (unknown awareness), detection of broken glass (window breakage) and a hit and run. Existing methods and systems related to vehicle monitoring are not entirely satisfactory in terms of effectiveness, security and safety concerns.

SUMMARY

The present teaching generally relates to vital sign monitoring. More specifically, the present teaching relates to wireless monitoring vital signs by processing, decomposing and enhancing wireless channel information (CI).

In one embodiment, a system for wireless vital sign monitoring is described. The system comprises: a transmitter configured to transmit a wireless signal through a wireless channel of a venue; a receiver configured to receive the wireless signal through the wireless channel; and a processor. The received wireless signal differs from the transmitted wireless signal due to the wireless channel that is impacted by a periodic motion of a vital sign of an object in the venue. The processor is configured for: obtaining a time series of channel information (CI) of the wireless channel based on the received wireless signal, computing a two dimensional (2D) decomposition of the time series of CI (TSCI), enhancing the 2D decomposition, and monitoring the periodic motion of the vital sign based on the enhanced 2D decomposition.

In another embodiment, a wireless device of a system for wireless vital sign monitoring is described. The wireless device comprises: a processor; a memory communicatively coupled to the processor; and a receiver communicatively coupled to the processor. An additional wireless device in the system is configured to transmit a wireless signal through a wireless channel of a venue. The receiver is configured to receive the wireless signal through the wireless channel. The received wireless signal differs from the transmitted wireless signal due to the wireless channel that is impacted by a periodic motion of a vital sign of an object in the venue. The processor is configured for: obtaining a time series of channel information (CI) of the wireless channel based on the received wireless signal, computing a two dimensional (2D) decomposition of the time series of CI (TSCI), enhancing the 2D decomposition, and monitoring the periodic motion of the vital sign based on the enhanced 2D decomposition.

In yet another embodiment, a method for wireless vital sign monitoring is described. The method comprises: transmitting a wireless signal through a wireless channel of a venue; receiving the wireless signal through the wireless channel, wherein the received wireless signal differs from the transmitted wireless signal due to the wireless channel that is impacted by a periodic motion of a vital sign of an object in the venue; obtaining a time series of channel information (CI) of the wireless channel based on the received wireless signal; computing a two dimensional (2D) decomposition of the time series of CI (TSCI); enhancing the 2D decomposition; and monitoring the periodic motion of the vital sign based on the enhanced 2D decomposition.

Other concepts relate to software for implementing the present teaching on wireless vital sign monitoring. Additional novel features will be set forth in part in the description which follows, and in part will become apparent to those skilled in the art upon examination of the following and the accompanying drawings or may be learned by production or operation of the examples. The novel features of the present teachings may be realized and attained by practice or use of various aspects of the methodologies, instrumentalities and combinations set forth in the detailed examples discussed below.

BRIEF DESCRIPTION OF DRAWINGS

The methods, systems, and/or devices described herein are further described in terms of exemplary embodiments. These exemplary embodiments are described in detail with reference to the drawings. These embodiments are non-limiting exemplary embodiments, in which like reference numerals represent similar structures throughout the several views of the drawings.

DETAILED DESCRIPTION

Figure 1A:
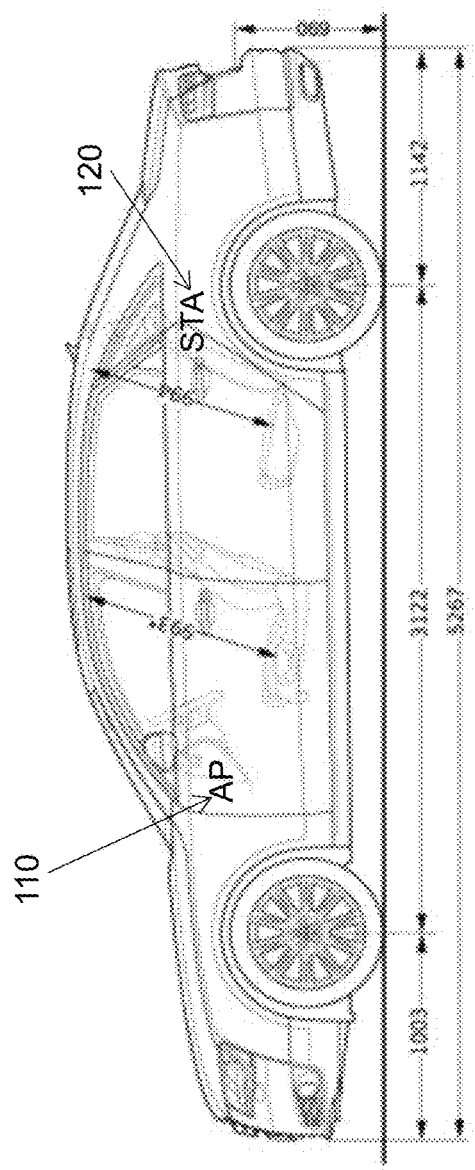
FIG. 1A illustrates a side perspective view of a car including a wireless vital sign detection system, according to some embodiments of the present disclosure.

In one embodiment, the present teaching discloses a method, apparatus, device, system, and/or software (method/apparatus/device/system/software) of a wireless monitoring system. A time series of channel information (CI) of a wireless multipath channel (channel) may be obtained (e.g. dynamically) using a processor, a memory communicatively coupled with the processor and a set of instructions stored in the memory. The time series of CI (TSCI) may be extracted from a wireless signal (signal) transmitted between a Type 1 heterogeneous wireless device (e.g. wireless transmitter, TX) and a Type 2 heterogeneous wireless device (e.g. wireless receiver, RX) in a venue through the channel. The channel may be impacted by an expression (e.g. motion, movement, expression, and/or change in position/pose/shape/expression) of an object in the venue. A characteristics and/or a spatial-temporal information (STI, e.g. motion information) of the object and/or of the motion of the object may be monitored based on the TSCI. A task may be performed based on the characteristics and/or STI. A presentation associated with the task may be generated in a user-interface (UI) on a device of a user. The TSCI may be a wireless signal stream. The TSCI or each CI may be preprocessed. A device may be a station (STA). The symbol "A/B" means "A and/or B" in the present teaching.

The expression may comprise placement, placement of moveable parts, location, position, orientation, identifiable place, region, spatial coordinate, presentation, state, static expression, size, length, width, height, angle, scale, shape, curve, surface, area, volume, pose, posture, manifestation, body language, dynamic expression, motion, motion sequence, gesture, extension, contraction, distortion, deformation, body expression (e.g. head, face, eye, mouth, tongue, hair, voice, neck, limbs, arm, hand, leg, foot, muscle, moveable parts), surface expression (e.g. shape, texture, material, color, electromagnetic (EM) characteristics, visual pattern, wetness, reflectance, translucency, flexibility), material property (e.g. living tissue, hair, fabric, metal, wood, leather, plastic, artificial material, solid, liquid, gas, temperature), movement, activity, behavior, change of expression, and/or some combination.

The wireless signal may comprise: transmitted/received signal, EM radiation, RF signal/transmission, signal in licensed/unlicensed/ISM band, bandlimited signal, baseband signal, wireless/mobile/cellular communication signal, wireless/mobile/cellular network signal, mesh signal, light signal/communication, downlink/uplink signal, unicast/multicast/broadcast signal, standard (e.g. WLAN, WWAN, WPAN, WBAN, international, national, industry, defacto, IEEE, IEEE 802, 802.11/15/16, WiFi, 802.11n/ac/ax/be, 3G/4G/LTE/5G/6G/7G/8G, 3GPP, Bluetooth, BLE, Zigbee, RFID, UWB, WiMax) compliant signal, protocol signal, standard frame, beacon/pilot/probe/enquiry/acknowledgement/handshake/synchronization signal, management/control/data frame, management/control/data signal, standardized wireless/cellular communication protocol, reference signal, source signal, motion probe/detection/sensing signal, and/or series of signals. The wireless signal may comprise a line-of-sight (LOS), and/or a non-LOS component (or path/link). Each CI may be extracted/generated/computed/sensed at a layer (e.g. PHY/MAC layer in OSI model) of Type 2 device and may be obtained by an application (e.g. software, firmware, driver, app, wireless monitoring software/system).

The wireless multipath channel may comprise: a communication channel, analog frequency channel (e.g. with analog carrier frequency near 700/800/900 MHz, 1.8/1.8/2.4/3/5/6/27/60 GHz), coded channel (e.g. in CDMA), and/or channel of a wireless network/system (e.g. WLAN, WiFi, mesh, LTE, 4G/5G, Bluetooth, Zigbee, UWB, RFID, microwave). It may comprise more than one channel. The channels may be consecutive (e.g. with adjacent/overlapping bands) or non-consecutive channels (e.g. non-overlapping WiFi channels, one at 2.4 GHz and one at 5 GHz).

The TSCI may be extracted from the wireless signal at a layer of the Type 2 device (e.g. a layer of OSI reference model, physical layer, data link layer, logical link control layer, media access control (MAC) layer, network layer, transport layer, session layer, presentation layer, application layer, TCP/IP layer, internet layer, link layer). The TSCI may be extracted from a derived signal (e.g. baseband signal, motion detection signal, motion sensing signal) derived from the wireless signal (e.g. RF signal). It may be (wireless) measurements sensed by the communication protocol (e.g. standardized protocol) using existing mechanism (e.g. wireless/cellular communication standard/network, 3G/LTE/4G/5G/6G/7G/8G, WiFi, IEEE 802.11/15/16). The derived signal may comprise a packet with at least one of: a preamble, a header and a payload (e.g. for data/control/ management in wireless links/networks). The TSCI may be extracted from a probe signal (e.g. training sequence, STF, LTF, L-STF, L-LTF, L-SIG, HE-STF, HE-LTF, HE-SIG-A, HE-SIG-B, CEF) in the packet. A motion detection/sensing signal may be recognized/identified base on the probe signal. The packet may be a standard-compliant protocol frame, management frame, control frame, data frame, sounding frame, excitation frame, illumination frame, null data frame, beacon frame, pilot frame, probe frame, request frame, response frame, association frame, reassociation frame, disassociation frame, authentication frame, action frame, report frame, poll frame, announcement frame, extension frame, enquiry frame, acknowledgement frame, RTS frame, CTS frame, QoS frame, CF-Poll frame, CF-Ack frame, block acknowledgement frame, reference frame, training frame, and/or synchronization frame.

The packet may comprise a control data and/or a motion detection probe. A data (e.g. ID/parameters/characteristics/settings/control signal/command/instruction/notification/broadcasting-related information of the Type 1 device) may be obtained from the payload. The wireless signal may be transmitted by the Type 1 device. It may be received by the Type 2 device. A database (e.g. in local server, hub device, cloud server, storage network) may be used to store the TSCI, characteristics, STI, signatures, patterns, behaviors, trends, parameters, analytics, output responses, identification information, user information, device information, channel information, venue (e.g. map, environmental model, network, proximity devices/networks) information, task information, class/category information, presentation (e.g. UI) information, and/or other information.

The Type 1/Type 2 device may comprise at least one of: electronics, circuitry, transmitter (TX)/receiver (RX)/transceiver, RF interface, "Origin Satellite"/"Tracker Bot", unicast/multicast/broadcasting device, wireless source device, source/destination device, wireless node, hub device, target device, motion detection device, sensor device, remote/wireless sensor device, wireless communication device, wireless-enabled device, standard compliant device, and/or receiver. The Type 1 (or Type 2) device may be heterogeneous because, when there are more than one instances of Type 1 (or Type 2) device, they may have different circuitry, enclosure, structure, purpose, auxiliary functionality, chip/IC, processor, memory, software, firmware, network connectivity, antenna, brand, model, appearance, form, shape, color, material, and/or specification. The Type 1/Type 2 device may comprise: access point, router, mesh router, internet-of-things (IoT) device, wireless terminal, one or more radio/RF subsystem/wireless interface (e.g. 2.4 GHz radio, 5 GHz radio, front haul radio, backhaul radio), modem, RF front end, RF/radio chip or integrated circuit (IC).

At least one of: Type 1 device, Type 2 device, a link between them, the object, the characteristics, the STI, the monitoring of the motion, and the task may be associated with an identification (ID) such as UUID. The Type 1/Type 2/another device may obtain/store/retrieve/access/preprocess/condition/process/analyze/monitor/apply the TSCI. The Type 1 and Type 2 devices may communicate network traffic in another channel (e.g. Ethernet, HDMI, USB, Bluetooth, BLE, WiFi, LTE, other network, the wireless multipath channel) in parallel to the wireless signal. The Type 2 device may passively observe/monitor/receive the wireless signal from the Type 1 device in the wireless multipath channel without establishing connection (e.g. association/authentication) with, or requesting service from, the Type 1 device.

The transmitter (i.e. Type 1 device) may function as (play role of) receiver (i.e. Type 2 device) temporarily, sporadically, continuously, repeatedly, interchangeably, alternately, simultaneously, concurrently, and/or contemporaneously; and vice versa. A device may function as Type 1 device (transmitter) and/or Type 2 device (receiver) temporarily, sporadically, continuously, repeatedly, simultaneously, concurrently, and/or contemporaneously. There may be multiple wireless nodes each being Type 1 (TX) and/or Type 2 (RX) device. A TSCI may be obtained between every two nodes when they exchange/communicate wireless signals. The characteristics and/or STI of the object may be monitored individually based on a TSCI, or jointly based on two or more (e.g. all) TSCI.

The motion of the object may be monitored actively (in that Type 1 device, Type 2 device, or both, are wearable of/associated with the object) and/or passively (in that both Type 1 and Type 2 devices are not wearable of/associated with the object). It may be passive because the object may not be associated with the Type 1 device and/or the Type 2 device. The object (e.g. user, an automated guided vehicle or AGV) may not need to carry/install any wearables/fixtures (i.e. the Type 1 device and the Type 2 device are not wearable/attached devices that the object needs to carry in order perform the task). It may be active because the object may be associated with either the Type 1 device and/or the Type 2 device. The object may carry (or installed) a wearable/a fixture (e.g. the Type 1 device, the Type 2 device, a device communicatively coupled with either the Type 1 device or the Type 2 device).

The presentation may be visual, audio, image, video, animation, graphical presentation, text, etc. A computation of the task may be performed by a processor (or logic unit) of the Type 1 device, a processor (or logic unit) of an IC of the Type 1 device, a processor (or logic unit) of the Type 2 device, a processor of an IC of the Type 2 device, a local server, a cloud server, a data analysis subsystem, a signal analysis subsystem, and/or another processor. The task may be performed with/without reference to a wireless fingerprint or a baseline (e.g. collected, processed, computed, transmitted and/or stored in a training phase/survey/current survey/previous survey/recent survey/initial wireless survey, a passive fingerprint), a training, a profile, a trained profile, a static profile, a survey, an initial wireless survey, an initial setup, an installation, a re-training, an updating and a reset.

The Type 1 device (TX device) may comprise at least one heterogeneous wireless transmitter. The Type 2 device (RX device) may comprise at least one heterogeneous wireless receiver. The Type 1 device and the Type 2 device may be collocated. The Type 1 device and the Type 2 device may be the same device. Any device may have a data processing unit/apparatus, a computing unit/system, a network unit/system, a processor (e.g. logic unit), a memory communicatively coupled with the processor, and a set of instructions stored in the memory to be executed by the processor. Some processors, memories and sets of instructions may be coordinated.

There may be multiple Type 1 devices interacting (e.g. communicating, exchange signal/control/notification/other data) with the same Type 2 device (or multiple Type 2 devices), and/or there may be multiple Type 2 devices interacting with the same Type 1 device. The multiple Type 1 devices/Type 2 devices may be synchronized and/or asynchronous, with same/different window width/size and/or time shift, same/different synchronized start time, synchronized end time, etc. Wireless signals sent by the multiple Type 1 devices may be sporadic, temporary, continuous, repeated, synchronous, simultaneous, concurrent, and/or contemporaneous. The multiple Type 1 devices/Type 2 devices may operate independently and/or collaboratively. A Type 1 and/or Type 2 device may have/comprise/be heterogeneous hardware circuitry (e.g. a heterogeneous chip or a heterogeneous IC capable of generating/receiving the wireless signal, extracting CI from received signal, or making the CI available). They may be communicatively coupled to same or different servers (e.g. cloud server, edge server, local server, hub device).

Operation of one device may be based on operation, state, internal state, storage, processor, memory output, physical location, computing resources, network of another device. Difference devices may communicate directly, and/or via another device/server/hub device/cloud server. The devices may be associated with one or more users, with associated settings. The settings may be chosen once, pre-programmed, and/or changed (e.g. adjusted, varied, modified)/varied overtime. There may be additional steps in the method. The steps and/or the additional steps of the method may be performed in the order shown or in another order. Any steps may be performed in parallel, iterated, or otherwise repeated or performed in another manner. A user may be human, adult, older adult, man, woman, juvenile, child, baby, pet, animal, creature, machine, computer module/software, etc.

In the case of one or multiple Type 1 devices interacting with one or multiple Type 2 devices, any processing (e.g. time domain, frequency domain) may be different for different devices. The processing may be based on locations, orientation, direction, roles, user-related characteristics, settings, configurations, available resources, available bandwidth, network connection, hardware, software, processor, co-processor, memory, battery life, available power, antennas, antenna types, directional/unidirectional characteristics of the antenna, power setting, and/or other parameters/characteristics of the devices.

The wireless receiver (e.g. Type 2 device) may receive the signal and/or another signal from the wireless transmitter (e.g. Type 1 device). The wireless receiver may receive another signal from another wireless transmitter (e.g. a second Type 1 device). The wireless transmitter may transmit the signal and/or another signal to another wireless receiver (e.g. a second Type 2 device). The wireless transmitter, wireless receiver, another wireless receiver and/or another wireless transmitter may be moving with the object and/or another object. The another object may be tracked.

The Type 1 and/or Type 2 device may be capable of wirelessly coupling with at least two Type 2 and/or Type 1 devices. The Type 1 device may be caused/controlled to switch/establish wireless coupling (e.g. association, authentication) from the Type 2 device to a second Type 2 device at another location in the venue. Similarly, the Type 2 device may be caused/controlled to switch/establish wireless coupling from the Type 1 device to a second Type 1 device at yet another location in the venue. The switching may be controlled by a server (or a hub device), the processor, the Type 1 device, the Type 2 device, and/or another device. The radio used before and after switching may be different. A second wireless signal (second signal) may be caused to be transmitted between the Type 1 device and the second Type 2 device (or between the Type 2 device and the second Type 1 device) through the channel. A second TSCI of the channel extracted from the second signal may be obtained. The second signal may be the first signal. The characteristics, STI and/or another quantity of the object may be monitored based on the second TSCI. The Type 1 device and the Type 2 device may be the same. The characteristics, STI and/or another quantity with different time stamps may form a waveform. The waveform may be displayed in the presentation.

The wireless signal and/or another signal may have data embedded. The wireless signal may be a series of probe signals (e.g. a repeated transmission of probe signals, a re-use of one or more probe signals). The probe signals may change/vary over time. A probe signal may be a standard compliant signal, protocol signal, standardized wireless protocol signal, control signal, data signal, wireless communication network signal, cellular network signal, WiFi signal, LTE/5G/6G/7G signal, reference signal, beacon signal, motion detection signal, and/or motion sensing signal. A probe signal may be formatted according to a wireless network standard (e.g. WiFi), a cellular network standard (e.g. LTE/5G/6G), or another standard. A probe signal may comprise a packet with a header and a payload. A probe signal may have data embedded. The payload may comprise data. A probe signal may be replaced by a data signal. The probe signal may be embedded in a data signal. The wireless receiver, wireless transmitter, another wireless receiver and/or another wireless transmitter may be associated with at least one processor, memory communicatively coupled with respective processor, and/or respective set of instructions stored in the memory which when executed cause the processor to perform any and/or all steps needed to determine the STI (e.g. motion information), initial STI, initial time, direction, instantaneous location, instantaneous angle, and/or speed, of the object.

The processor, the memory and/or the set of instructions may be associated with the Type 1 device, one of the at least one Type 2 device, the object, a device associated with the object, another device associated with the venue, a cloud server, a hub device, and/or another server.

The Type 1 device may transmit the signal in a broadcasting manner to at least one Type 2 device(s) through the channel in the venue. The signal is transmitted without the Type 1 device establishing wireless connection (e.g. association, authentication) with any Type 2 device, and without any Type 2 device requesting services from the Type 1 device. The Type 1 device may transmit to a particular media access control (MAC) address common for more than one Type 2 devices. Each Type 2 device may adjust its MAC address to the particular MAC address. The particular MAC address may be associated with the venue. The association may be recorded in an association table of an Association Server (e.g. hub device). The venue may be identified by the Type 1 device, a Type 2 device and/or another device based on the particular MAC address, the series of probe signals, and/or the at least one TSCI extracted from the probe signals.

For example, a Type 2 device may be moved to a new location in the venue (e.g. from another venue). The Type 1 device may be newly set up in the venue such that the Type 1 and Type 2 devices are not aware of each other. During set up, the Type 1 device may be instructed/guided/caused/controlled (e.g. using dummy receiver, using hardware pin setting/connection, using stored setting, using local setting, using remote setting, using downloaded setting, using hub device, or using server) to send the series of probe signals to the particular MAC address. Upon power up, the Type 2 device may scan for probe signals according to a table of MAC addresses (e.g. stored in a designated source, server, hub device, cloud server) that may be used for broadcasting at different locations (e.g. different MAC address used for different venue such as house, office, enclosure, floor, multi-storey building, store, airport, mall, stadium, hall, station, subway, lot, area, zone, region, district, city, country, continent). When the Type 2 device detects the probe signals sent to the particular MAC address, the Type 2 device can use the table to identify the venue based on the MAC address.

A location of a Type 2 device in the venue may be computed based on the particular MAC address, the series of probe signals, and/or the at least one TSCI obtained by the Type 2 device from the probe signals. The computing may be performed by the Type 2 device.

The particular MAC address may be changed (e.g. adjusted, varied, modified) overtime. It may be changed according to a time table, rule, policy, mode, condition, situation and/or change. The particular MAC address may be selected based on availability of the MAC address, a pre-selected list, collision pattern, traffic pattern, data traffic between the Type 1 device and another device, effective bandwidth, random selection, and/or a MAC address switching plan. The particular MAC address may be the MAC address of a second wireless device (e.g. a dummy receiver, or a receiver that serves as a dummy receiver).

The Type 1 device may transmit the probe signals in a channel selected from a set of channels. At least one CI of the selected channel may be obtained by a respective Type 2 device from the probe signal transmitted in the selected channel.

The selected channel may be changed (e.g. adjusted, varied, modified) overtime. The change may be according to a time table, rule, policy, mode, condition, situation, and/or change. The selected channel may be selected based on availability of channels, random selection, a pre-selected list, co-channel interference, inter-channel interference, channel traffic pattern, data traffic between the Type 1 device and another device, effective bandwidth associated with channels, security criterion, channel switching plan, a criterion, a quality criterion, a signal quality condition, and/or consideration.

The particular MAC address and/or an information of the selected channel may be communicated between the Type 1 device and a server (e.g. hub device) through a network. The particular MAC address and/or the information of the selected channel may also be communicated between a Type 2 device and a server (e.g. hub device) through another network. The Type 2 device may communicate the particular MAC address and/or the information of the selected channel to another Type 2 device (e.g. via mesh network, Bluetooth, WiFi, NFC, ZigBee, etc.). The particular MAC address and/or selected channel may be chosen by a server (e.g. hub device). The particular MAC address and/or selected channel may be signaled in an announcement channel by the Type 1 device, the Type 2 device and/or a server (e.g. hub device). Before being communicated, any information may be pre-processed.

Wireless connection (e.g. association, authentication) between the Type 1 device and another wireless device may be established (e.g. using a signal handshake). The Type 1 device may send a first handshake signal (e.g. sounding frame, probe signal, request-to-send RTS) to the another device. The another device may reply by sending a second handshake signal (e.g. a command, or a clear-to-send CTS) to the Type 1 device, triggering the Type 1 device to transmit the signal (e.g. series of probe signals) in the broadcasting manner to multiple Type 2 devices without establishing connection with any Type 2 device. The second handshake signals may be a response or an acknowledge (e.g. ACK) to the first handshake signal. The second handshake signal may contain a data with information of the venue, and/or the Type 1 device. The another device may be a dummy device with a purpose (e.g. primary purpose, secondary purpose) to establish the wireless connection with the Type 1 device, to receive the first signal, and/or to send the second signal. The another device may be physically attached to the Type 1 device.

In another example, the another device may send a third handshake signal to the Type 1 device triggering the Type 1 device to broadcast the signal (e.g. series of probe signals) to multiple Type 2 devices without establishing connection (e.g. association, authentication) with any Type 2 device. The Type 1 device may reply to the third special signal by transmitting a fourth handshake signal to the another device. The another device may be used to trigger more than one Type 1 devices to broadcast. The triggering may be sequential, partially sequential, partially parallel, or fully parallel. The another device may have more than one wireless circuitries to trigger multiple transmitters in parallel. Parallel trigger may also be achieved using at least one yet another device to perform the triggering (similar to what as the another device does) in parallel to the another device. The another device may not communicate (or suspend communication) with the Type 1 device after establishing connection with the Type 1 device. Suspended communication may be resumed. The another device may enter an inactive mode, hibernation mode, sleep mode, stand-by mode, low-power mode, OFF mode and/or power-down mode, after establishing the connection with the Type 1 device. The another device may have the particular MAC address so that the Type 1 device sends the signal to the particular MAC address. The Type 1 device and/or the another device may be controlled and/or coordinated by a first processor associated with the Type 1 device, a second processor associated with the another device, a third processor associated with a designated source and/or a fourth processor associated with another device. The first and second processors may coordinate with each other.

A first series of probe signals may be transmitted by a first antenna of the Type 1 device to at least one first Type 2 device through a first channel in a first venue. A second series of probe signals may be transmitted by a second antenna of the Type 1 device to at least one second Type 2 device through a second channel in a second venue. The first series and the second series may/may not be different. The at least one first Type 2 device may/may not be different from the at least one second Type 2 device. The first and/or second series of probe signals may be broadcasted without connection (e.g. association, authentication) established between the Type 1 device and any Type 2 device. The first and second antennas may be same/different.

The two venues may have different sizes, shape, multipath characteristics. The first and second venues may overlap. The respective immediate areas around the first and second antennas may overlap. The first and second channels may be same/different. For example, the first one may be WiFi while the second may be LTE. Or, both may be WiFi, but the first one may be 2.4 GHz WiFi and the second may be 5 GHz WiFi. Or, both may be 2.4 GHz WiFi, but have different channel numbers, SSID names, and/or WiFi settings.

Each Type 2 device may obtain at least one TSCI from the respective series of probe signals, the CI being of the respective channel between the Type 2 device and the Type 1 device. Some first Type 2 device(s) and some second Type 2 device(s) may be the same. The first and second series of probe signals may be synchronous/asynchronous. A probe signal may be transmitted with data or replaced by a data signal. The first and second antennas may be the same.

The first series of probe signals may be transmitted at a first rate (e.g. 30 Hz). The second series of probe signals may be transmitted at a second rate (e.g. 200 Hz). The first and second rates may be same/different. The first and/or second rate may be changed (e.g. adjusted, varied, modified) over time. The change may be according to a time table, rule, policy, mode, condition, situation, and/or change. Any rate may be changed (e.g. adjusted, varied, modified) over time.

The first and/or second series of probe signals may be transmitted to a first MAC address and/or second MAC address respectively. The two MAC addresses may be same/different. The first series of probe signals may be transmitted in a first channel. The second series of probe signals may be transmitted in a second channel. The two channels may be same/different. The first or second MAC address, first or second channel may be changed over time. Any change may be according to a time table, rule, policy, mode, condition, situation, and/or change.

The Type 1 device and another device may be controlled and/or coordinated, physically attached, or may be of/in/of a common device. They may be controlled by/connected to a common data processor, or may be connected to a common bus interconnect/network/LAN/Bluetooth network/NFC network/BLE network/wired network/wireless network/mesh network/mobile network/cloud. They may share a common memory, or be associated with a common user, user device, profile, account, identity (ID), identifier, household, house, physical address, location, geographic coordinate, IP subnet, SSID, home device, office device, and/or manufacturing device.

Each Type 1 device may be a signal source of a set of respective Type 2 devices (i.e. it sends a respective signal (e.g. respective series of probe signals) to the set of respective Type 2 devices). Each respective Type 2 device chooses the Type 1 device from among all Type 1 devices as its signal source. Each Type 2 device may choose asynchronously. At least one TSCI may be obtained by each respective Type 2 device from the respective series of probe signals from the Type 1 device, the CI being of the channel between the Type 2 device and the Type 1 device.

The respective Type 2 device chooses the Type 1 device from among all Type 1 devices as its signal source based on identity (ID) or identifier of Type 1/Type 2 device, task to be performed, past signal source, history (e.g. of past signal source, Type 1 device, another Type 1 device, respective Type 2 receiver, and/or another Type 2 receiver), threshold for switching signal source, and/or information of a user, account, access info, parameter, characteristics, and/or signal strength (e.g. associated with the Type 1 device and/or the respective Type 2 receiver).

Initially, the Type 1 device may be signal source of a set of initial respective Type 2 devices (i.e. the Type 1 device sends a respective signal (series of probe signals) to the set of initial respective Type 2 devices) at an initial time. Each initial respective Type 2 device chooses the Type 1 device from among all Type 1 devices as its signal source.

The signal source (Type 1 device) of a particular Type 2 device may be changed (e.g. adjusted, varied, modified) when (1) time interval between two adjacent probe signals (e.g. between current probe signal and immediate past probe signal, or between next probe signal and current probe signal) received from current signal source of the Type 2 device exceeds a first threshold; (2) signal strength associated with current signal source of the Type 2 device is below a second threshold; (3) a processed signal strength associated with current signal source of the Type 2 device is below a third threshold, the signal strength processed with low pass filter, band pass filter, median filter, moving average filter, weighted averaging filter, linear filter and/or non-linear filter; and/or (4) signal strength (or processed signal strength) associated with current signal source of the Type 2 device is below a fourth threshold for a significant percentage of a recent time window (e.g. 70%, 80%, 90%). The percentage may exceed a fifth threshold. The first, second, third, fourth and/or fifth thresholds may be time varying.

Condition (1) may occur when the Type 1 device and the Type 2 device become progressively far away from each other, such that some probe signal from the Type 1 device becomes too weak and is not received by the Type 2 device. Conditions (2)-(4) may occur when the two devices become far from each other such that the signal strength becomes very weak.

The signal source of the Type 2 device may not change if other Type 1 devices have signal strength weaker than a factor (e.g. 1, 1.1, 1.2, or 1.5) of the current signal source.

If the signal source is changed (e.g. adjusted, varied, modified), the new signal source may take effect at a near future time (e.g. the respective next time). The new signal source may be the Type 1 device with strongest signal strength, and/or processed signal strength. The current and new signal source may be same/different.

A list of available Type 1 devices may be initialized and maintained by each Type 2 device. The list may be updated by examining signal strength and/or processed signal strength associated with the respective set of Type 1 devices. A Type 2 device may choose between a first series of probe signals from a first Type 1 device and a second series of probe signals from a second Type 1 device based on: respective probe signal rate, MAC addresses, channels, characteristics/properties/states, task to be performed by the Type 2 device, signal strength of first and second series, and/or another consideration.

The series of probe signals may be transmitted at a regular rate (e.g. 100 Hz). The series of probe signals may be scheduled at a regular interval (e.g. 0.01 s for 100 Hz), but each probe signal may experience small time perturbation, perhaps due to timing requirement, timing control, network control, handshaking, message passing, collision avoidance, carrier sensing, congestion, availability of resources, and/or another consideration.

The rate may be changed (e.g. adjusted, varied, modified). The change may be according to a time table (e.g. changed once every hour), rule, policy, mode, condition and/or change (e.g. changed whenever some event occur). For example, the rate may normally be 100 Hz, but changed to 1000 Hz in demanding situations, and to 1 Hz in low power/standby situation. The probe signals may be sent in burst.

The probe signal rate may change based on a task performed by the Type 1 device or Type 2 device (e.g. a task may need 100 Hz normally and 1000 Hz momentarily for 20 seconds). In one example, the transmitters (Type 1 devices), receivers (Type 2 device), and associated tasks may be associated adaptively (and/or dynamically) to classes (e.g. classes that are: low-priority, high-priority, emergency, critical, regular, privileged, non-subscription, subscription, paying, and/or non-paying). A rate (of a transmitter) may be adjusted for the sake of some class (e.g. high priority class). When the need of that class changes, the rate may be changed (e.g. adjusted, varied, modified). When a receiver has critically low power, the rate may be reduced to reduce power consumption of the receiver to respond to the probe signals. In one example, probe signals may be used to transfer power wirelessly to a receiver (Type 2 device), and the rate may be adjusted to control the amount of power transferred to the receiver.

The rate may be changed by (or based on): a server (e.g. hub device), the Type 1 device and/or the Type 2 device. Control signals may be communicated between them. The server may monitor, track, forecast and/or anticipate the needs of the Type 2 device and/or the tasks performed by the Type 2 device, and may control the Type 1 device to change the rate. The server may make scheduled changes to the rate according to a time table. The server may detect an emergency situation and change the rate immediately. The server may detect a developing condition and adjust the rate gradually.

The characteristics and/or STI (e.g. motion information) may be monitored individually based on a TSCI associated with a particular Type 1 device and a particular Type 2 device, and/or monitored jointly based on any TSCI associated with the particular Type 1 device and any Type 2 device, and/or monitored jointly based on any TSCI associated with the particular Type 2 device and any Type 1 device, and/or monitored globally based on any TSCI associated with any Type 1 device and any Type 2 device. Any joint monitoring may be associated with: a user, user account, profile, household, map of venue, environmental model of the venue, and/or user history, etc.

A first channel between a Type 1 device and a Type 2 device may be different from a second channel between another Type 1 device and another Type 2 device. The two channels may be associated with different frequency bands, bandwidth, carrier frequency, modulation, wireless standards, coding, encryption, payload characteristics, networks, network ID, SSID, network characteristics, network settings, and/or network parameters, etc.

The two channels may be associated with different kinds of wireless system (e.g. two of the following: WiFi, LTE, LTE-A, LTE-U, 2.5G, 3G, 3.5G, 4G, beyond 4G, 5G, 6G, 7G, a cellular network standard, UMTS, 3GPP, GSM, EDGE, TDMA, FDMA, CDMA, WCDMA, TD-SCDMA, 802.11 system, 802.15 system, 802.16 system, mesh network, Zigbee, NFC, WiMax, Bluetooth, BLE, RFID, UWB, microwave system, radar like system). For example, one is WiFi and the other is LTE.

The two channels may be associated with similar kinds of wireless system, but in different network. For example, the first channel may be associated with a WiFi network named "Pizza and Pizza" in the 2.4 GHz band with a bandwidth of 20 MHz while the second may be associated with a WiFi network with SSID of "StarBud hotspot" in the 5 GHz band with a bandwidth of 40 MHz. The two channels may be different channels in same network (e.g. the "StarBud hotspot" network).

In one embodiment, a wireless monitoring system may comprise training a classifier of multiple events in a venue based on training TSCI associated with the multiple events. A CI or TSCI associated with an event may be considered/ may comprise a wireless sample/characteristics/fingerprint associated with the event (and/or the venue, the environment, the object, the motion of the object, a state/emotional state/mental state/condition/stage/gesture/gait/action/movement/activity/daily activity/history/event of the object, etc.).

For each of the multiple known events happening in the venue in a respective training (e.g. surveying, wireless survey, initial wireless survey) time period associated with the known event, a respective training wireless signal (e.g. a respective series of training probe signals) may be transmitted by an antenna of a first Type 1 heterogeneous wireless device using a processor, a memory and a set of instructions of the first Type 1 device to at least one first Type 2 heterogeneous wireless device through a wireless multipath channel in the venue in the respective training time period.

At least one respective time series of training CI (training TSCI) may be obtained asynchronously by each of the at least one first Type 2 device from the (respective) training signal. The CI may be CI of the channel between the first Type 2 device and the first Type 1 device in the training time period associated with the known event. The at least one training TSCI may be preprocessed. The training may be a wireless survey (e.g. during installation of Type 1 device and/or Type 2 device).

For a current event happening in the venue in a current time period, a current wireless signal (e.g. a series of current probe signals) may be transmitted by an antenna of a second Type 1 heterogeneous wireless device using a processor, a memory and a set of instructions of the second Type 1 device to at least one second Type 2 heterogeneous wireless device through the channel in the venue in the current time period associated with the current event.

At least one time series of current CI (current TSCI) may be obtained asynchronously by each of the at least one second Type 2 device from the current signal (e.g. the series of current probe signals). The CI may be CI of the channel between the second Type 2 device and the second Type 1 device in the current time period associated with the current event. The at least one current TSCI may be preprocessed.

The classifier may be applied to classify at least one current TSCI obtained from the series of current probe signals by the at least one second Type 2 device, to classify at least one portion of a particular current TSCI, and/or to classify a combination of the at least one portion of the particular current TSCI and another portion of another TSCI. The classifier may partition TSCI (or the characteristics/STI or other analytics or output responses) into clusters and associate the clusters to specific events/objects/subjects/ locations/movements/activities. Labels/tags may be generated for the clusters. The clusters may be stored and retrieved. The classifier may be applied to associate the current TSCI (or characteristics/STI or the other analytics/ output response, perhaps associated with a current event) with: a cluster, a known/specific event, a class/category/ group/grouping/list/cluster/set of known events/subjects/locations/movements/activities, an unknown event, a class/ category/group/grouping/list/cluster/set of unknown events/ subjects/locations/movements/activities, and/or another event/subject/location/movement/activity/class/category/ group/grouping/list/cluster/set. Each TSCI may comprise at least one CI each associated with a respective timestamp. Two TSCI associated with two Type 2 devices may be different with different: starting time, duration, stopping time, amount of CI, sampling frequency, sampling period. Their CI may have different features. The first and second Type 1 devices may be at same location in the venue. They may be the same device. The at least one second Type 2 device (or their locations) may be a permutation of the at least one first Type 2 device (or their locations). A particular second Type 2 device and a particular first Type 2 device may be the same device.

A subset of the first Type 2 device and a subset of the second Type 2 device may be the same. The at least one second Type 2 device and/or a subset of the at least one second Type 2 device may be a subset of the at least one first Type 2 device. The at least one first Type 2 device and/or a subset of the at least one first Type 2 device may be a permutation of a subset of the at least one second Type 2 device. The at least one second Type 2 device and/or a subset of the at least one second Type 2 device may be a permutation of a subset of the at least one first Type 2 device. The at least one second Type 2 device and/or a subset of the at least one second Type 2 device may be at same respective location as a subset of the at least one first Type 2 device. The at least one first Type 2 device and/or a subset of the at least one first Type 2 device may be at same respective location as a subset of the at least one second Type 2 device.

The antenna of the Type 1 device and the antenna of the second Type 1 device may be at same location in the venue. Antenna(s) of the at least one second Type 2 device and/or antenna(s) of a subset of the at least one second Type 2 device may be at same respective location as respective antenna(s) of a subset of the at least one first Type 2 device. Antenna(s) of the at least one first Type 2 device and/or antenna(s) of a subset of the at least one first Type 2 device may be at same respective location(s) as respective antenna(s) of a subset of the at least one second Type 2 device.

A first section of a first time duration of the first TSCI and a second section of a second time duration of the second section of the second TSCI may be aligned. A map between items of the first section and items of the second section may be computed. The first section may comprise a first segment (e.g. subset) of the first TSCI with a first starting/ending time, and/or another segment (e.g. subset) of a processed first TSCI. The processed first TSCI may be the first TSCI processed by a first operation. The second section may comprise a second segment (e.g. subset) of the second TSCI with a second starting time and a second ending time, and another segment (e.g. subset) of a processed second TSCI. The processed second TSCI may be the second TSCI processed by a second operation. The first operation and/or the second operation may comprise: subsampling, re-sampling, interpolation, filtering, transformation, feature extraction, pre-processing, and/or another operation.

A first item of the first section may be mapped to a second item of the second section. The first item of the first section may also be mapped to another item of the second section. Another item of the first section may also be mapped to the second item of the second section. The mapping may be one-to-one, one-to-many, many-to-one, many-to-many. At least one function of at least one of: the first item of the first section of the first TSCI, another item of the first TSCI, timestamp of the first item, time difference of the first item, time differential of the first item, neighboring timestamp of the first item, another timestamp associated with the first item, the second item of the second section of the second TSCI, another item of the second TSCI, timestamp of the second item, time difference of the second item, time differential of the second item, neighboring timestamp of the second item, and another timestamp associated with the second item, may satisfy at least one constraint.

One constraint may be that a difference between the timestamp of the first item and the timestamp of the second item may be upper-bounded by an adaptive (and/or dynamically adjusted) upper threshold and lower-bounded by an adaptive lower threshold.

The first section may be the entire first TSCI. The second section may be the entire second TSCI. The first time duration may be equal to the second time duration. A section of a time duration of a TSCI may be determined adaptively (and/or dynamically). A tentative section of the TSCI may be computed. A starting time and an ending time of a section (e.g. the tentative section, the section) may be determined. The section may be determined by removing a beginning portion and an ending portion of the tentative section. A beginning portion of a tentative section may be determined as follows. Iteratively, items of the tentative section with increasing timestamp may be considered as a current item, one item at a time.

In each iteration, at least one activity measure/index may be computed and/or considered. The at least one activity measure may be associated with at least one of: the current item associated with a current timestamp, past items of the tentative section with timestamps not larger than the current timestamp, and/or future items of the tentative section with timestamps not smaller than the current timestamp. The current item may be added to the beginning portion of the tentative section if at least one criterion (e.g. quality criterion, signal quality condition) associated with the at least one activity measure is satisfied.

The at least one criterion associated with the activity measure may comprise at least one of: (a) the activity measure is smaller than an adaptive (e.g. dynamically adjusted) upper threshold, (b) the activity measure is larger than an adaptive lower threshold, (c) the activity measure is smaller than an adaptive upper threshold consecutively for at least a predetermined amount of consecutive timestamps, (d) the activity measure is larger than an adaptive lower threshold consecutively for at least another predetermined amount of consecutive timestamps, (e) the activity measure is smaller than an adaptive upper threshold consecutively for at least a predetermined percentage of the predetermined amount of consecutive timestamps, (f) the activity measure is larger than an adaptive lower threshold consecutively for at least another predetermined percentage of the another predetermined amount of consecutive timestamps, (g) another activity measure associated with another timestamp associated with the current timestamp is smaller than another adaptive upper threshold and larger than another adaptive lower threshold, (h) at least one activity measure associated with at least one respective timestamp associated with the current timestamp is smaller than respective upper threshold and larger than respective lower threshold, (i) percentage of timestamps with associated activity measure smaller than respective upper threshold and larger than respective lower threshold in a set of timestamps associated with the current timestamp exceeds a threshold, and (j) another criterion (e.g. a quality criterion, signal quality condition).

An activity measure/index associated with an item at time $T1$ may comprise at least one of: (1) a first function of the item at time $T1$ and an item at time $T1-D1$, wherein $D1$ is a pre-determined positive quantity (e.g. a constant time offset), (2) a second function of the item at time $T1$ and an item at time $T1+D1$, (3) a third function of the item at time $T1$ and an item at time $T2$, wherein $T2$ is a pre-determined quantity (e.g. a fixed initial reference time; $T2$ may be changed (e.g. adjusted, varied, modified) over time; $T2$ may be updated periodically; $T2$ may be the beginning of a time period and $T1$ may be a sliding time in the time period), and (4) a fourth function of the item at time $T1$ and another item.

At least one of: the first function, the second function, the third function, and/or the fourth function may be a function (e.g. $F(X, Y, \ldots)$) with at least two arguments: X and Y. The two arguments may be scalars. The function (e.g. F) may be a function of at least one of: $X$, $Y$, $(X-Y)$, $(Y-X)$, $abs(X-Y)$, $X^a$, $Y^B$, $abs(X^a - Y^B)$, $(X-Y)^a$, $(X/Y)$, $(X+a)/(Y+b)$, $(X^a/Y^B)$, and $((X/Y)^a - b)$, wherein a and b are may be some predetermined quantities. For example, the function may simply be $abs(X-Y)$, or $(X-Y)^2$, $(X-Y)^4$. The function may be a robust function. For example, the function may be $(X-Y)^2$ when $abs(X-Y)$ is less than a threshold T, and (X−Y)+a when abs(X−Y) is larger than T. Alternatively, the function may be a constant when abs(X−Y) is larger than T. The function may also be bounded by a slowly increasing function when abs(X−y) is larger than T, so that outliers cannot severely affect the result. Another example of the function may be (abs(X/Y)−a), where a=1. In this way, if X=Y (i.e. no change or no activity), the function will give a value of 0. If X is larger than Y, (X/Y) will be larger than 1 (assuming X and Y are positive) and the function will be positive. And if X is less than Y, (X/Y) will be smaller than 1 and the function will be negative. In another example, both arguments X and Y may be n-tuples such that X=(x_1, x_2, . . . , x_n) and Y=(y_1, y_2, . . . , y_n). The function may be a function of at least one of x_i, y_i, (x_i−y_i), (y_i−x_i), abs(x_i−y_i), x_i^a, y_i^b, abs(x_i^a−y_i^b), (x_i−y_i)^a, (x_i/y_i), (x_i+a)/(y_i+b), (x_i^a/y_i^B), and ((x_i/y_i)^a−b), wherein i is a component index of the n-tuple X and Y, and 1<=i<=n, e.g. component index of x_1 is i=1, component index of x_2 is i=2. The function may comprise a component-by-component summation of another function of at least one of the following: x_i, y_i, (x_i−y_i), (y_i−x_i), abs(x_i−y_i), x_i^a, y_i^b, abs(x_i^a−y_i^b), (x_i−y_i)^a, (x_i/y_i), (x_i+a)/(y_i+b), (x_i^a/y_i^b), and ((x_i/y_i)^a−b), wherein i is the component index of the n-tuple X and Y. For example, the function may be in a form of sum_{i=1}^n (abs(x_i/y_i)−1)/n, or sum_{i=1}^n w_i*(abs(x_i/y_i)−1), where w_i is some weight for component i.

The map may be computed using dynamic time warping (DTW). The DTW may comprise a constraint on at least one of: the map, the items of the first TSCI, the items of the second TSCI, the first time duration, the second time duration, the first section, and/or the second section. Suppose in the map, the i^{th}domain item is mapped to the j^{th}range item. The constraint may be on admissible combination of i and j (constraint on relationship between i and j). Mismatch cost between a first section of a first time duration of a first TSCI and a second section of a second time duration of a second TSCI may be computed.

The first section and the second section may be aligned such that a map comprising more than one links may be established between first items of the first TSCI and second items of the second TSCI. With each link, one of the first items with a first timestamp may be associated with one of the second items with a second timestamp. A mismatch cost between the aligned first section and the aligned second section may be computed. The mismatch cost may comprise a function of: an item-wise cost between a first item and a second item associated by a particular link of the map, and a link-wise cost associated with the particular link of the map.

The aligned first section and the aligned second section may be represented respectively as a first vector and a second vector of same vector length. The mismatch cost may comprise at least one of: an inner product, inner-product-like quantity, quantity based on correlation, correlation indicator, quantity based on covariance, discriminating score, distance, Euclidean distance, absolute distance, Lk distance (e.g. L1, L2, . . . ), weighted distance, distance-like quantity and/or another similarity value, between the first vector and the second vector. The mismatch cost may be normalized by the respective vector length.

A parameter derived from the mismatch cost between the first section of the first time duration of the first TSCI and the second section of the second time duration of the second TSCI may be modeled with a statistical distribution. At least one of: a scale parameter, location parameter and/or another parameter, of the statistical distribution may be estimated.

The first section of the first time duration of the first TSCI may be a sliding section of the first TSCI. The second section of the second time duration of the second TSCI may be a sliding section of the second TSCI.

A first sliding window may be applied to the first TSCI and a corresponding second sliding window may be applied to the second TSCI. The first sliding window of the first TSCI and the corresponding second sliding window of the second TSCI may be aligned.

Mismatch cost between the aligned first sliding window of the first TSCI and the corresponding aligned second sliding window of the second TSCI may be computed. The current event may be associated with at least one of: the known event, the unknown event and/or the another event, based on the mismatch cost.

The classifier may be applied to at least one of: each first section of the first time duration of the first TSCI, and/or each second section of the second time duration of the second TSCI, to obtain at least one tentative classification results. Each tentative classification result may be associated with a respective first section and a respective second section.

The current event may be associated with at least one of: the known event, the unknown event, a class/category/group/grouping/list/set of unknown events, and/or the another event, based on the mismatch cost. The current event may be associated with at least one of: the known event, the unknown event and/or the another event, based on a largest number of tentative classification results in more than one sections of the first TSCI and corresponding more than sections of the second TSCI. For example, the current event may be associated with a particular known event if the mismatch cost points to the particular known event for N consecutive times (e.g. N=10). In another example, the current event may be associated with a particular known event if the percentage of mismatch cost within the immediate past N consecutive N pointing to the particular known event exceeds a certain threshold (e.g. >80%).

In another example, the current event may be associated with a known event that achieves smallest mismatch cost for the most times within a time period. The current event may be associated with a known event that achieves smallest overall mismatch cost, which is a weighted average of at least one mismatch cost associated with the at least one first sections. The current event may be associated with a particular known event that achieves smallest of another overall cost. The current event may be associated with the "unknown event" if none of the known events achieve mismatch cost lower than a first threshold T1 in a sufficient percentage of the at least one first section. The current event may also be associated with the "unknown event" if none of the events achieve an overall mismatch cost lower than a second threshold T2. The current event may be associated with at least one of: the known event, the unknown event and/or the another event, based on the mismatch cost and additional mismatch cost associated with at least one additional section of the first TSCI and at least one additional section of the second TSCI. The known events may comprise at least one of: a door closed event, door open event, window closed event, window open event, multi-state event, on-state event, off-state event, intermediate state event, continuous state event, discrete state event, human-present event, human-absent event, sign-of-life-present event, and/or a sign-of-life-absent event.

A projection for each CI may be trained using a dimension reduction method based on the training TSCI. The dimension reduction method may comprise at least one of: principal component analysis (PCA), PCA with different kernel, independent component analysis (ICA), Fisher linear discriminant, vector quantization, supervised learning, unsupervised learning, self-organizing maps, auto-encoder, neural network, deep neural network, and/or another method. The projection may be applied to at least one of: the training TSCI associated with the at least one event, and/or the current TSCI, for the classifier.

The classifier of the at least one event may be trained based on the projection and the training TSCI associated with the at least one event. The at least one current TSCI may be classified/categorized based on the projection and the current TSCI. The projection may be re-trained using at least one of: the dimension reduction method, and another dimension reduction method, based on at least one of: the training TSCI, at least one current TSCI before retraining the projection, and/or additional training TSCI. The another dimension reduction method may comprise at least one of: principal component analysis (PCA), PCA with different kernels, independent component analysis (ICA), Fisher linear discriminant, vector quantization, supervised learning, unsupervised learning, self-organizing maps, auto-encoder, neural network, deep neural network, and/or yet another method. The classifier of the at least one event may be re-trained based on at least one of: the re-trained projection, the training TSCI associated with the at least one events, and/or at least one current TSCI. The at least one current TSCI may be classified based on: the re-trained projection, the re-trained classifier, and/or the current TSCI.

Each CI may comprise a vector of complex values. Each complex value may be preprocessed to give the magnitude of the complex value. Each CI may be preprocessed to give a vector of non-negative real numbers comprising the magnitude of corresponding complex values. Each training TSCI may be weighted in the training of the projection. The projection may comprise more than one projected components. The projection may comprise at least one most significant projected component. The projection may comprise at least one projected component that may be beneficial for the classifier.

Channel/Channel Information/Venue/Spatial-Temporal Info/Motion/Object

The channel information (CI) may be associated with/may comprise signal strength, signal amplitude, signal phase, spectral power measurement, modem parameters (e.g. used in relation to modulation/demodulation in digital communication systems such as WiFi, 4G/LTE), dynamic beamforming information (including feedback or steering matrices generated by wireless communication devices, according to a standardized process, e.g., IEEE 802.11, or another standard), transfer function components, radio state (e.g. used in digital communication systems to decode digital data, baseband processing state, RF processing state, etc.), measurable variables, sensed data, coarse-grained/fine-grained information of a layer (e.g. physical layer, data link layer, MAC layer, etc.), digital setting, gain setting, RF filter setting, RF front end switch setting, DC offset setting, DC correction setting, IQ compensation setting, effect(s) on the wireless signal by the environment (e.g. venue) during propagation, transformation of an input signal (the wireless signal transmitted by the Type 1 device) to an output signal (the wireless signal received by the Type 2 device), a stable behavior of the environment, a state profile, wireless channel measurements, received signal strength indicator (RSSI), channel state information (CSI), channel impulse response (CIR), channel frequency response (CFR), characteristics of frequency components (e.g. subcarriers) in a bandwidth, channel characteristics, channel filter response, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another channel information. Each CI may be associated with a time stamp, and/or an arrival time. A CSI can be used to equalize/undo/minimize/reduce the multipath channel effect (of the transmission channel) to demodulate a signal similar to the one transmitted by the transmitter through the multipath channel. The CI may be associated with information associated with a frequency band, frequency signature, frequency phase, frequency amplitude, frequency trend, frequency characteristics, frequency-like characteristics, time domain element, frequency domain element, time-frequency domain element, orthogonal decomposition characteristics, and/or non-orthogonal decomposition characteristics of the signal through the channel. The TSCI may be a stream of wireless signals (e.g. CI).

The CI may be preprocessed, processed, postprocessed, stored (e.g. in local memory, portable/mobile memory, removable memory, storage network, cloud memory, in a volatile manner, in a non-volatile manner), retrieved, transmitted and/or received. One or more modem parameters and/or radio state parameters may be held constant. The modem parameters may be applied to a radio subsystem. The modem parameters may represent a radio state. A motion detection signal (e.g. baseband signal, and/or packet decoded/demodulated from the baseband signal, etc.) may be obtained by processing (e.g. down-converting) the first wireless signal (e.g. RF/WiFi/LTE/5G signal) by the radio subsystem using the radio state represented by the stored modem parameters. The modem parameters/radio state may be updated (e.g. using previous modem parameters or previous radio state). Both the previous and updated modem parameters/radio states may be applied in the radio subsystem in the digital communication system. Both the previous and updated modem parameters/radio states may be compared/analyzed/processed/monitored in the task.

The channel information may also be modem parameters (e.g. stored or freshly computed) used to process the wireless signal. The wireless signal may comprise a plurality of probe signals. The same modem parameters may be used to process more than one probe signals. The same modem parameters may also be used to process more than one wireless signals. The modem parameters may comprise parameters that indicate settings or an overall configuration for the operation of a radio subsystem or a baseband subsystem of a wireless sensor device (or both). The modem parameters may include one or more of: a gain setting, an RF filter setting, an RF front end switch setting, a DC offset setting, or an IQ compensation setting for a radio subsystem, or a digital DC correction setting, a digital gain setting, and/or a digital filtering setting (e.g. for a baseband subsystem). The CI may also be associated with information associated with a time period, time signature, timestamp, time amplitude, time phase, time trend, and/or time characteristics of the signal. The CI may be associated with information associated with a time-frequency partition, signature, amplitude, phase, trend, and/or characteristics of the signal. The CI may be associated with a decomposition of the signal. The CI may be associated with information associated with a direction, angle of arrival (AoA), angle of a directional antenna, and/or a phase of the signal through the channel. The CI may be associated with attenuation patterns of the signal through the channel. Each CI may be associated with a Type 1 device and a Type 2 device. Each CI may be associated with an antenna of the Type 1 device and an antenna of the Type 2 device.

The CI may be obtained from a communication hardware (e.g. of Type 2 device, or Type 1 device) that is capable of providing the CI. The communication hardware may be a WiFi-capable chip/IC (integrated circuit), chip compliant with a 802.11 or 802.16 or another wireless/radio standard, next generation WiFi-capable chip, LTE-capable chip, 5G-capable chip, 6G/7G/8G-capable chip, Bluetooth-enabled chip, NFC (near field communication)-enabled chip, BLE (Bluetooth low power)-enabled chip, UWB chip, another communication chip (e.g. Zigbee, WiMax, mesh network), etc. The communication hardware computes the CI and stores the CI in a buffer memory and make the CI available for extraction. The CI may comprise data and/or at least one matrices related to channel state information (CSI). The at least one matrices may be used for channel equalization, and/or beam forming, etc. The channel may be associated with a venue. The attenuation may be due to signal propagation in the venue, signal propagating/reflection/refraction/diffraction through/at/around air (e.g. air of venue), refraction medium/reflection surface such as wall, doors, furniture, obstacles and/or barriers, etc. The attenuation may be due to reflection at surfaces and obstacles (e.g. reflection surface, obstacle) such as floor, ceiling, furniture, fixtures, objects, people, pets, etc. Each CI may be associated with a timestamp. Each CI may comprise N1 components (e.g. N1 frequency domain components in CFR, N1 time domain components in CIR, or N1 decomposition components). Each component may be associated with a component index. Each component may be a real, imaginary, or complex quantity, magnitude, phase, flag, and/or set. Each CI may comprise a vector or matrix of complex numbers, a set of mixed quantities, and/or a multi-dimensional collection of at least one complex numbers.

Components of a TSCI associated with a particular component index may form a respective component time series associated with the respective index. A TSCI may be divided into N1 component time series. Each respective component time series is associated with a respective component index. The characteristics/STI of the motion of the object may be monitored based on the component time series. In one example, one or more ranges of CI components (e.g. one range being from component 11 to component 23, a second range being from component 44 to component 50, and a third range having only one component) may be selected based on some criteria/cost function/signal quality metric (e.g. based on signal-to-noise ratio, and/or interference level) for further processing.

A component-wise characteristic of a component-feature time series of a TSCI may be computed. The component-wise characteristics may be a scalar (e.g. energy) or a function with a domain and a range (e.g. an autocorrelation function, transform, inverse transform). The characteristics/STI of the motion of the object may be monitored based on the component-wise characteristics. A total characteristics (e.g. aggregate characteristics) of the TSCI may be computed based on the component-wise characteristics of each component time series of the TSCI. The total characteristics may be a weighted average of the component-wise characteristics. The characteristics/STI of the motion of the object may be monitored based on the total characteristics. An aggregate quantity may be a weighted average of individual quantities.

The Type 1 device and Type 2 device may support WiFi, WiMax, 3G/beyond 3G, 4G/beyond 4G, LTE, LTE-A, 5G, 6G, 7G, Bluetooth, NFC, BLE, Zigbee, UWB, UMTS, 3GPP, GSM, EDGE, TDMA, FDMA, CDMA, WCDMA, TD-SCDMA, mesh network, proprietary wireless system, IEEE 802.11 standard, 802.15 standard, 802.16 standard, 3GPP standard, and/or another wireless system.

A common wireless system and/or a common wireless channel may be shared by the Type 1 transceiver and/or the at least one Type 2 transceiver. The at least one Type 2 transceiver may transmit respective signal contemporaneously (or: asynchronously, synchronously, sporadically, continuously, repeatedly, concurrently, simultaneously and/or temporarily) using the common wireless system and/or the common wireless channel. The Type 1 transceiver may transmit a signal to the at least one Type 2 transceiver using the common wireless system and/or the common wireless channel.

Each Type 1 device and Type 2 device may have at least one transmitting/receiving antenna. Each CI may be associated with one of the transmitting antenna of the Type 1 device and one of the receiving antenna of the Type 2 device. Each pair of a transmitting antenna and a receiving antenna may be associated with a link, a path, a communication path, signal hardware path, etc. For example, if the Type 1 device has M (e.g. 3) transmitting antennas, and the Type 2 device has N (e.g. 2) receiving antennas, there may be M×N (e.g. 3×2=6) links or paths. Each link or path may be associated with a TSCI.

The at least one TSCI may correspond to various antenna pairs between the Type 1 device and the Type 2 device. The Type 1 device may have at least one antenna. The Type 2 device may also have at least one antenna. Each TSCI may be associated with an antenna of the Type 1 device and an antenna of the Type 2 device. Averaging or weighted averaging over antenna links may be performed. The averaging or weighted averaging may be over the at least one TSCI. The averaging may optionally be performed on a subset of the at least one TSCI corresponding to a subset of the antenna pairs.

Timestamps of CI of a portion of a TSCI may be irregular and may be corrected so that corrected timestamps of time-corrected CI may be uniformly spaced in time. In the case of multiple Type 1 devices and/or multiple Type 2 devices, the corrected timestamp may be with respect to the same or different clock. An original timestamp associated with each of the CI may be determined. The original timestamp may not be uniformly spaced in time. Original timestamps of all CI of the particular portion of the particular TSCI in the current sliding time window may be corrected so that corrected timestamps of time-corrected CI may be uniformly spaced in time.

The characteristics and/or STI (e.g. motion information) may comprise: location, location coordinate, change in location, position (e.g. initial position, new position), position on map, height, horizontal location, vertical location, distance, displacement, speed, acceleration, rotational speed, rotational acceleration, direction, angle of motion, azimuth, direction of motion, rotation, path, deformation, transformation, shrinking, expanding, gait, gait cycle, head motion, repeated motion, periodic motion, pseudo-periodic motion, impulsive motion, sudden motion, fall-down motion, transient motion, behavior, transient behavior, period of motion, frequency of motion, time trend, temporal profile, temporal characteristics, occurrence, change, temporal change, change of CI, change in frequency, change in timing, change of gait cycle, timing, starting time, initiating time, ending time, duration, history of motion, motion type, motion classification, frequency, frequency spectrum, frequency characteristics, presence, absence, proximity, approaching, receding, identity/identifier of the object, composition of the object, head motion rate, head motion direction, mouth-related rate, eye-related rate, breathing rate, heart rate, tidal volume, depth of breath, inhale time, exhale time, inhale time to exhale time ratio, airflow rate, heart heat-to-beat interval, heart rate variability, hand motion rate, hand motion direction, leg motion, body motion, walking rate, hand motion rate, positional characteristics, characteristics associated with movement (e.g. change in position/location) of the object, tool motion, machine motion, complex motion, and/or combination of multiple motions, event, signal statistics, signal dynamics, anomaly, motion statistics, motion parameter, indication of motion detection, motion magnitude, motion phase, similarity score, distance score, Euclidean distance, weighted distance, L_1 norm, L_2 norm, L_k norm for k>2, statistical distance, correlation, correlation indicator, auto-correlation, covariance, auto-covariance, cross-covariance, inner product, outer product, motion signal transformation, motion feature, presence of motion, absence of motion, motion localization, motion identification, motion recognition, presence of object, absence of object, entrance of object, exit of object, a change of object, motion cycle, motion count, gait cycle, motion rhythm, deformation motion, gesture, handwriting, head motion, mouth motion, heart motion, internal organ motion, motion trend, size, length, area, volume, capacity, shape, form, tag, starting/initiating location, ending location, starting/initiating quantity, ending quantity, event, fall-down event, security event, accident event, home event, office event, factory event, warehouse event, manufacturing event, assembly line event, maintenance event, car-related event, navigation event, tracking event, door event, door-open event, door-close event, window event, window-open event, window-close event, repeatable event, one-time event, consumed quantity, unconsumed quantity, state, physical state, health state, well-being state, emotional state, mental state, another event, analytics, output responses, and/or another information. The characteristics and/or STI may be computed/monitored based on a feature computed from a CI or a TSCI (e.g. feature computation/extraction). A static segment or profile (and/or a dynamic segment/profile) may be identified/computed/analyzed/monitored/extracted/obtained/marked/presented/indicated/highlighted/stored/communicated based on an analysis of the feature. The analysis may comprise a motion detection/movement assessment/presence detection. Computational workload may be shared among the Type 1 device, the Type 2 device and another processor.

The Type 1 device and/or Type 2 device may be a local device. The local device may be: a smart phone, smart device, TV, sound bar, set-top box, access point, router, repeater, wireless signal repeater/extender, remote control, speaker, fan, refrigerator, microwave, oven, coffee machine, hot water pot, utensil, table, chair, light, lamp, door lock, camera, microphone, motion sensor, security device, fire hydrant, garage door, switch, power adapter, computer, dongle, computer peripheral, electronic pad, sofa, tile, accessory, home device, vehicle device, office device, building device, manufacturing device, watch, glasses, clock, television, oven, air-conditioner, accessory, utility, appliance, smart machine, smart vehicle, internet-of-thing (IoT) device, internet-enabled device, computer, portable computer, tablet, smart house, smart office, smart building, smart parking lot, smart system, and/or another device.

Each Type 1 device may be associated with a respective identifier (e.g. ID). Each Type 2 device may also be associated with a respective identify (ID). The ID may comprise: numeral, combination of text and numbers, name, password, account, account ID, web link, web address, index to some information, and/or another ID. The ID may be assigned. The ID may be assigned by hardware (e.g. hardwired, via dongle and/or other hardware), software and/or firmware. The ID may be stored (e.g. in database, in memory, in server (e.g. hub device), in the cloud, stored locally, stored remotely, stored permanently, stored temporarily) and may be retrieved. The ID may be associated with at least one record, account, user, household, address, phone number, social security number, customer number, another ID, another identifier, timestamp, and/or collection of data. The ID and/or part of the ID of a Type 1 device may be made available to a Type 2 device. The ID may be used for registration, initialization, communication, identification, verification, detection, recognition, authentication, access control, cloud access, networking, social networking, logging, recording, cataloging, classification, tagging, association, pairing, transaction, electronic transaction, and/or intellectual property control, by the Type 1 device and/or the Type 2 device.

The object may be person, user, subject, passenger, child, older person, baby, sleeping baby, baby in vehicle, patient, worker, high-value worker, expert, specialist, waiter, customer in mall, traveler in airport/train station/bus terminal/shipping terminals, staff/worker/customer service personnel in factory/mall/supermarket/office/workplace, serviceman in sewage/air ventilation system/lift well, lifts in lift wells, elevator, inmate, people to be tracked/monitored, animal, plant, living object, pet, dog, cat, smart phone, phone accessory, computer, tablet, portable computer, dongle, computing accessory, networked devices, WiFi devices, IoT devices, smart watch, smart glasses, smart devices, speaker, keys, smart key, wallet, purse, handbag, backpack, goods, cargo, luggage, equipment, motor, machine, air conditioner, fan, air conditioning equipment, light fixture, moveable light, television, camera, audio and/or video equipment, stationary, surveillance equipment, parts, signage, tool, cart, ticket, parking ticket, toll ticket, airplane ticket, credit card, plastic card, access card, food packaging, utensil, table, chair, cleaning equipment/tool, vehicle, car, cars in parking facilities, merchandise in warehouse/store/supermarket/distribution center, boat, bicycle, airplane, drone, remote control car/plane/boat, robot, manufacturing device, assembly line, material/unfinished part/robot/wagon/transports on factory floor, object to be tracked in airport/shopping mart/supermarket, non-object, absence of an object, presence of an object, object with form, object with changing form, object with no form, mass of fluid, mass of liquid, mass of gas/smoke, fire, flame, electromagnetic (EM) source, EM medium, and/or another object.

The object itself may be communicatively coupled with some network, such as WiFi, MiFi, 3G/4G/LTE/5G/6G/7G, Bluetooth, NFC, BLE, WiMax, Zigbee, UMTS, 3GPP, GSM, EDGE, TDMA, FDMA, CDMA, WCDMA, TD-SCDMA, mesh network, adhoc network, and/or other network. The object itself may be bulky with AC power supply, but is moved during installation, cleaning, maintenance, renovation, etc. It may also be installed in moveable platform such as lift, pad, movable, platform, elevator, conveyor belt, robot, drone, forklift, car, boat, vehicle, etc. The object may have multiple parts, each part with different movement (e.g. change in position/location). For example, the object may be a person walking forward. While walking, his left hand and right hand may move in different direction, with different instantaneous speed, acceleration, motion, etc.

The wireless transmitter (e.g. Type 1 device), the wireless receiver (e.g. Type 2 device), another wireless transmitter and/or another wireless receiver may move with the object and/or another object (e.g. in prior movement, current movement and/or future movement. They may be communicatively coupled to one or more nearby device. They may transmit TSCI and/or information associated with the TSCI to the nearby device, and/or each other. They may be with the nearby device. The wireless transmitter and/or the wireless receiver may be part of a small (e.g. coin-size, cigarette box size, or even smaller), light-weight portable device. The portable device may be wirelessly coupled with a nearby device.

The nearby device may be smart phone, iPhone, Android phone, smart device, smart appliance, smart vehicle, smart gadget, smart TV, smart refrigerator, smart speaker, smart watch, smart glasses, smart pad, iPad, computer, wearable computer, notebook computer, gateway. The nearby device may be connected to a cloud server, local server (e.g. hub device) and/or other server via internet, wired internet connection and/or wireless internet connection. The nearby device may be portable. The portable device, the nearby device, a local server (e.g. hub device) and/or a cloud server may share the computation and/or storage for a task (e.g. obtain TSCI, determine characteristics/STI of the object associated with the movement (e.g. change in position/location) of the object, computation of time series of power (e.g. signal strength) information, determining/computing the particular function, searching for local extremum, classification, identifying particular value of time offset, denoising, processing, simplification, cleaning, wireless smart sensing task, extract CI from signal, switching, segmentation, estimate trajectory/path/track, process the map, processing trajectory/path/track based on environment models/constraints/limitations, correction, corrective adjustment, adjustment, map-based (or model-based) correction, detecting error, checking for boundary hitting, thresholding) and information (e.g. TSCI). The nearby device may/may not move with the object. The nearby device may be portable/not portable/moveable/non-moveable. The nearby device may use battery power, solar power, AC power and/or other power source. The nearby device may have replaceable/non-replaceable battery, and/or rechargeable/non-rechargeable battery. The nearby device may be similar to the object. The nearby device may have identical (and/or similar) hardware and/or software to the object. The nearby device may be a smart device, network enabled device, device with connection to WiFi/3G/4G/5G/6G/Zigbee/Bluetooth/NFC/UMTS/3GPP/GSM/EDGE/TDMA/FDMA/CDMA/WCDMA/TD-SCDMA/adhoc network/other network, smart speaker, smart watch, smart clock, smart appliance, smart machine, smart equipment, smart tool, smart vehicle, internet-of-thing (IoT) device, internet-enabled device, computer, portable computer, tablet, and another device. The nearby device and/or at least one processor associated with the wireless receiver, the wireless transmitter, the another wireless receiver, the another wireless transmitter and/or a cloud server (in the cloud) may determine the initial STI of the object. Two or more of them may determine the initial spatial-temporal info jointly. Two or more of them may share intermediate information in the determination of the initial STI (e.g. initial position).

In one example, the wireless transmitter (e.g. Type 1 device, or Tracker Bot) may move with the object. The wireless transmitter may send the signal to the wireless receiver (e.g. Type 2 device, or Origin Register) or determining the initial STI (e.g. initial position) of the object. The wireless transmitter may also send the signal and/or another signal to another wireless receiver (e.g. another Type 2 device, or another Origin Register) for the monitoring of the motion (spatial-temporal info) of the object. The wireless receiver may also receive the signal and/or another signal from the wireless transmitter and/or the another wireless transmitter for monitoring the motion of the object. The location of the wireless receiver and/or the another wireless receiver may be known. In another example, the wireless receiver (e.g. Type 2 device, or Tracker Bot) may move with the object. The wireless receiver may receive the signal transmitted from the wireless transmitter (e.g. Type 1 device, or Origin Register) for determining the initial spatial-temporal info (e.g. initial position) of the object. The wireless receiver may also receive the signal and/or another signal from another wireless transmitter (e.g. another Type 1 device, or another Origin Register) for the monitoring of the current motion (e.g. spatial-temporal info) of the object. The wireless transmitter may also transmit the signal and/or another signal to the wireless receiver and/or the another wireless receiver (e.g. another Type 2 device, or another Tracker Bot) for monitoring the motion of the object. The location of the wireless transmitter and/or the another wireless transmitter may be known.

The venue may be a space such as a sensing area, room, house, office, property, workplace, hallway, walkway, lift, lift well, escalator, elevator, sewage system, air ventilations system, staircase, gathering area, duct, air duct, pipe, tube, enclosed space, enclosed structure, semi-enclosed structure, enclosed area, area with at least one wall, plant, machine, engine, structure with wood, structure with glass, structure with metal, structure with walls, structure with doors, structure with gaps, structure with reflection surface, structure with fluid, building, roof top, store, factory, assembly line, hotel room, museum, classroom, school, university, government building, warehouse, garage, mall, airport, train station, bus terminal, hub, transportation hub, shipping terminal, government facility, public facility, school, university, entertainment facility, recreational facility, hospital, pediatric/neonatal wards, seniors home, elderly care facility, geriatric facility, community center, stadium, playground, park, field, sports facility, swimming facility, track and/or field, basketball court, tennis court, soccer stadium, baseball stadium, gymnasium, hall, garage, shopping mart, mall, supermarket, manufacturing facility, parking facility, construction site, mining facility, transportation facility, highway, road, valley, forest, wood, terrain, landscape, den, patio, land, path, amusement park, urban area, rural area, suburban area, metropolitan area, garden, square, plaza, music hall, downtown facility, over-air facility, semi-open facility, closed area, train platform, train station, distribution center, warehouse, store, distribution center, storage facility, underground facility, space (e.g. above ground, outer-space) facility, floating facility, cavern, tunnel facility, indoor facility, open-air facility, outdoor facility with some walls/doors/reflective barriers, open facility, semi-open facility, car, truck, bus, van, container, ship/boat, submersible, train, tram, airplane, vehicle, mobile home, cave, tunnel, pipe, channel, metropolitan area, downtown area with relatively tall buildings, valley, well, duct, pathway, gas line, oil line, water pipe, network of interconnecting pathways/alleys/roads/tubes/cavities/caves/pipe-like structure/air space/fluid space, human body, animal body, body cavity, organ, bone, teeth, soft tissue, hard tissue, rigid tissue, non-rigid tissue, blood/body fluid vessel, windpipe, air duct, den, etc. The venue may be indoor space, outdoor space, The venue may include both the inside and outside of the space. For example, the venue may include both the inside of a building and the outside of the building. For example, the venue can be a building that has one floor or multiple floors, and a portion of the building can be underground. The shape of the building can be, e.g., round, square, rectangular, triangle, or irregular-shaped. These are merely examples. The disclosure can be used to detect events in other types of venue or spaces.

The wireless transmitter (e.g. Type 1 device) and/or the wireless receiver (e.g. Type 2 device) may be embedded in a portable device (e.g. a module, or a device with the module) that may move with the object (e.g. in prior movement and/or current movement). The portable device may be communicatively coupled with the object using a wired connection (e.g. through USB, microUSB, Firewire, HDMI, serial port, parallel port, and other connectors) and/or a connection (e.g. Bluetooth, Bluetooth Low Energy (BLE), WiFi, LTE, NFC, ZigBee). The portable device may be a lightweight device. The portable may be powered by battery, rechargeable battery and/or AC power. The portable device may be very small (e.g. at sub-millimeter scale and/or sub-centimeter scale), and/or small (e.g. coin-size, card-size, pocket-size, or larger). The portable device may be large, sizable, and/or bulky (e.g. heavy machinery to be installed). The portable device may be a WiFi hotspot, access point, mobile WiFi (MiFi), dongle with USB/micro USB/Firewire/other connector, smartphone, portable computer, computer, tablet, smart device, internet-of-thing (IoT) device, WiFi-enabled device, LTE-enabled device, a smart watch, smart glass, smart mirror, smart antenna, smart battery, smart light, smart pen, smart ring, smart door, smart window, smart clock, small battery, smart wallet, smart belt, smart handbag, smart clothing/garment, smart ornament, smart packaging, smart paper/book/magazine/poster/printed matter/signage/display/lighted system/lighting system, smart key/tool, smart bracelet/chain/necklace/wearable/accessory, smart pad/cushion, smart tile/block/brick/building material/other material, smart garbage can/waste container, smart food carriage/storage, smart ball/racket, smart chair/sofa/bed, smart shoe/footwear/carpet/mat/shoe rack, smart glove/hand wear/ring/hand ware, smart hat/headwear/makeup/sticker/tattoo, smart mirror, smart toy, smart pill, smart utensil, smart bottle/food container, smart tool, smart device, IoT device, WiFi enabled device, network enabled device, 3G/4G/5G/6G enabled device, UMTS devices, 3GPP devices, GSM devices, EDGE devices, TDMA devices, FDMA devices, CDMA devices, WCDMA devices, TD-SCDMA devices, embeddable device, implantable device, air conditioner, refrigerator, heater, furnace, furniture, oven, cooking device, television/set-top box (STB)/DVD player/audio player/video player/remote control, hi-fi, audio device, speaker, lamp/light, wall, door, window, roof, roof tile/shingle/structure/attic structure/device/feature/installation/fixtures, lawn mower/garden tools/yard tools/mechanics tools/garage tools/, garbage can/container, 20-ft/40-ft container, storage container, factory/manufacturing/production device, repair tools, fluid container, machine, machinery to be installed, vehicle, cart, wagon, warehouse vehicle, car, bicycle, motorcycle, boat, vessel, airplane, basket/box/bag/bucket/container, smart plate/cup/bowl/pot/mat/utensils/kitchen tools/kitchen devices/kitchen accessories/cabinets/tables/chairs/tiles/lights/water pipes/taps/gas range/oven/dishwashing machine/etc. The portable device may have a battery that may be replaceable, irreplaceable, rechargeable, and/or non-rechargeable. The portable device may be wirelessly charged. The portable device may be a smart payment card. The portable device may be a payment card used in parking lots, highways, entertainment parks, or other venues/facilities that need payment. The portable device may have an identity (ID)/identifier as described above.

An event may be monitored based on the TSCI. The event may be an object related event, such as fall-down of the object (e.g. an person and/or a sick person), rotation, hesitation, pause, impact (e.g. a person hitting a sandbag, door, window, bed, chair, table, desk, cabinet, box, another person, animal, bird, fly, table, chair, ball, bowling ball, tennis ball, football, soccer ball, baseball, basketball, volley ball), two-body action (e.g. a person letting go a balloon, catching a fish, molding a clay, writing a paper, person typing on a computer), car moving in a garage, person carrying a smart phone and walking around an airport/mall/government building/office/etc., autonomous moveable object/machine moving around (e.g. vacuum cleaner, utility vehicle, car, drone, self-driving car).

The task or the wireless smart sensing task may comprise: object detection, presence detection, proximity detection, object recognition, activity recognition, object verification, object counting, daily activity monitoring, well-being monitoring, vital sign monitoring, health condition monitoring, baby monitoring, elderly monitoring, sleep monitoring, sleep stage monitoring, walking monitoring, exercise monitoring, tool detection, tool recognition, tool verification, patient detection, patient monitoring, patient verification, machine detection, machine recognition, machine verification, human detection, human recognition, human verification, baby detection, baby recognition, baby verification, human breathing detection, human breathing recognition, human breathing estimation, human breathing verification, human heart beat detection, human heart beat recognition, human heart beat estimation, human heart beat verification, fall-down detection, fall-down recognition, fall-down estimation, fall-down verification, emotion detection, emotion recognition, emotion estimation, emotion verification, motion detection, motion degree estimation, motion recognition, motion estimation, motion verification, periodic motion detection, periodic motion recognition, periodic motion estimation, periodic motion verification, repeated motion detection, repeated motion recognition, repeated motion estimation, repeated motion verification, stationary motion detection, stationary motion recognition, stationary motion estimation, stationary motion verification, cyclo-stationary motion detection, cyclo-stationary motion recognition, cyclo-stationary motion estimation, cyclo-stationary motion verification, transient motion detection, transient motion recognition, transient motion estimation, transient motion verification, trend detection, trend recognition, trend estimation, trend verification, breathing detection, breathing recognition, breathing estimation, breathing estimation, human biometrics detection, human biometric recognition, human biometrics estimation, human biometrics verification, environment informatics detection, environment informatics recognition, environment informatics estimation, environment informatics verification, gait detection, gait recognition, gait estimation, gait verification, gesture detection, gesture recognition, gesture estimation, gesture verification, machine learning, supervised learning, unsupervised learning, semi-supervised learning, clustering, feature extraction, featuring training, principal component analysis, eigen-decomposition, frequency decomposition, time decomposition, time-frequency decomposition, functional decomposition, other decomposition, training, discriminative training, supervised training, unsupervised training, semi-supervised training, neural network, sudden motion detection, fall-down detection, danger detection, life-threat detection, regular motion detection, stationary motion detection, cyclo-stationary motion detection, intrusion detection, suspicious motion detection, security, safety monitoring, navigation, guidance, map-based processing, map-based correction, model-based processing/correction, irregularity detection, locationing, room sensing, tracking, multiple object tracking, indoor tracking, indoor position, indoor navigation, energy management, power transfer, wireless power transfer, object counting, car tracking in parking garage, activating a device/system (e.g. security system, access system, alarm, siren, speaker, television, entertaining system, camera, heater/air-conditioning (HVAC) system, ventilation system, lighting system, gaming system, coffee machine, cooking device, cleaning device, housekeeping device), geometry estimation, augmented reality, wireless communication, data communication, signal broadcasting, networking, coordination, administration, encryption, protection, cloud computing, other processing and/or other task. The task may be performed by the Type 1 device, the Type 2 device, another Type 1 device, another Type 2 device, a nearby device, a local server (e.g. hub device), edge server, a cloud server, and/or another device. The task may be based on TSCI between any pair of Type 1 device and Type 2 device. A Type 2 device may be a Type 1 device, and vice versa. A Type 2 device may play/perform the role (e.g. functionality) of Type 1 device temporarily, continuously, sporadically, simultaneously, and/or contemporaneously, and vice versa. A first part of the task may comprise at least one of: preprocessing, processing, signal conditioning, signal processing, post-processing, processing sporadically/continuously/simultaneously/contemporaneously/dynamically/adaptive/on-demand/as-needed, calibrating, denoising, feature extraction, coding, encryption, transformation, mapping, motion detection, motion estimation, motion change detection, motion pattern detection, motion pattern estimation, motion pattern recognition, vital sign detection, vital sign estimation, vital sign recognition, periodic motion detection, periodic motion estimation, repeated motion detection/estimation, breathing rate detection, breathing rate estimation, breathing pattern detection, breathing pattern estimation, breathing pattern recognition, heart beat detection, heart beat estimation, heart pattern detection, heart pattern estimation, heart pattern recognition, gesture detection, gesture estimation, gesture recognition, speed detection, speed estimation, object locationing, object tracking, navigation, acceleration estimation, acceleration detection, fall-down detection, change detection, intruder (and/or illegal action) detection, baby detection, baby monitoring, patient monitoring, object recognition, wireless power transfer, and/or wireless charging.

A second part of the task may comprise at least one of: a smart home task, smart office task, smart building task, smart factory task (e.g. manufacturing using a machine or an assembly line), smart internet-of-thing (IoT) task, smart system task, smart home operation, smart office operation, smart building operation, smart manufacturing operation (e.g. moving supplies/parts/raw material to a machine/an assembly line), IoT operation, smart system operation, turning on a light, turning off the light, controlling the light in at least one of: a room, region, and/or the venue, playing a sound clip, playing the sound clip in at least one of: the room, the region, and/or the venue, playing the sound clip of at least one of: a welcome, greeting, farewell, first message, and/or a second message associated with the first part of the task, turning on an appliance, turning off the appliance, controlling the appliance in at least one of: the room, the region, and/or the venue, turning on an electrical system, turning off the electrical system, controlling the electrical system in at least one of: the room, the region, and/or the venue, turning on a security system, turning off the security system, controlling the security system in at least one of: the room, the region, and/or the venue, turning on a mechanical system, turning off a mechanical system, controlling the mechanical system in at least one of: the room, the region, and/or the venue, and/or controlling at least one of: an air conditioning system, heating system, ventilation system, lighting system, heating device, stove, entertainment system, door, fence, window, garage, computer system, networked device, networked system, home appliance, office equipment, lighting device, robot (e.g. robotic arm), smart vehicle, smart machine, assembly line, smart device, internet-of-thing (IoT) device, smart home device, and/or a smart office device.

The task may include: detect a user returning home, detect a user leaving home, detect a user moving from one room to another, detect/control/lock/unlock/open/close/partially open a window/door/garage door/blind/curtain/panel/solar panel/sun shade, detect a pet, detect/monitor a user doing something (e.g. sleeping on sofa, sleeping in bedroom, running on treadmill, cooking, sitting on sofa, watching TV, eating in kitchen, eating in dining room, going upstairs/downstairs, going outside/coming back, in the rest room), monitor/detect location of a user/pet, do something (e.g. send a message, notify/report to someone) automatically upon detection, do something for the user automatically upon detecting the user, turn on/off/dim a light, turn on/off music/radio/home entertainment system, turn on/off/adjust/control TV/HiFi/set-top-box (STB)/home entertainment system/smart speaker/smart device, turn on/off/adjust air conditioning system, turn on/off/adjust ventilation system, turn on/off/adjust heating system, adjust/control curtains/light shades, turn on/off/wake a computer, turn on/off/pre-heat/control coffee machine/hot water pot, turn on/off/control/preheat cooker/oven/microwave oven/another cooking device, check/adjust temperature, check weather forecast, check telephone message box, check mail, do a system check, control/adjust a system, check/control/arm/disarm security system/baby monitor, check/control refrigerator, give a report (e.g. through a speaker such as Google home, Amazon Echo, on a display/screen, via a webpage/email/messaging system/notification system).

For example, when a user arrives home in his car, the task may be to, automatically, detect the user or his car approaching, open the garage door upon detection, turn on the driveway/garage light as the user approaches the garage, turn on air conditioner/heater/fan, etc. As the user enters the house, the task may be to, automatically, turn on the entrance light, turn off driveway/garage light, play a greeting message to welcome the user, turn on the music, turn on the radio and tuning to the user's favorite radio news channel, open the curtain/blind, monitor the user's mood, adjust the lighting and sound environment according to the user's mood or the current/imminent event (e.g. do romantic lighting and music because the user is scheduled to eat dinner with girlfriend in 1 hour) on the user's daily calendar, warm the food in microwave that the user prepared in the morning, do a diagnostic check of all systems in the house, check weather forecast for tomorrow's work, check news of interest to the user, check user's calendar and to-do list and play reminder, check telephone answer system/messaging system/email and give a verbal report using dialog system/speech synthesis, remind (e.g. using audible tool such as speakers/HiFi/ speech synthesis/sound/voice/music/song/sound field/background sound field/dialog system, using visual tool such as TV/entertainment system/computer/notebook/smart pad/display/light/color/brightness/patterns/symbols, using haptic tool/virtual reality tool/gesture/tool, using a smart device/appliance/material/furniture/fixture, using web tool/server/hub device/cloud server/fog server/edge server/home network/mesh network, using messaging tool/notification tool/communication tool/scheduling tool/email, using user interface/GUI, using scent/smell/fragrance/taste, using neural tool/nervous system tool, using a combination) the user of his mother's birthday and to call her, prepare a report, and give the report (e.g. using a tool for reminding as discussed above). The task may turn on the air conditioner/heater/ventilation system in advance, or adjust temperature setting of smart thermostat in advance, etc. As the user moves from the entrance to the living room, the task may be to turn on the living room light, open the living room curtain, open the window, turn off the entrance light behind the user, turn on the TV and set-top box, set TV to the user's favorite channel, adjust an appliance according to the user's preference and conditions/states (e.g. adjust lighting and choose/play music to build a romantic atmosphere), etc.

Another example may be: When the user wakes up in the morning, the task may be to detect the user moving around in the bedroom, open the blind/curtain, open the window, turn off the alarm clock, adjust indoor temperature from night-time temperature profile to day-time temperature profile, turn on the bedroom light, turn on the restroom light as the user approaches the restroom, check radio or streaming channel and play morning news, turn on the coffee machine and preheat the water, turn off security system, etc. When the user walks from bedroom to kitchen, the task may be to turn on the kitchen and hallway lights, turn off the bedroom and restroom lights, move the music/message/reminder from the bedroom to the kitchen, turn on the kitchen TV, change TV to morning news channel, lower the kitchen blind and open the kitchen window to bring in fresh air, unlock backdoor for the user to check the backyard, adjust temperature setting for the kitchen, etc. Another example may be: When the user leaves home for work, the task may be to detect the user leaving, play a farewell and/or have-a-good-day message, open/close garage door, turn on/off garage light and driveway light, turn off/dim lights to save energy (just in case the user forgets), close/lock all windows/doors (just in case the user forgets), turn off appliance (especially stove, oven, microwave oven), turn on/arm the home security system to guard the home against any intruder, adjust air conditioning/heating/ventilation systems to "away-from-home" profile to save energy, send alerts/reports/updates to the user's smart phone, etc.

A motion may comprise at least one of: a no-motion, resting motion, non-moving motion, movement, change in position/location, deterministic motion, transient motion, fall-down motion, repeating motion, periodic motion, pseudo-periodic motion, periodic/repeated motion associated with breathing, periodic/repeated motion associated with heartbeat, periodic/repeated motion associated with living object, periodic/repeated motion associated with machine, periodic/repeated motion associated with man-made object, periodic/repeated motion associated with nature, complex motion with transient element and periodic element, repetitive motion, non-deterministic motion, probabilistic motion, chaotic motion, random motion, complex motion with non-deterministic element and deterministic element, stationary random motion, pseudo-stationary random motion, cyclo-stationary random motion, non-stationary random motion, stationary random motion with periodic autocorrelation function (ACF), random motion with periodic ACF for period of time, random motion that is pseudo-stationary for a period of time, random motion of which an instantaneous ACF has a pseudo-periodic/repeating element for a period of time, machine motion, mechanical motion, vehicle motion, drone motion, air-related motion, wind-related motion, weather-related motion, water-related motion, fluid-related motion, ground-related motion, change in electro-magnetic characteristics, subsurface motion, seismic motion, plant motion, animal motion, human motion, normal motion, abnormal motion, dangerous motion, warning motion, suspicious motion, rain, fire, flood, tsunami, explosion, collision, imminent collision, human body motion, head motion, facial motion, eye motion, mouth motion, tongue motion, neck motion, finger motion, hand motion, arm motion, shoulder motion, body motion, chest motion, abdominal motion, hip motion, leg motion, foot motion, body joint motion, knee motion, elbow motion, upper body motion, lower body motion, skin motion, below-skin motion, subcutaneous tissue motion, blood vessel motion, intravenous motion, organ motion, heart motion, lung motion, stomach motion, intestine motion, bowel motion, eating motion, breathing motion, facial expression, eye expression, mouth expression, talking motion, singing motion, eating motion, gesture, hand gesture, arm gesture, keystroke, typing stroke, user-interface gesture, man-machine interaction, gait, dancing movement, coordinated movement, and/or coordinated body movement.

The heterogeneous IC of the Type 1 device and/or any Type 2 receiver may comprise low-noise amplifier (LNA), power amplifier, transmit-receive switch, media access controller, baseband radio, 2.4 GHz radio, 3.65 GHz radio, 4.9 GHz radio, 5 GHz radio, 5.9 GHz radio, below 6 GHz radio, below 60 GHz radio and/or another radio. The heterogeneous IC may comprise a processor, a memory communicatively coupled with the processor, and a set of instructions stored in the memory to be executed by the processor. The IC and/or any processor may comprise at least one of: general purpose processor, special purpose processor, microprocessor, multi-processor, multi-core processor, parallel processor, CISC processor, RISC processor, microcontroller, central processing unit (CPU), graphical processor unit (GPU), digital signal processor (DSP), application specific integrated circuit (ASIC), field programmable gate array (FPGA), embedded processor (e.g. ARM), logic circuit, other programmable logic device, discrete logic, and/or a combination. The heterogeneous IC may support broadband network, wireless network, mobile network, mesh network, cellular network, wireless local area network (WLAN), wide area network (WAN), and metropolitan area network (MAN), WLAN standard, WiFi, LTE, LTE-A, LTE-U, 802.11 standard, 802.11a, 802.11b, 802.11 g, 802.11n, 802.11ac, 802.11ad, 802.11af, 802.11ah, 802.1 lax, 802.1 lay, mesh network standard, 802.15 standard, 802.16 standard, cellular network standard, 3G, 3.5G, 4G, beyond 4G, 4.5G, 5G, 6G, 7G, 8G, 9G, UMTS, 3GPP, GSM, EDGE, TDMA, FDMA, CDMA, WCDMA, TD-SCDMA, Bluetooth, Bluetooth Low-Energy (BLE), NFC, Zigbee, WiMax, and/or another wireless network protocol.

The processor may comprise general purpose processor, special purpose processor, microprocessor, microcontroller, embedded processor, digital signal processor, central processing unit (CPU), graphical processing unit (GPU), multi-processor, multi-core processor, and/or processor with graphics capability, and/or a combination. The memory may be volatile, non-volatile, random access memory (RAM), Read Only Memory (ROM), Electrically Programmable ROM (EPROM), Electrically Erasable Programmable ROM (EEPROM), hard disk, flash memory, CD-ROM, DVD-ROM, magnetic storage, optical storage, organic storage, storage system, storage network, network storage, cloud storage, edge storage, local storage, external storage, internal storage, or other form of non-transitory storage medium known in the art. The set of instructions (machine executable code) corresponding to the method steps may be embodied directly in hardware, in software, in firmware, or in combinations thereof. The set of instructions may be embedded, pre-loaded, loaded upon boot up, loaded on the fly, loaded on demand, pre-installed, installed, and/or downloaded.

The presentation may be a presentation in an audio-visual way (e.g. using combination of visual, graphics, text, symbols, color, shades, video, animation, sound, speech, audio, etc.), graphical way (e.g. using GUI, animation, video), textual way (e.g. webpage with text, message, animated text), symbolic way (e.g. emoticon, signs, hand gesture), or mechanical way (e.g. vibration, actuator movement, haptics, etc.).

Basic Computation

Computational workload associated with the method is shared among the processor, the Type 1 heterogeneous wireless device, the Type 2 heterogeneous wireless device, a local server (e.g. hub device), a cloud server, and another processor.

An operation, pre-processing, processing and/or postprocessing may be applied to data (e.g. TSCI, autocorrelation, features of TSCI). An operation may be preprocessing, processing and/or postprocessing. The preprocessing, processing and/or postprocessing may be an operation. An operation may comprise preprocessing, processing, postprocessing, scaling, computing a confidence factor, computing a line-of-sight (LOS) quantity, computing a non-LOS (NLOS) quantity, a quantity comprising LOS and NLOS, computing a single link (e.g. path, communication path, link between a transmitting antenna and a receiving antenna) quantity, computing a quantity comprising multiple links, computing a function of the operands, filtering, linear filtering, nonlinear filtering, folding, grouping, energy computation, lowpass filtering, bandpass filtering, highpass filtering, median filtering, rank filtering, quartile filtering, percentile filtering, mode filtering, finite impulse response (FIR) filtering, infinite impulse response (IIR) filtering, moving average (MA) filtering, autoregressive (AR) filtering, autoregressive moving averaging (ARMA) filtering, selective filtering, adaptive filtering, interpolation, decimation, subsampling, upsampling, resampling, time correction, time base correction, phase correction, magnitude correction, phase cleaning, magnitude cleaning, matched filtering, enhancement, restoration, denoising, smoothing, signal conditioning, enhancement, restoration, spectral analysis, linear transform, nonlinear transform, inverse transform, frequency transform, inverse frequency transform, Fourier transform (FT), discrete time FT (DTFT), discrete FT (DFT), fast FT (FFT), wavelet transform, Laplace transform, Hilbert transform, Hadamard transform, trigonometric transform, sine transform, cosine transform, DCT, power-of-2 transform, sparse transform, graph-based transform, graph signal processing, fast transform, a transform combined with zero padding, cyclic padding, padding, zero padding, feature extraction, decomposition, projection, orthogonal projection, non-orthogonal projection, over-complete projection, eigen-decomposition, singular value decomposition (SVD), principle component analysis (PCA), independent component analysis (ICA), grouping, sorting, thresholding, soft thresholding, hard thresholding, clipping, soft clipping, first derivative, second order derivative, high order derivative, convolution, multiplication, division, addition, subtraction, integration, maximization, minimization, least mean square error, recursive least square, constrained least square, batch least square, least absolute error, least mean square deviation, least absolute deviation, local maximization, local minimization, optimization of a cost function, neural network, recognition, labeling, training, clustering, machine learning, supervised learning, unsupervised learning, semi-supervised learning, comparison with another TSCI, similarity score computation, quantization, vector quantization, matching pursuit, compression, encryption, coding, storing, transmitting, normalization, temporal normalization, frequency domain normalization, classification, clustering, labeling, tagging, learning, detection, estimation, learning network, mapping, remapping, expansion, storing, retrieving, transmitting, receiving, representing, merging, combining, splitting, tracking, monitoring, matched filtering, Kalman filtering, particle filter, intrapolation, extrapolation, histogram estimation, importance sampling, Monte Carlo sampling, compressive sensing, representing, merging, combining, splitting, scrambling, error protection, forward error correction, doing nothing, time varying processing, conditioning averaging, weighted averaging, arithmetic mean, geometric mean, harmonic mean, averaging over selected frequency, averaging over antenna links, logical operation, permutation, combination, sorting, AND, OR, XOR, union, intersection, vector addition, vector subtraction, vector multiplication, vector division, inverse, norm, distance, and/or another operation. The operation may be the preprocessing, processing, and/or post-processing. Operations may be applied jointly on multiple time series or functions.

The function (e.g. function of operands) may comprise: scalar function, vector function, discrete function, continuous function, polynomial function, characteristics, feature, magnitude, phase, exponential function, logarithmic function, trigonometric function, transcendental function, logical function, linear function, algebraic function, nonlinear function, piecewise linear function, real function, complex function, vector-valued function, inverse function, derivative of function, integration of function, circular function, function of another function, one-to-one function, one-to-many function, many-to-one function, many-to-many function, zero crossing, absolute function, indicator function, mean, mode, median, range, statistics, histogram, variance, standard deviation, measure of variation, spread, dispersion, deviation, divergence, range, interquartile range, total variation, absolute deviation, total deviation, arithmetic mean, geometric mean, harmonic mean, trimmed mean, percentile, square, cube, root, power, sine, cosine, tangent, cotangent, secant, cosecant, elliptical function, parabolic function, hyperbolic function, game function, zeta function, absolute value, thresholding, limiting function, floor function, rounding function, sign function, quantization, piecewise constant function, composite function, function of function, time function processed with an operation (e.g. filtering), probabilistic function, stochastic function, random function, ergodic function, stationary function, deterministic function, periodic function, repeated function, transformation, frequency transform, inverse frequency transform, discrete time transform, Laplace transform, Hilbert transform, sine transform, cosine transform, triangular transform, wavelet transform, integer transform, power-of-2 transform, sparse transform, projection, decomposition, principle component analysis (PCA), independent component analysis (ICA), neural network, feature extraction, moving function, function of moving window of neighboring items of time series, filtering function, convolution, mean function, histogram, variance/standard deviation function, statistical function, short-time transform, discrete transform, discrete Fourier transform, discrete cosine transform, discrete sine transform, Hadamard transform, eigen-decomposition, eigenvalue, singular value decomposition (SVD), singular value, orthogonal decomposition, matching pursuit, sparse transform, sparse approximation, any decomposition, graph-based processing, graph-based transform, graph signal processing, classification, identifying a class/group/category, labeling, learning, machine learning, detection, estimation, feature extraction, learning network, feature extraction, denoising, signal enhancement, coding, encryption, mapping, remapping, vector quantization, lowpass filtering, highpass filtering, bandpass filtering, matched filtering, Kalman filtering, preprocessing, postprocessing, particle filter, FIR filtering, IIR filtering, autoregressive (AR) filtering, adaptive filtering, first order derivative, high order derivative, integration, zero crossing, smoothing, median filtering, mode filtering, sampling, random sampling, resampling function, downsampling, down-converting, upsampling, up-converting, interpolation, extrapolation, importance sampling, Monte Carlo sampling, compressive sensing, statistics, short term statistics, long term statistics, autocorrelation function, cross correlation, moment generating function, time averaging, weighted averaging, special function, Bessel function, error function, complementary error function, Beta function, Gamma function, integral function, Gaussian function, Poisson function, etc.

Machine learning, training, discriminative training, deep learning, neural network, continuous time processing, distributed computing, distributed storage, acceleration using GPU/DSP/coprocessor/multicore/multiprocessing may be applied to a step (or each step) of this disclosure.

A frequency transform may include Fourier transform, Laplace transform, Hadamard transform, Hilbert transform, sine transform, cosine transform, triangular transform, wavelet transform, integer transform, power-of-2 transform, combined zero padding and transform, Fourier transform with zero padding, and/or another transform. Fast versions and/or approximated versions of the transform may be performed. The transform may be performed using floating point, and/or fixed point arithmetic.

An inverse frequency transform may include inverse Fourier transform, inverse Laplace transform, inverse Hadamard transform, inverse Hilbert transform, inverse sine transform, inverse cosine transform, inverse triangular transform, inverse wavelet transform, inverse integer transform, inverse power-of-2 transform, combined zero padding and transform, inverse Fourier transform with zero padding, and/or another transform. Fast versions and/or approximated versions of the transform may be performed. The transform may be performed using floating point, and/or fixed point arithmetic.

A quantity/feature from a TSCI may be computed. The quantity may comprise statistic of at least one of: motion, location, map coordinate, height, speed, acceleration, movement angle, rotation, size, volume, time trend, pattern, one-time pattern, repeating pattern, evolving pattern, time pattern, mutually excluding patterns, related/correlated patterns, cause-and-effect, correlation, short-term/long-term correlation, tendency, inclination, statistics, typical behavior, atypical behavior, time trend, time profile, periodic motion, repeated motion, repetition, tendency, change, abrupt change, gradual change, frequency, transient, breathing, gait, action, event, suspicious event, dangerous event, alarming event, warning, belief, proximity, collision, power, signal, signal power, signal strength, signal intensity, received signal strength indicator (RSSI), signal amplitude, signal phase, signal frequency component, signal frequency band component, channel state information (CSI), map, time, frequency, time-frequency, decomposition, orthogonal decomposition, non-orthogonal decomposition, tracking, breathing, heart beat, statistical parameters, cardiopulmonary statistics/analytics (e.g. output responses), daily activity statistics/analytics, chronic disease statistics/analytics, medical statistics/analytics, an early (or instantaneous or contemporaneous or delayed) indication/suggestion/sign/indicator/verifier/detection/symptom of a disease/condition/situation, biometric, baby, patient, machine, device, temperature, vehicle, parking lot, venue, lift, elevator, spatial, road, fluid flow, home, room, office, house, building, warehouse, storage, system, ventilation, fan, pipe, duct, people, human, car, boat, truck, airplane, drone, downtown, crowd, impulsive event, cyclo-stationary, environment, vibration, material, surface, 3-dimensional, 2-dimensional, local, global, presence, and/or another measurable quantity/variable.

Sliding Window/Algorithm

Sliding time window may have time varying window width. It may be smaller at the beginning to enable fast acquisition and may increase over time to a steady-state size. The steady-state size may be related to the frequency, repeated motion, transient motion, and/or STI to be monitored. Even in steady state, the window size may be adaptively (and/or dynamically) changed (e.g. adjusted, varied, modified) based on battery life, power consumption, available computing power, change in amount of targets, the nature of motion to be monitored, etc.

The time shift between two sliding time windows at adjacent time instance may be constant/variable/locally adaptive/dynamically adjusted over time. When shorter time shift is used, the update of any monitoring may be more frequent which may be used for fast changing situations, object motions, and/or objects. Longer time shift may be used for slower situations, object motions, and/or objects.

The window width/size and/or time shift may be changed (e.g. adjusted, varied, modified) upon a user request/choice. The time shift may be changed automatically (e.g. as controlled by processor/computer/server/hub device/cloud server) and/or adaptively (and/or dynamically).

At least one characteristics (e.g. characteristic value, or characteristic point) of a function (e.g. auto-correlation function, auto-covariance function, cross-correlation function, cross-covariance function, power spectral density, time function, frequency domain function, frequency transform) may be determined (e.g. by an object tracking server, the processor, the Type 1 heterogeneous device, the Type 2 heterogeneous device, and/or another device). The at least one characteristics of the function may include: a maximum, minimum, extremum, local maximum, local minimum, local extremum, local extremum with positive time offset, first local extremum with positive time offset, n^th local extremum with positive time offset, local extremum with negative time offset, first local extremum with negative time offset, n^th local extremum with negative time offset, constrained maximum, constrained minimum, constrained extremum, significant maximum, significant minimum, significant extremum, slope, derivative, higher order derivative, maximum slope, minimum slope, local maximum slope, local maximum slope with positive time offset, local minimum slope, constrained maximum slope, constrained minimum slope, maximum higher order derivative, minimum higher order derivative, constrained higher order derivative, zero-crossing, zero crossing with positive time offset, n^th zero crossing with positive time offset, zero crossing with negative time offset, n^th zero crossing with negative time offset, constrained zero-crossing, zero-crossing of slope, zero-crossing of higher order derivative, and/or another characteristics. At least one argument of the function associated with the at least one characteristics of the function may be identified. Some quantity (e.g. spatial-temporal information of the object) may be determined based on the at least one argument of the function.

A characteristics (e.g. characteristics of motion of an object in the venue) may comprise at least one of an instantaneous characteristics, short-term characteristics, repetitive characteristics, recurring characteristics, history, incremental characteristics, changing characteristics, deviational characteristics, phase, magnitude, degree, time characteristics, frequency characteristics, time-frequency characteristics, decomposition characteristics, orthogonal decomposition characteristics, non-orthogonal decomposition characteristics, deterministic characteristics, probabilistic characteristics, stochastic characteristics, autocorrelation function (ACF), mean, variance, standard deviation, measure of variation, spread, dispersion, deviation, divergence, range, interquartile range, total variation, absolute deviation, total deviation, statistics, duration, timing, trend, periodic characteristics, repetition characteristics, long-term characteristics, historical characteristics, average characteristics, current characteristics, past characteristics, future characteristics, predicted characteristics, location, distance, height, speed, direction, velocity, acceleration, change of the acceleration, angle, angular speed, angular velocity, angular acceleration of the object, change of the angular acceleration, orientation of the object, angular of rotation, deformation of the object, shape of the object, change of shape of the object, change of size of the object, change of structure of the object, and/or change of characteristics of the object.

At least one local maximum and at least one local minimum of the function may be identified. At least one local signal-to-noise-ratio-like (SNR-like) parameter may be computed for each pair of adjacent local maximum and local minimum. The SNR-like parameter may be a function (e.g. linear, log, exponential function, monotonic function) of a fraction of a quantity (e.g. power, magnitude) of the local maximum over the same quantity of the local minimum. It may also be the function of a difference between the quantity of the local maximum and the same quantity of the local minimum. Significant local peaks may be identified or selected. Each significant local peak may be a local maximum with SNR-like parameter greater than a threshold T1 and/or a local maximum with amplitude greater than a threshold T2. The at least one local minimum and the at least one local minimum in the frequency domain may be identified/computed using a persistence-based approach.

A set of selected significant local peaks may be selected from the set of identified significant local peaks based on a selection criterion (e.g. a quality criterion, a signal quality condition). The characteristics/STI of the object may be computed based on the set of selected significant local peaks and frequency values associated with the set of selected significant local peaks. In one example, the selection criterion may always correspond to select the strongest peaks in a range. While the strongest peaks may be selected, the unselected peaks may still be significant (rather strong).

Unselected significant peaks may be stored and/or monitored as "reserved" peaks for use in future selection in future sliding time windows. As an example, there may be a particular peak (at a particular frequency) appearing consistently over time. Initially, it may be significant but not selected (as other peaks may be stronger). But in later time, the peak may become stronger and more dominant and may be selected. When it became "selected", it may be back-traced in time and made "selected" in the earlier time when it was significant but not selected. In such case, the back-traced peak may replace a previously selected peak in an early time. The replaced peak may be the relatively weakest, or a peak that appear in isolation in time (i.e. appearing only briefly in time).

In another example, the selection criterion may not correspond to select the strongest peaks in the range. Instead, it may consider not only the "strength" of the peak, but the "trace" of the peak—peaks that may have happened in the past, especially those peaks that have been identified for a long time.

For example, if a finite state machine (FSM) is used, it may select the peak(s) based on the state of the FSM. Decision thresholds may be computed adaptively (and/or dynamically) based on the state of the FSM.

A similarity score and/or component similarity score may be computed (e.g. by a server (e.g. hub device), the processor, the Type 1 device, the Type 2 device, a local server, a cloud server, and/or another device) based on a pair of temporally adjacent CI of a TSCI. The pair may come from the same sliding window or two different sliding windows. The similarity score may also be based on a pair of, temporally adjacent or not so adjacent, CI from two different TSCI. The similarity score and/or component similar score may be/comprise: time reversal resonating strength (TRRS), correlation, cross-correlation, auto-correlation, correlation indicator, covariance, cross-covariance, auto-covariance, inner product of two vectors, distance score, norm, metric, quality metric, signal quality condition, statistical characteristics, discrimination score, neural network, deep learning network, machine learning, training, discrimination, weighted averaging, preprocessing, denoising, signal conditioning, filtering, time correction, timing compensation, phase offset compensation, transformation, component-wise operation, feature extraction, finite state machine, and/or another score. The characteristics and/or STI may be determined/computed based on the similarity score.

Any threshold may be pre-determined, adaptively (and/or dynamically) determined and/or determined by a finite state machine. The adaptive determination may be based on time, space, location, antenna, path, link, state, battery life, remaining battery life, available power, available computational resources, available network bandwidth, etc.

A threshold to be applied to a test statistics to differentiate two events (or two conditions, or two situations, or two states), A and B, may be determined. Data (e.g. CI, channel state information (CSI), power parameter) may be collected under A and/or under B in a training situation. The test statistics may be computed based on the data. Distributions of the test statistics under A may be compared with distributions of the test statistics under B (reference distribution), and the threshold may be chosen according to some criteria. The criteria may comprise: maximum likelihood (ML), maximum aposterior probability (MAP), discriminative training, minimum Type 1 error for a given Type 2 error, minimum Type 2 error for a given Type 1 error, and/or other criteria (e.g. a quality criterion, signal quality condition). The threshold may be adjusted to achieve different sensitivity to the A, B and/or another event/condition/situation/state. The threshold adjustment may be automatic, semi-automatic and/or manual. The threshold adjustment may be applied once, sometimes, often, periodically, repeatedly, occasionally, sporadically, and/or on demand. The threshold adjustment may be adaptive (and/or dynamically adjusted). The threshold adjustment may depend on the object, object movement/location/direction/action, object characteristics/ STI/size/property/trait/habit/behavior, the venue, feature/ fixture/furniture/barrier/material/machine/living thing/ thing/object/boundary/surface/medium that is in/at/of the venue, map, constraint of the map (or environmental model), the event/state/situation/condition, time, timing, duration, current state, past history, user, and/or a personal preference, etc.

A stopping criterion (or skipping or bypassing or blocking or pausing or passing or rejecting criterion) of an iterative algorithm may be that change of a current parameter (e.g. offset value) in the updating in an iteration is less than a threshold. The threshold may be 0.5, 1, 1.5, 2, or another number. The threshold may be adaptive (and/or dynamically adjusted). It may change as the iteration progresses. For the offset value, the adaptive threshold may be determined based on the task, particular value of the first time, the current time offset value, the regression window, the regression analysis, the regression function, the regression error, the convexity of the regression function, and/or an iteration number.

The local extremum may be determined as the corresponding extremum of the regression function in the regression window. The local extremum may be determined based on a set of time offset values in the regression window and a set of associated regression function values. Each of the set of associated regression function values associated with the set of time offset values may be within a range from the corresponding extremum of the regression function in the regression window.

The searching for a local extremum may comprise robust search, minimization, maximization, optimization, statistical optimization, dual optimization, constraint optimization, convex optimization, global optimization, local optimization an energy minimization, linear regression, quadratic regression, higher order regression, linear programming, nonlinear programming, stochastic programming, combinatorial optimization, constraint programming, constraint satisfaction, calculus of variations, optimal control, dynamic programming, mathematical programming, multi-objective optimization, multi-modal optimization, disjunctive programming, space mapping, infinite-dimensional optimization, heuristics, metaheuristics, convex programming, semidefinite programming, conic programming, cone programming, integer programming, quadratic programming, fractional programming, numerical analysis, simplex algorithm, iterative method, gradient descent, subgradient method, coordinate descent, conjugate gradient method, Newton's algorithm, sequential quadratic programming, interior point method, ellipsoid method, reduced gradient method, quasi-Newton method, simultaneous perturbation stochastic approximation, interpolation method, pattern search method, line search, non-differentiable optimization, genetic algorithm, evolutionary algorithm, dynamic relaxation, hill climbing, particle swarm optimization, gravitation search algorithm, simulated annealing, memetic algorithm, differential evolution, dynamic relaxation, stochastic tunneling, Tabu search, reactive search optimization, curve fitting, least square, simulation based optimization, variational calculus, and/or variant. The search for local extremum may be associated with an objective function, loss function, cost function, utility function, fitness function, energy function, and/or an energy function.

Regression may be performed using regression function to fit sampled data (e.g. CI, feature of CI, component of CI) or another function (e.g. autocorrelation function) in a regression window. In at least one iteration, a length of the regression window and/or a location of the regression window may change. The regression function may be linear function, quadratic function, cubic function, polynomial function, and/or another function.

The regression analysis may minimize at least one of error, aggregate error, component error, error in projection domain, error in selected axes, error in selected orthogonal axes, absolute error, square error, absolute deviation, square deviation, higher order error (e.g. third order, fourth order), robust error (e.g. square error for smaller error magnitude and absolute error for larger error magnitude, or first kind of error for smaller error magnitude and second kind of error for larger error magnitude), another error, weighted sum (or weighted mean) of absolute/square error (e.g. for wireless transmitter with multiple antennas and wireless receiver with multiple antennas, each pair of transmitter antenna and receiver antenna form a link), mean absolute error, mean square error, mean absolute deviation, and/or mean square deviation. Error associated with different links may have different weights. One possibility is that some links and/or some components with larger noise or lower signal quality metric may have smaller or bigger weight.), weighted sum of square error, weighted sum of higher order error, weighted sum of robust error, weighted sum of the another error, absolute cost, square cost, higher order cost, robust cost, another cost, weighted sum of absolute cost, weighted sum of square cost, weighted sum of higher order cost, weighted sum of robust cost, and/or weighted sum of another cost.

The regression error determined may be an absolute error, square error, higher order error, robust error, yet another error, weighted sum of absolute error, weighted sum of square error, weighted sum of higher order error, weighted sum of robust error, and/or weighted sum of the yet another error.

The time offset associated with maximum regression error (or minimum regression error) of the regression function with respect to the particular function in the regression window may become the updated current time offset in the iteration.

A local extremum may be searched based on a quantity comprising a difference of two different errors (e.g. a difference between absolute error and square error). Each of the two different errors may comprise an absolute error, square error, higher order error, robust error, another error, weighted sum of absolute error, weighted sum of square error, weighted sum of higher order error, weighted sum of robust error, and/or weighted sum of the another error.

The quantity may be compared with a reference data or a reference distribution, such as an F-distribution, central F-distribution, another statistical distribution, threshold, threshold associated with probability/histogram, threshold associated with probability/histogram of finding false peak, threshold associated with the F-distribution, threshold associated the central F-distribution, and/or threshold associated with the another statistical distribution.

The regression window may be determined based on at least one of: the movement (e.g. change in position/location) of the object, quantity associated with the object, the at least one characteristics and/or STI of the object associated with the movement of the object, estimated location of the local extremum, noise characteristics, estimated noise characteristics, signal quality metric, F-distribution, central F-distribution, another statistical distribution, threshold, preset threshold, threshold associated with probability/histogram, threshold associated with desired probability, threshold associated with probability of finding false peak, threshold associated with the F-distribution, threshold associated with the central F-distribution, threshold associated with the another statistical distribution, condition that quantity at the window center is largest within the regression window, condition that the quantity at the window center is largest within the regression window, condition that there is only one of the local extremum of the particular function for the particular value of the first time in the regression window, another regression window, and/or another condition.

The width of the regression window may be determined based on the particular local extremum to be searched. The local extremum may comprise first local maximum, second local maximum, higher order local maximum, first local maximum with positive time offset value, second local maximum with positive time offset value, higher local maximum with positive time offset value, first local maximum with negative time offset value, second local maximum with negative time offset value, higher local maximum with negative time offset value, first local minimum, second local minimum, higher local minimum, first local minimum with positive time offset value, second local minimum with positive time offset value, higher local minimum with positive time offset value, first local minimum with negative time offset value, second local minimum with negative time offset value, higher local minimum with negative time offset value, first local extremum, second local extremum, higher local extremum, first local extremum with positive time offset value, second local extremum with positive time offset value, higher local extremum with positive time offset value, first local extremum with negative time offset value, second local extremum with negative time offset value, and/or higher local extremum with negative time offset value.

A current parameter (e.g. time offset value) may be initialized based on a target value, target profile, trend, past trend, current trend, target speed, speed profile, target speed profile, past speed trend, the motion or movement (e.g. change in position/location) of the object, at least one characteristics and/or STI of the object associated with the movement of object, positional quantity of the object, initial speed of the object associated with the movement of the object, predefined value, initial width of the regression window, time duration, value based on carrier frequency of the signal, value based on subcarrier frequency of the signal, bandwidth of the signal, amount of antennas associated with the channel, noise characteristics, signal h metric, and/or an adaptive (and/or dynamically adjusted) value. The current time offset may be at the center, on the left side, on the right side, and/or at another fixed relative location, of the regression window.

In the presentation, information may be displayed with a map (or environmental model) of the venue. The information may comprise: location, zone, region, area, coverage area, corrected location, approximate location, location with respect to (w.r.t.) a map of the venue, location w.r.t. a segmentation of the venue, direction, path, path w.r.t. the map and/or the segmentation, trace (e.g. location within a time window such as the past 5 seconds, or past 10 seconds; the time window duration may be adjusted adaptively (and/or dynamically); the time window duration may be adaptively (and/or dynamically) adjusted w.r.t. speed, acceleration, etc.), history of a path, approximate regions/zones along a path, history/summary of past locations, history of past locations of interest, frequently-visited areas, customer traffic, crowd distribution, crowd behavior, crowd control information, speed, acceleration, motion statistics, breathing rate, heart rate, presence/absence of motion, presence/absence of people or pets or object, presence/absence of vital sign, gesture, gesture control (control of devices using gesture), location-based gesture control, information of a location-based operation, identity (ID) or identifier of the respect object (e.g. pet, person, self-guided machine/device, vehicle, drone, car, boat, bicycle, self-guided vehicle, machine with fan, air-conditioner, TV, machine with movable part), identification of a user (e.g. person), information of the user, location/speed/acceleration/direction/motion/gesture/gesture control/motion trace of the user, ID or identifier of the user, activity of the user, state of the user, sleeping/resting characteristics of the user, emotional state of the user, vital sign of the user, environment information of the venue, weather information of the venue, earthquake, explosion, storm, rain, fire, temperature, collision, impact, vibration, event, door-open event, door-close event, window-open event, window-close event, fall-down event, burning event, freezing event, water-related event, wind-related event, air-movement event, accident event, pseudo-periodic event (e.g. running on treadmill, jumping up and down, skipping rope, somersault, etc.), repeated event, crowd event, vehicle event, gesture of the user (e.g. hand gesture, arm gesture, foot gesture, leg gesture, body gesture, head gesture, face gesture, mouth gesture, eye gesture, etc.).

The location may be 2-dimensional (e.g. with 2D coordinates), 3-dimensional (e.g. with 3D coordinates). The location may be relative (e.g. w.r.t. a map or environmental model) or relational (e.g. halfway between point A and point B, around a corner, up the stairs, on top of table, at the ceiling, on the floor, on a sofa, close to point A, a distance R from point A, within a radius of R from point A, etc.). The location may be expressed in rectangular coordinate, polar coordinate, and/or another representation.

The information (e.g. location) may be marked with at least one symbol. The symbol may be time varying. The symbol may be flashing and/or pulsating with or without changing color/intensity. The size may change over time. The orientation of the symbol may change over time. The symbol may be a number that reflects an instantaneous quantity (e.g. vital sign/breathing rate/heart rate/gesture/state/status/action/motion of a user, temperature, network traffic, network connectivity, status of a device/machine, remaining power of a device, status of the device, etc.). The rate of change, the size, the orientation, the color, the intensity and/or the symbol may reflect the respective motion. The information may be presented visually and/or described verbally (e.g. using pre-recorded voice, or voice synthesis). The information may be described in text. The information may also be presented in a mechanical way (e.g. an animated gadget, a movement of a movable part).

The user-interface (UI) device may be a smart phone (e.g. iPhone, Android phone), tablet (e.g. iPad), laptop (e.g. notebook computer), personal computer (PC), device with graphical user interface (GUI), smart speaker, device with voice/audio/speaker capability, virtual reality (VR) device, augmented reality (AR) device, smart car, display in the car, voice assistant, voice assistant in a car, etc.

The map (or environmental model) may be 2-dimensional, 3-dimensional and/or higher-dimensional. (e.g. a time varying 2D/3D map/environmental model) Walls, windows, doors, entrances, exits, forbidden areas may be marked on the map or the model. The map may comprise floor plan of a facility. The map or model may have one or more layers (overlays). The map/model may be a maintenance map/model comprising water pipes, gas pipes, wiring, cabling, air ducts, crawl-space, ceiling layout, and/or underground layout. The venue may be segmented/subdivided/zoned/grouped into multiple zones/regions/geographic regions/sectors/sections/territories/districts/precincts/localities/neighborhoods/areas/stretches/expanse such as bedroom, living room, storage room, walkway, kitchen, dining room, foyer, garage, first floor, second floor, rest room, offices, conference room, reception area, various office areas, various warehouse regions, various facility areas, etc. The segments/regions/areas may be presented in a map/model. Different regions may be color-coded. Different regions may be presented with a characteristic (e.g. color, brightness, color intensity, texture, animation, flashing, flashing rate, etc.). Logical segmentation of the venue may be done using the at least one heterogeneous Type 2 device, or a server (e.g. hub device), or a cloud server, etc.

Here is an example of the disclosed system, apparatus, and method. Stephen and his family want to install the disclosed wireless motion detection system to detect motion in their 2000 sqft two-storey town house in Seattle, Washington. Because his house has two storeys, Stephen decided to use one Type 2 device (named A) and two Type 1 devices (named B and C) in the ground floor. His ground floor has predominantly three rooms: kitchen, dining room and living room arranged in a straight line, with the dining room in the middle. The kitchen and the living rooms are on opposite end of the house. He put the Type 2 device (A) in the dining room, and put one Type 1 device (B) in the kitchen and the other Type 1 device (C) in the living room. With this placement of the devices, he is practically partitioning the ground floor into 3 zones (dining room, living room and kitchen) using the motion detection system. When motion is detected by the AB pair and the AC pair, the system would analyze the motion information and associate the motion with one of the 3 zones.

When Stephen and his family go out on weekends (e.g. to go for a camp during a long weekend), Stephen would use a mobile phone app (e.g. Android phone app or iPhone app) to turn on the motion detection system. When the system detects motion, a warning signal is sent to Stephen (e.g. an SMS text message, an email, a push message to the mobile phone app, etc.). If Stephen pays a monthly fee (e.g. $10/month), a service company (e.g. security company) will receive the warning signal through wired network (e.g. broadband) or wireless network (e.g. home WiFi, LTE, 3G, 2.5G, etc.) and perform a security procedure for Stephen (e.g. call him to verify any problem, send someone to check on the house, contact the police on behalf of Stephen, etc.). Stephen loves his aging mother and cares about her well-being when she is alone in the house. When the mother is alone in the house while the rest of the family is out (e.g. go to work, or shopping, or go on vacation), Stephen would turn on the motion detection system using his mobile app to ensure the mother is ok. He then uses the mobile app to monitor his mother's movement in the house. When Stephen uses the mobile app to see that the mother is moving around the house among the 3 regions, according to her daily routine, Stephen knows that his mother is doing ok. Stephen is thankful that the motion detection system can help him monitor his mother's well-being while he is away from the house.

On a typical day, the mother would wake up at around 7 AM. She would cook her breakfast in the kitchen for about 20 minutes. Then she would eat the breakfast in the dining room for about 30 minutes. Then she would do her daily exercise in the living room, before sitting down on the sofa in the living room to watch her favorite TV show. The motion detection system enables Stephen to see the timing of the movement in each of the 3 regions of the house. When the motion agrees with the daily routine, Stephen knows roughly that the mother should be doing fine. But when the motion pattern appears abnormal (e.g. there is no motion until 10 AM, or she stayed in the kitchen for too long, or she remains motionless for too long, etc.), Stephen suspects something is wrong and would call the mother to check on her. Stephen may even get someone (e.g. a family member, a neighbor, a paid personnel, a friend, a social worker, a service provider) to check on his mother.

At some time, Stephen feels like repositioning the Type 2 device. He simply unplugs the device from the original AC power plug and plug it into another AC power plug. He is happy that the wireless motion detection system is plug-and-play and the repositioning does not affect the operation of the system. Upon powering up, it works right away.

Sometime later, Stephen is convinced that our wireless motion detection system can really detect motion with very high accuracy and very low alarm, and he really can use the mobile app to monitor the motion in the ground floor. He decides to install a similar setup (i.e. one Type 2 device and two Type 1 devices) in the second floor to monitor the bedrooms in the second floor. Once again, he finds that the system set up is extremely easy as he simply needs to plug the Type 2 device and the Type 1 devices into the AC power plug in the second floor. No special installation is needed. And he can use the same mobile app to monitor motion in the ground floor and the second floor. Each Type 2 device in the ground floor/second floor can interact with all the Type 1 devices in both the ground floor and the second floor. Stephen is happy to see that, as he doubles his investment in the Type 1 and Type 2 devices, he has more than double the capability of the combined systems.

According to various embodiments, each CI (CI) may comprise at least one of: channel state information (CSI), frequency domain CSI, frequency representation of CSI, frequency domain CSI associated with at least one sub-band, time domain CSI, CSI in domain, channel response, estimated channel response, channel impulse response (CIR), channel frequency response (CFR), channel characteristics, channel filter response, CSI of the wireless multipath channel, information of the wireless multipath channel, timestamp, auxiliary information, data, meta data, user data, account data, access data, security data, session data, status data, supervisory data, household data, identity (ID), identifier, device data, network data, neighborhood data, environment data, real-time data, sensor data, stored data, encrypted data, compressed data, protected data, and/or another CI. In one embodiment, the disclosed system has hardware components (e.g. wireless transmitter/receiver with antenna, analog circuitry, power supply, processor, memory) and corresponding software components. According to various embodiments of the present teaching, the disclosed system includes Bot (referred to as a Type 1 device) and Origin (referred to as a Type 2 device) for vital sign detection and monitoring. Each device comprises a transceiver, a processor and a memory.

The disclosed system can be applied in many cases. In one example, the Type 1 device (transmitter) may be a small WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. In one example, the Type 2 (receiver) may be a WiFi-enabled device resting on the table. It may also be a WiFi-enabled television (TV), set-top box (STB), a smart speaker (e.g. Amazon echo), a smart refrigerator, a smart microwave oven, a mesh network router, a mesh network satellite, a smart phone, a computer, a tablet, a smart plug, etc. The Type 1 device and Type 2 devices may be placed in/near a conference room to count people. The Type 1 device and Type 2 devices may be in a well-being monitoring system for older adults to monitor their daily activities and any sign of symptoms (e.g. dementia, Alzheimer's disease). The Type 1 device and Type 2 device may be used in baby monitors to monitor the vital signs (breathing) of a living baby. The Type 1 device and Type 2 devices may be placed in bedrooms to monitor quality of sleep and any sleep apnea. The Type 1 device and Type 2 devices may be placed in cars to monitor well-being of passengers and driver, detect any sleeping of driver and detect any babies left in a car. The Type 1 device and Type 2 devices may be used in logistics to prevent human trafficking by monitoring any human hidden in trucks and containers. The Type 1 device and Type 2 devices may be deployed by emergency service at disaster area to search for trapped victims in debris. The Type 1 device and Type 2 devices may be deployed in an area to detect breathing of any intruders. There are numerous applications of wireless breathing monitoring without wearables.

Hardware modules may be constructed to contain the Type 1 transceiver and/or the Type 2 transceiver. The hardware modules may be sold to/used by variable brands to design, build and sell final commercial products. Products using the disclosed system and/or method may be home/office security products, sleep monitoring products, WiFi products, mesh products, TV, STB, entertainment system, HiFi, speaker, home appliance, lamps, stoves, oven, microwave oven, table, chair, bed, shelves, tools, utensils, torches, vacuum cleaner, smoke detector, sofa, piano, fan, door, window, door/window handle, locks, smoke detectors, car accessories, computing devices, office devices, air conditioner, heater, pipes, connectors, surveillance camera, access point, computing devices, mobile devices, LTE devices, 3G/4G/5G/6G devices, UMTS devices, 3GPP devices, GSM devices, EDGE devices, TDMA devices, FDMA devices, CDMA devices, WCDMA devices, TD-SCDMA devices, gaming devices, eyeglasses, glass panels, VR goggles, necklace, watch, waist band, belt, wallet, pen, hat, wearables, implantable device, tags, parking tickets, smart phones, etc.

The summary may comprise: analytics, output response, selected time window, subsampling, transform, and/or projection. The presenting may comprise presenting at least one of: monthly/weekly/daily view, simplified/detailed view, cross-sectional view, small/large form-factor view, color-coded view, comparative view, summary view, animation, web view, voice announcement, and another presentation related to the periodic/repetition characteristics of the repeating motion.

A Type 1/Type 2 device may be an antenna, a device with antenna, a device with a housing (e.g. for radio, antenna, data/signal processing unit, wireless IC, circuits), device that has interface to attach/connect to/link antenna, device that is interfaced to/attached to/connected to/linked to another device/system/computer/phone/network/data aggregator, device with a user interface (UI)/graphical UI/display, device with wireless transceiver, device with wireless transmitter, device with wireless receiver, internet-of-thing (IoT) device, device with wireless network, device with both wired networking and wireless networking capability, device with wireless integrated circuit (IC), Wi-Fi device, device with Wi-Fi chip (e.g. 802.11a/b/g/n/ac/ax standard compliant), Wi-Fi access point (AP), Wi-Fi client, Wi-Fi router, Wi-Fi repeater, Wi-Fi hub, Wi-Fi mesh network router/hub/AP, wireless mesh network router, adhoc network device, wireless mesh network device, mobile device (e.g. 2G/2.5G/3G/3.5G/4G/LTE/5G/6G/7G, UMTS, 3GPP, GSM, EDGE, TDMA, FDMA, CDMA, WCDMA, TD-SCDMA), cellular device, base station, mobile network base station, mobile network hub, mobile network compatible device, LTE device, device with LTE module, mobile module (e.g. circuit board with mobile-enabling chip (IC) such as Wi-Fi chip, LTE chip, BLE chip), Wi-Fi chip (IC), LTE chip, BLE chip, device with mobile module, smart phone, companion device (e.g. dongle, attachment, plugin) for smart phones, dedicated device, plug-in device, AC-powered device, battery-powered device, device with processor/memory/set of instructions, smart device/gadget/items: clock, stationary, pen, user-interface, paper, mat, camera, television (TV), set-top-box, microphone, speaker, refrigerator, oven, machine, phone, wallet, furniture, door, window, ceiling, floor, wall, table, chair, bed, night-stand, air-conditioner, heater, pipe, duct, cable, carpet, decoration, gadget, USB device, plug, dongle, lamp/light, tile, ornament, bottle, vehicle, car, AGV, drone, robot, laptop, tablet, computer, harddisk, network card, instrument, racket, ball, shoe, wearable, clothing, glasses, hat, necklace, food, pill, small device that moves in the body of creature (e.g. in blood vessels, in lymph fluid, digestive system), and/or another device. The Type 1 device and/or Type 2 device may be communicatively coupled with: the internet, another device with access to internet (e.g. smart phone), cloud server (e.g. hub device), edge server, local server, and/or storage. The Type 1 device and/or the Type 2 device may operate with local control, can be controlled by another device via a wired/wireless connection, can operate automatically, or can be controlled by a central system that is remote (e.g. away from home).

In one embodiment, a Type B device may be a transceiver that may perform as both Origin (a Type 2 device, a Rx device) and Bot (a Type 1 device, a Tx device), i.e., a Type B device may be both Type 1 (Tx) and Type 2 (Rx) devices (e.g. simultaneously or alternately), for example, mesh devices, a mesh router, etc. In one embodiment, a Type A device may be a transceiver that may only function as Bot (a Tx device), i.e., Type 1 device only or Tx only, e.g., simple IoT devices. It may have the capability of Origin (Type 2 device, Rx device), but somehow it is functioning only as Bot in the embodiment. All the Type A and Type B devices form a tree structure. The root may be a Type B device with network (e.g. internet) access. For example, it may be connected to broadband service through a wired connection (e.g. Ethernet, cable modem, ADSL/HDSL modem) connection or a wireless connection (e.g. LTE, 3G/4G/5G, WiFi, Bluetooth, microwave link, satellite link, etc.). In one embodiment, all the Type A devices are leaf node. Each Type B device may be the root node, non-leaf node, or leaf node.

Type 1 device (transmitter, or Tx) and Type 2 device (receiver, or Rx) may be on same device (e.g. RF chip/IC) or simply the same device. The devices may operate at high frequency band, such as 28 GHz, 60 GHz, 77 GHz, etc. The RF chip may have dedicated Tx antennas (e.g. 32 antennas) and dedicated Rx antennas (e.g. another 32 antennas).

One Tx antenna may transmit a wireless signal (e.g. a series of probe signal, perhaps at 100 Hz). Alternatively, all Tx antennas may be used to transmit the wireless signal with beamforming (in Tx), such that the wireless signal is focused in certain direction (e.g. for energy efficiency or boosting the signal to noise ratio in that direction, or low power operation when "scanning" that direction, or low power operation if object is known to be in that direction).

The wireless signal hits an object (e.g. a living human lying on a bed 4 feet away from the Tx/Rx antennas, with breathing and heart beat) in a venue (e.g. a room). The object motion (e.g. lung movement according to breathing rate, or blood-vessel movement according to heart beat) may impact/modulate the wireless signal. All Rx antennas may be used to receive the wireless signal.

Beamforming (in Rx and/or Tx) may be applied (digitally) to "scan" different directions. Many directions can be scanned or monitored simultaneously. With beamforming, "sectors" (e.g. directions, orientations, bearings, zones, regions, segments) may be defined related to the Type 2 device (e.g. relative to center location of antenna array). For each probe signal (e.g. a pulse, an ACK, a control packet, etc.), a channel information or CI (e.g. channel impulse response/CIR, CSI, CFR) is obtained/computed for each sector (e.g. from the RF chip). In breathing detection, one may collect CIR in a sliding window (e.g. 30 sec, and with 100 Hz sounding/probing rate, one may have 3000 CIR over 30 sec).

The CIR may have many taps (e.g. N1 components/taps). Each tap may be associated with a time lag, or a time-of-flight (tof, e.g. time to hit the human 4 feet away and back). When a person is breathing in a certain direction at a certain distance (e.g. 4 ft), one may search for the CIR in the "certain direction". Then one may search for the tap corresponding to the "certain distance". Then one may compute the breathing rate and heart rate from that tap of that CIR.

One may consider each tap in the sliding window (e.g. 30 second window of "component time series") as a time function (e.g. a "tap function", the "component time series"). One may examine each tap function in search of a strong periodic behavior (e.g. corresponds to breathing, perhaps in the range of 10 bpm to 40 bpm).

The Type 1 device and/or the Type 2 device may have external connections/links and/or internal connections/links. The external connections (e.g. connection 1110) may be associated with 2G/2.5G/3G/3.5G/4G/LTE/5G/6G/7G/NBIoT, UWB, WiMax, Zigbee, 802.16 etc. The internal connections (e.g., 1114A and 1114B, 1116, 1118, 1120) may be associated with WiFi, an IEEE 802.11 standard, 802.11a/b/g/n/ac/ad/af/ag/ah/ai/aj/aq/ax/ay, Bluetooth, Bluetooth 1.0/1.1/1.2/2.0/2.1/3.0/4.0/4.1/4.2/5, BLE, mesh network, an IEEE 802.16/1/1a/1b/2/2a/a/b/c/d/e/f/g/h/i/j/k/l/m/n/o/p/ standard.

The Type 1 device and/or Type 2 device may be powered by battery (e.g. AA battery, AAA battery, coin cell battery, button cell battery, miniature battery, bank of batteries, power bank, car battery, hybrid battery, vehicle battery, container battery, non-rechargeable battery, rechargeable battery, NiCd battery, NiMH battery, Lithium ion battery, Zinc carbon battery, Zinc chloride battery, lead acid battery, alkaline battery, battery with wireless charger, smart battery, solar battery, boat battery, plane battery, other battery, temporary energy storage device, capacitor, fly wheel).

Any device may be powered by DC or direct current (e.g. from battery as described above, power generator, power convertor, solar panel, rectifier, DC-DC converter, with various voltages such as 1.2V, 1.5V, 3V, 5V, 6V, 9V, 12V, 24V, 40V, 42V, 48V, 110V, 220V, 380V, etc.) and may thus have a DC connector or a connector with at least one pin for DC power.

Any device may be powered by AC or alternating current (e.g. wall socket in a home, transformer, invertor, shore-power, with various voltages such as 100V, 110V, 120V, 100-127V, 200V, 220V, 230V, 240V, 220-240V, 100-240V, 250V, 380V, 50 Hz, 60 Hz, etc.) and thus may have an AC connector or a connector with at least one pin for AC power. The Type 1 device and/or the Type 2 device may be positioned (e.g. installed, placed, moved to) in the venue or outside the venue.

For example, in a vehicle (e.g. a car, truck, lorry, bus, special vehicle, tractor, digger, excavator, teleporter, bulldozer, crane, forklift, electric trolley, AGV, emergency vehicle, freight, wagon, trailer, container, boat, ferry, ship, submersible, airplane, air-ship, lift, mono-rail, train, tram, rail-vehicle, railcar, etc.), the Type 1 device and/or Type 2 device may be an embedded device embedded in the vehicle, or an add-on device (e.g. aftermarket device) plugged into a port in the vehicle (e.g. OBD port/socket, USB port/socket, accessory port/socket, 12V auxiliary power outlet, and/or 12V cigarette lighter port/socket).

For example, one device (e.g. Type 2 device) may be plugged into 12V cigarette lighter/accessory port or OBD port or the USB port (e.g. of a car/truck/vehicle) while the other device (e.g. Type 1 device) may be plugged into 12V cigarette lighter/accessory port or the OBD port or the USB port. The OBD port and/or USB port can provide power, signaling and/or network (of the car/truck/vehicle). The two devices may jointly monitor the passengers including children/babies in the car. They may be used to count the passengers, recognize the driver, detect presence of passenger in a particular seat/position in the vehicle.

In another example, one device may be plugged into 12V cigarette lighter/accessory port or OBD port or the USB port of a car/truck/vehicle while the other device may be plugged into 12V cigarette lighter/accessory port or OBD port or the USB port of another car/truck/vehicle.

In another example, there may be many devices of the same type A (e.g. Type 1 or Type 2) in many heterogeneous vehicles/portable devices/smart gadgets (e.g. automated guided vehicle/AGV, shopping/luggage/moving cart, parking ticket, golf cart, bicycle, smart phone, tablet, camera, recording device, smart watch, roller skate, shoes, jackets, goggle, hat, eye-wear, wearable, Segway, scooter, luggage tag, cleaning machine, vacuum cleaner, pet tag/collar/wearable/implant), each device either plugged into 12V accessory port/OBD port/USB port of a vehicle or embedded in a vehicle. There may be one or more device of the other type B (e.g. B is Type 1 if A is Type 2, or B is Type 2 if A is Type 1) installed at locations such as gas stations, street lamp post, street corners, tunnels, multi-storey parking facility, scattered locations to cover a big area such as factory/stadium/train station/shopping mall/construction site. The Type A device may be located, tracked or monitored based on the TSCI.

The area/venue may have no local connectivity, e.g., broadband services, WiFi, etc. The Type 1 and/or Type 2 device may be portable. The Type 1 and/or Type 2 device may support plug and play.

Pairwise wireless links may be established between many pairs of devices, forming the tree structure. In each pair (and the associated link), a device (second device) may be a non-leaf (Type B). The other device (first device) may be a leaf (Type A or Type B) or non-leaf (Type B). In the link, the first device functions as a bot (Type 1 device or a Tx device) to send a wireless signal (e.g. probe signal) through the wireless multipath channel to the second device. The second device may function as an Origin (Type 2 device or Rx device) to receive the wireless signal, obtain the TSCI and compute a "linkwise analytics" based on the TSCI.

In some embodiments, a system is disclosed to perform wireless vital sign monitoring, e.g. with ACF enhancement. The system can use a time series of channel information (TSCI) obtained from a wireless signal transmitted from a transmitter to a receiver to detect a vital sign (e.g. breathing or heartbeat or a periodic motion) of an object (e.g. a person, a user, a baby) in a venue based on the TSCI.

The channel information (CI) may be channel impulse response (CIR), channel frequency response (CFR), and/or channel state information (CSI), RSSI, etc., obtained from the received wireless signal. The wireless signal may be an mmWave/UWB/radar signal. The transmitter and the receiver may be co-located (e.g. on the same device, or on the same circuit board such as in the case of radar), or at different locations.

In some embodiments, a vital sign is detected based on a 2 dimensional (2D) decomposition of the TSCI which is enhanced using image processing filtering. To perform construction of 2D decomposition, for each CI, a CI-feature vector is constructed. The CI-feature vector may be constructed by a concatenation of a first basic feature of the CI and a second basic feature of a corresponding denoised CI. The denoised CI may be obtained using some simple denoising, e.g. based on phase (CI_1-CI_2), where 1 and 2 here refer to two different spatial streams. Any basic feature of a CI may comprise the CI itself, a magnitude of the CI, a phase of the CI, a magnitude of a component of CI, a phase of a component of CI, or a function of any magnitude/phase. The second basic feature of a corresponding denoised CI may comprise a difference between the phases of two temporally adjacent CI.

In some embodiments, the 2D decomposition is performed in a sliding time window of TSCI. The sliding time window is associated with a time stamp or time index. Let the time index of the $i^{th}$ sliding window be i, which is referred to as "real time". A sliding window and the next sliding window may have an overlap (e.g. 10% overlap, 50% overlap, 90% overlap) corresponding to a time difference between two immediately adjacent sliding window time indices (i.e. time difference between time index k and k+1). The size of the sliding time window may be adjusted over time. The size may be smaller at the beginning of the sensing task and may increase over time.

In some embodiments, in each sliding window, a characteristic function is computed based on a transformation. The characteristic function may be a time function (e.g. the transformation may be autocorrelation function (ACF), or autocovariance function, etc.) of the CI-feature in the time window. Let the time index of the ACF (i.e. time shift) be j. The vital sign signal is a periodic signal. In the $i^{th}$ sliding time window, the characteristic (time) function would have a peak (local maximum) at a certain time-shift which corresponds to a period (or frequency) of the periodic vital sign signal. It may also have additional peaks at time-shift being integer multiples of the period.

In some embodiments, a 2D matrix A of size M×N is formed by putting the time function together according to the time index of the sliding time windows. Let a(i,j) be the element of A at the column i and row j, i=1, ..., M, j=1, ..., N. The $i^{th}$ column of A (i.e. a(i,*)) represents the sliding time function in the $i^{th}$ sliding time window. The index j of a(i,j) is the time-shift of the time function in the $i^{th}$ sliding time window, and a(i,j) is the value of the time function (e.g. ACF) at that time-shift. The 2D matrix A can be treated as an image, with a(I,j) being the image intensity at the $(i,j)^{th}$ pixel.

In some embodiments, as the frequency/period of the vital sign changes very slowly (i.e. almost unchanged within a short time change), the peak (local max) should form a horizontal, or near horizontal line in the image. But without the enhancement described below, the horizontal line(s) may be hardly visible or detectable in real world situations due to noise. With the enhancement, the horizontal line may become more visible or detectable.

In some embodiments, the characteristic function may be a frequency function (e.g. spectrum/power spectral density/short-time Fourier transform/wavelet transform/trigonometric transform/sinusoidal transform/frequency decomposition/filter-bank) of the CI-feature in the sliding time window. Let the frequency index of the sliding frequency function be j. The vital sign signal is a periodic signal. In the $i^{th}$ sliding time window, the sliding function would have a peak (local maximum) at a certain frequency which corresponds to the fundamental frequency (or period) of the periodic vital sign. There may be additional peaks at the harmonics, which are integer multiples of the fundamental frequency.

In some embodiments, a 2D matrix B of size M×N is formed by putting the frequency function together according to the time index of the sliding time windows. Let b(i,j) be the element of B at the column i and row j, i=1, ..., M, j=1, ..., N. The $i^{th}$ column of B (i.e. b(i,*)) represents the sliding frequency function in the $i^{th}$ sliding time window. The index j of b(i,j) is the frequency index of the frequency function in the $i^{th}$ sliding time window, and b(i,j) is the value at that frequency index. Similar to 2D matrix A, the 2D matrix B can be treated as an image, with b(i,j) being the image intensity at the $(i,j)^{th}$ pixel. As the frequency/period of the vital sign changes very slowly (i.e. almost unchanged within a short time change), the peak (local max) should form one or more horizontal, or near horizontal line in the image. But without the enhancement described below, the horizontal line(s) may be hardly visible or detectable in real world situations due to noise. With the enhancement, the horizontal line may become more visible or detectable.

The vital sign may be detected by detecting the horizontal line(s) in the 2D matrix A or B. But due to noise, often the peak(s) and/or the horizontal line(s) may not be obvious. Thus, the system may enhance the 2D decomposition, the peak(s) in particular, by applying image processing filters.

In some embodiments, to perform enhancement of 2D Decomposition, the image processing filter may comprise vertical highpass filter and horizontal lowpass filter. The horizontal lowpass filter may be used to take advantage of the horizontal line structure in the 2D decomposition. The vertical highpass filtering and horizontal lowpass filtering may be performed jointly, or separately. The separate vertical highpass filter, the separate horizontal lowpass filter, and/or the joint vertical highpass horizontal lowpass filter may be linear (e.g. FIR filter) or nonlinear (e.g. median filter, percentile, sorting). Multiple filtering orders are possible, e.g. vertical highpass first, followed by horizontal lowpass; or horizontal lowpass first, then followed by vertical highpass. There may be a succession of filtering, e.g. vertical highpass first, then horizontal lowpass, then vertical highpass; or horizontal lowpass first, then another horizontal lowpass, then vertical highpass.

For the vertical filtering, filtering may be applied to each column, or groups of columns, such as 3 columns or 5 columns or k columns. For one-column filtering (i.e. filtering applied to each column), the system may consider each column of the 2D matrix (A or B) as a time signal x(t) and apply 1-dimensional highpass filter (e.g. [−1 1], or [1 −1], or

[−1 2 −1], or [−2 4 −2], or [−1 3 −3 1], or [−1 0 2 0 −1], or [−1 4 −6 4 −1], etc., or a succession of more than one highpass filters each scaled by respective scaling factor) to x(t) to obtain a filtered signal y(t). The filtered signal y(t) may be added back to the time signal to obtain the enhanced column (i.e. x_enhanced(t)=x(t)+y(t)). In one embodiment, the same vertical filtering may be applied to all the columns. In another embodiment, different vertical filter may be applied to different columns. Such vertical filter may be chosen/decided adaptively.

In some embodiments, for 3-column (or k-column in general) vertical filtering, let x(t) be the center column (which is in the center among the 3 columns). The system may apply a 2D high pass filter to the 3 columns (or k columns) to obtain a filtered center column y(t). For example, the system may apply [0 −1 0; 0 2 0; 0 −1 0] which is [−1 2 −1] applied vertically, [−1 0 0; 0 2 0; 0 0 −1] which is [−1 2 −1] applied in diagonal direction, or [0 0 −1; 0 2 0; −1 0 0] which is [−1 2 −1] applied in anti-diagonal direction, or a succession of more than one highpass filter each scaled by respective scaling factor. The diagonal direction is 45 degree to the vertical line. Other angles such as 30 degree, 20 degree, 10 degree are possible. The filtered center column y(t) may be added back to the center column x(t) to obtain the enhanced center column (i.e. x_enhanced(t)=x(t)+y(t), or alternatively x_enhanced(t)=x(t)+alpha*y(t), where alpha is a scaling factor). In one embodiment, the same k-column vertical filtering may be applied to all the columns. In another embodiment, different k-column vertical filtering's may be applied to different columns. Such k-column vertical filter may be chosen/decided adaptively. For example, one column may be processed by 3-column vertical filtering while another column may be processed by 5-column vertical filtering.

In some embodiments, for the horizontal filtering, filtering may be applied to each row, or groups of rows, such as 3 rows or 5 rows or k rows. For one-row filtering (i.e. filtering applied to each row), the system may consider each row of the 2D matrix A or B as a time signal x(t) and apply 1-dimensional lowpass filter (e.g. [1 1]/2, [1 1 1]/3, [1 2 1]/4, [1 3 3 1]/8, [1 4 6 4 1]/16, [1 1 1 1 1]/5, 3-point median filter, 5-point median filter, 3-point percentile filter (X %, e.g. 50% for median filter), 3-point mode filter, etc., or a succession of more than one lowpass filters) to x(t) to obtain a filtered signal y(t). The filtered signal y(t) may be added back to the time signal to obtain the enhanced row (i.e. x_enhanced(t)=x(t)+y(t)). In one embodiment, the same horizontal filtering may be applied to all the rows. In another embodiment, different horizontal filters may be applied to different rows. Such horizontal filter may be chosen/decided adaptively.

In some embodiments, for 3-row (or k-row in general) horizontal filtering, let x(t) be the center row (which is in the center among the 3 rows). The system may apply a 2D lowpass filter to the 3 rows (or k rows) to obtain the enhanced center row y(t). For example, the system can apply [0 0 0; 1 2 1; 0 0 0]/4 which is [1 2 1] applied horizontally, [1 0 0; 0 2 0; 0 0 1]/4 which is [1 2 1] applied in diagonal direction, or [0 0 1; 0 2 0; 1 0 0] which is [1 2 1] applied in anti-diagonal direction, or a succession of more than one lowpass filters. The diagonal direction is 45 degree to the horizontal line. Other angles such as 30 degree, 20 degree, 10 degree are possible. In one embodiment, the same k-row horizontal filtering may be applied to all the rows. In another embodiment, different k-row horizontal filters may be applied to different rows. Such k-row horizontal filter may be chosen/decided adaptively. For example, one row may be processed by 3-row horizontal filtering while another row may be processed by 5-row horizontal filtering.

After the vertical highpass and horizontal lowpass filtering, histogram equalization or other histogram operation (e.g., histogram stretching, or contrast stretching) may be applied to a number of consecutive columns (which correspond to a number of consecutive sliding time windows).

Then vital signal detection can be performed based on then enhancement of 2D decomposition. For each time index (and associated sliding time window and corresponding column of the 2D decomposition), the system may make a tentative (not final) decision of whether the vital sign is present, or not. A final decision is made—that the vital sign is present, if vital sign is tentative. Whether vital sign is present or not, there would always be peaks in the enhanced 2D decomposition. So the system can do the following tests to make the tentative decision.

For Test 1, the system can consider a particular time index associated with a particular characteristic function (e.g. time function such as ACF, frequency function such as STFT) which is a particular column of the 2D decomposition. The system can test for presence of vital sign at the particular time by performing dynamic time warping (DTW), e.g. with respect to a normalized distance measure, between the particular characteristic function (e.g. ACF with an unknown vital sign frequency) and a reference characteristic function (e.g. trained ACF with a fixed training vital sign frequency). The DTW may be applied to account for possible mismatch of vital sign frequency between the two characteristic functions. The reference vital sign may be computed in a training phase, based on clustering a number of training characteristic function matched based on DTW, the number of training characteristic function obtained when training subject(s) with vital sign was present. The reference vital sign may also be from empirical vital sign data from adults, child, etc., without training. If the normalized distance measure is larger than a first threshold, the tentative decision is that vital sign is not present (i.e. vital sign not detected). If not, the system can perform Test 2.

For Test 2, let x(t) be the enhanced characteristic function. The system can compute x(t) −b for some value of b (e.g. 0.6, 0.5, 0.4, 0, etc.) and compute a number of zero crossing of x(t)−b (i.e. compute/count how many times x(t) cross the value of b). If the number of zero crossing is greater than a second threshold (probably due to noise), the tentative decision is that vital sign is not present (i.e. vital sign not detected). If not, the system can perform Test 3.

For Test 3, the system can find the peaks (local maximum) of the enhanced characteristic function. For example, the system can compute an inter-peak distance (e.g. adjacent-peak distance such that distance between the first and second peaks, or between second and third peaks, and so on, or a weighted average of the adjacent-peak distances). If the inter-peak distance is in an acceptable range (associated with vital sign, e.g. breathing, or heartbeat), the tentative decision is that vital sign is present (i.e. vital sign detected) and the inter-peak distance is the vital sign period (if the characteristic function is a time function) or vital sign frequency (if characteristic function is a frequency function). If not, vital sign is determined to be not present (i.e. vital sign not detected).

In some embodiments, for the final decision/conclusion at any time, the vital sign is concluded to be present (i.e. vital sign is declared to be detected, as the final decision) if A is larger than a third threshold (e.g. 0.9, 0.5, 0.1). A is the percentage of vital sign being tentatively detected in a certain period of time (e.g. 1 hour, 30 min, 15 min, 5 minute, 3 min, 1 min).

Figure 1B:
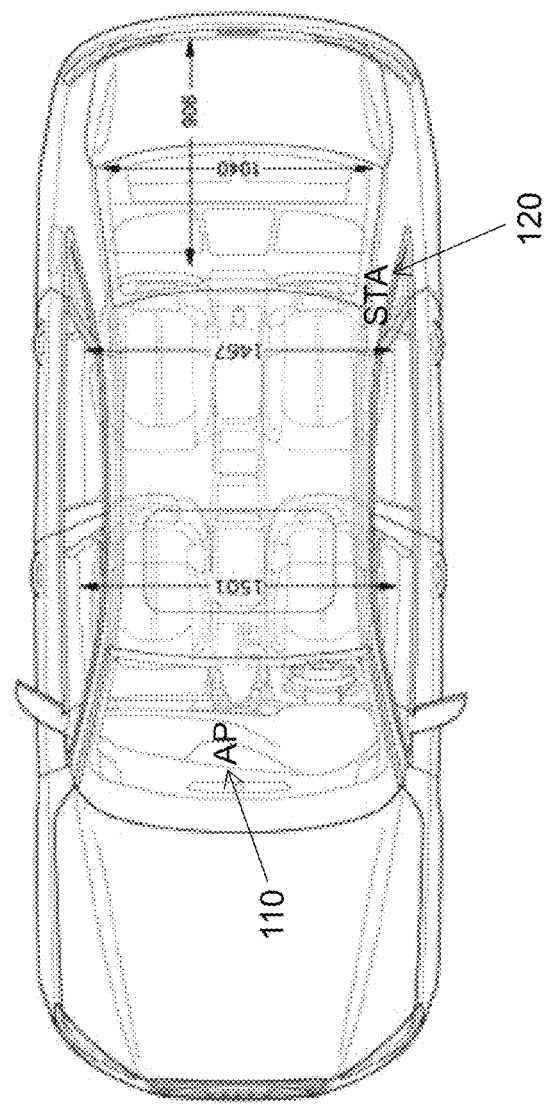
FIG. 1B illustrates a top perspective view of a car including a wireless vital sign detection system, according to some embodiments of the present disclosure.

One application of the wireless vital sign monitoring is a wireless based in-car human presence detection system 100, as illustrated in FIG. 1A and FIG. 1B. The system 100 includes an access point (AP) device 110 and a station (STA) device 120 coupled to a car. The STA device 120 may serve as a transmitter (or a Bot, or a Type 1 device) to transmit a wireless signal through a wireless channel in the car to the AP device 110 that serves as a receiver (or an Origin, or a Type 2 device). The received wireless signal differs from the transmitted wireless signal due to the wireless channel that may be impacted by any vital sign motion of a human being (e.g. a child) in the car. As such, the received wireless signal carries information of the vital sign motion, if presence, in the car. In some embodiments, the wireless signal may be a Wi-Fi signal. The detection may be applied to detect any vital sign (e.g. breathing or heartbeat or a periodic motion) of an object (e.g. a person, a user, a baby) in a venue (e.g. a vehicle) based on the channel information obtained from the received wireless signal.

FIG. 1A illustrates a side perspective view of a car including the system 100; while FIG. 1B illustrates atop perspective view of the car including the system 100, according to some embodiments of the present disclosure. As shown in FIG. 1A and FIG. 1B, the AP device 110 may be placed near the gear area or coupled to the dashboard; and the STA device 120 may be placed on the left side of the rear seat. This setting can generate a full coverage inside the car. In other embodiments, each of the AP device 110 and the STA device 120 may be placed at different locations in the car with same detection and operation method applied for wireless vital sign monitoring.

Figure 2:
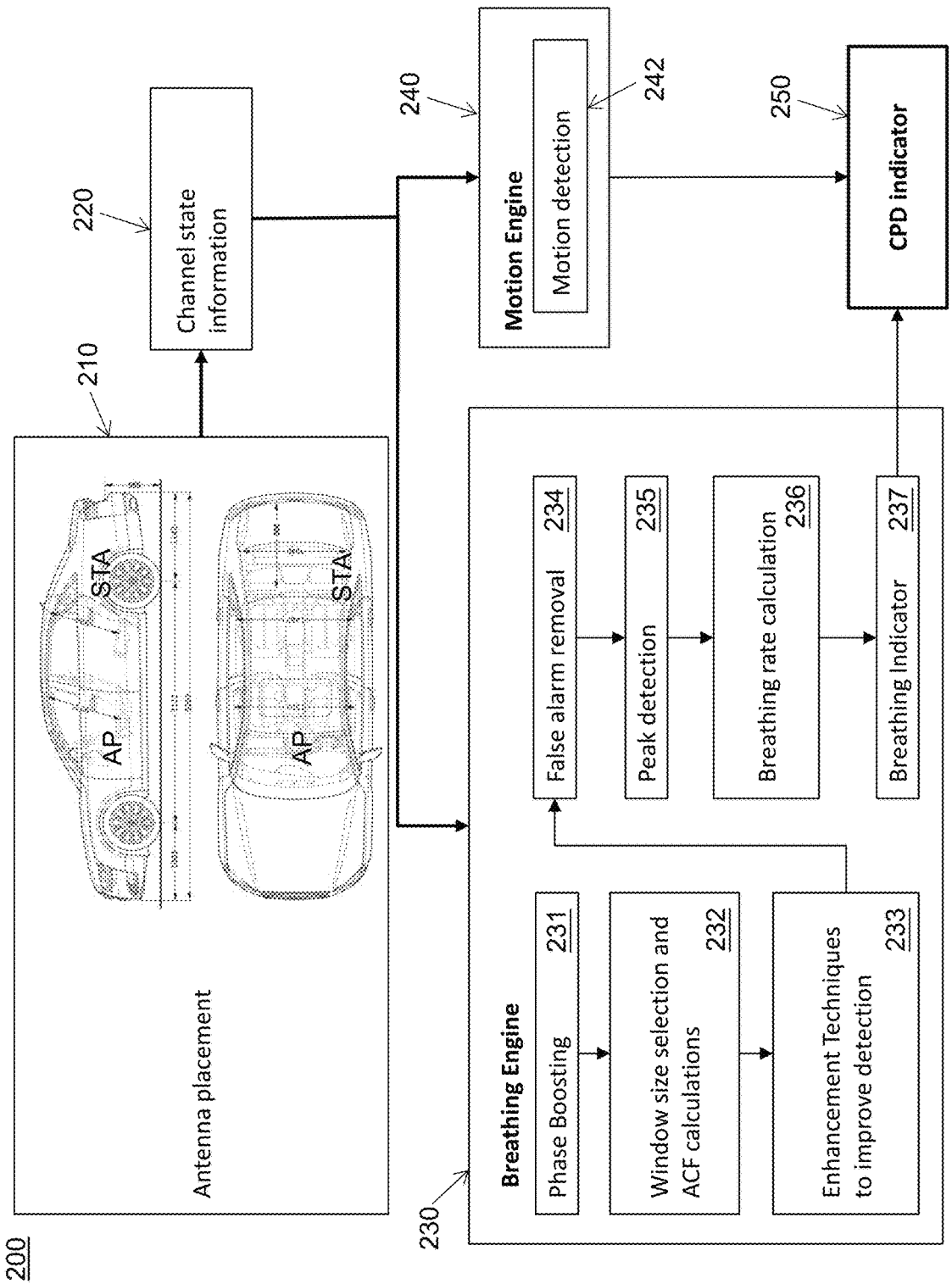
FIG. 2 illustrates a flow chart showing an exemplary method of a wireless vital sign detection system, according to some embodiments of the present disclosure.

FIG. 2 illustrates a flow chart showing an exemplary method 200 of a wireless vital sign detection system, e.g. the system 100 as shown in FIG. 1, according to some embodiments of the present disclosure. As shown in FIG. 2, after the AP and STA antennas are placed in a car and some initial set ups of the system at operation 210, the STA antenna can transmit a wireless signal, e.g. Wi-Fi signal, through a wireless channel in the car to the AP antenna. The received wireless signal may be used at operation 220 to capture channel state information (CSI) of the wireless channel in the car. If there is any living object (e.g. child) presence in the car, the captured CSI would include information of a periodic vital sign motion (e.g. breathing or heartbeat) of the living object. In addition, the captured CSI would also include information of any other motion (e.g. non-vital sign movement of the child) in the car.

In the example shown in FIG. 2, the obtained CSI is sent to a breathing engine 230 for detecting and monitoring breathing in the car; and is also sent to a motion engine 240 for detecting any non-vital sign motion in the car.

The breathing engine 230 in this example performs a series of operations 231-237. At operation 231, a phase boosting is applied on the obtained CSI. For example, the breathing engine 230 can compute a cleaned phase=$\angle H_{m_2,n}$ (f, t)−$\angle H_{m_1,n}$ (f, t). The cleaned phase may be added as an additional dimension to the CSI vector for phase boosting. In some embodiments, amplitude cleaning is not performed since it would remove the required information.

Then, the breathing engine 230 may perform (time) window size selection and autocorrelation function (ACF) calculations at operation 232. Window size selection is critical as it is directly related to initial detection delay. To detect the breathing rates correctly, a considerably long window size is desirable. On the other hand, longer window sizes would cause longer detection delays.

In some embodiments, changing or varying window sizes are used in the breathing engine 230 to achieve high performance as well as low detection delays. To reduce the initial delay, a small window size is used at the start of the engine 230. The window size is increased to the required length after the engine 230 stabilizes.

Then, the breathing engine 230 may perform enhancement techniques to improve detection at operation 233. The enhancement techniques may be applied to the ACF spectrum to enhance the breathing traces. These enhancement techniques may be image enhancement techniques including but not limited to: contrast stretching, slicing, histogram equalization, and some algorithms based on the retinex. For child presence detection (CPD) based on motion and breathing detection, image enhancement can also be applied to the ACF to make the peaks of the ACF more prominent, and thus the breathing rate more continuous, and thus the detection rate of CPD can be improved. In some embodiments, image enhancement can also be applied directly to the breathing estimation traces after spectral analysis/frequency components analysis of the time series of channel information. For example, the spectrograms on different transmitter-receiver links can each be enhanced across the different subcarriers and then combined.

In the example shown in FIG. 2, the enhancement techniques include the following. First, peak enhancement is performed on the ACF spectrum. Value k is selected from the experiments, such that enhanced ACF=ACF−k*diff(ACF), where diff(ACF) means the difference between adjacent values of the ACF signal. After enhancement, the signal is normalized to the [0, 1] range. Then, histogram equalization may be performed on the normalized peak enhanced signal.

Figure 3:
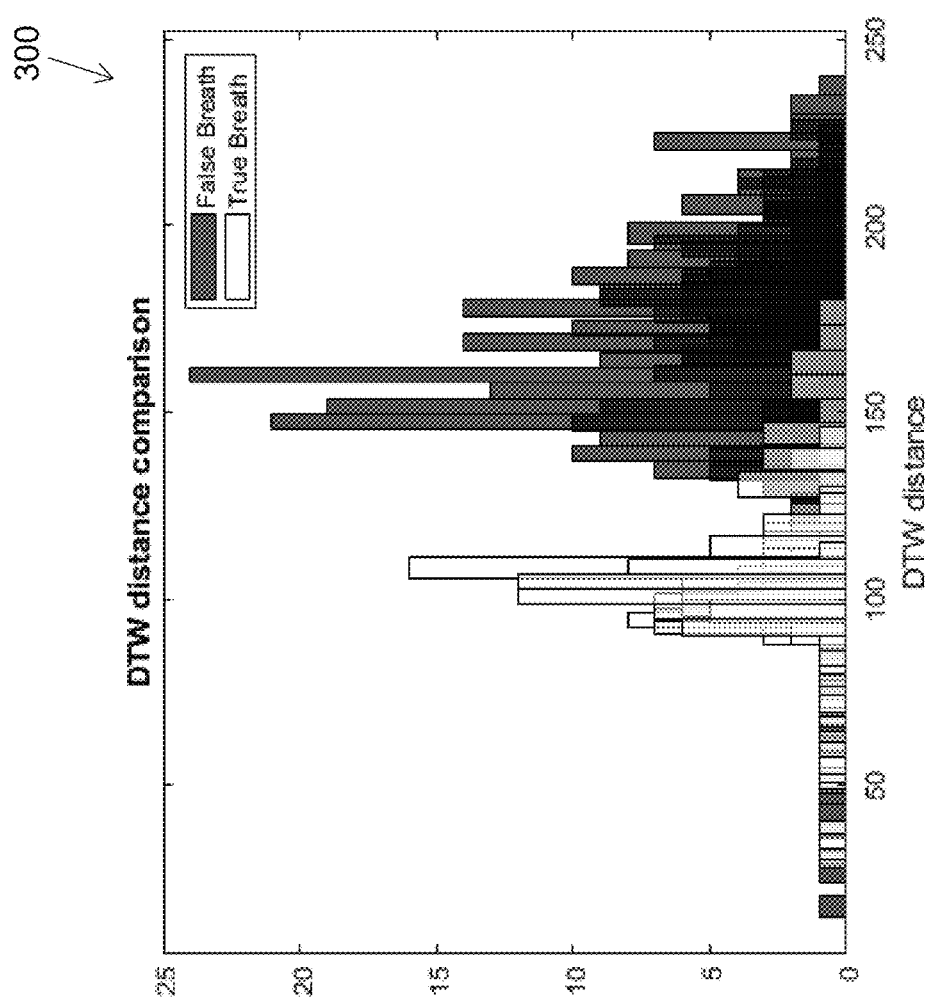
FIG. 3 illustrates an exemplary distribution of dynamic time warping (DTW) values during a breathing detection, according to some embodiments of the present disclosure.

Then, the breathing engine 230 may perform false alarm removal at operation 234. In some embodiments, there are two types of false alarm removal using two techniques. Dynamic time warping (DTW) may be used to measure the similarity between a given breathing signal and extracted breathing signal from the engine 230. If the extracted breathing signal corresponds to true breathing, the DTW value will be low compared to the false breath. FIG. 3 depicts the DTW value distribution 300 for true breathing and false breathing, according to some embodiments of the present disclosure. FIG. 3 may be used to determine the DTW threshold value.

In addition, to evaluate the noise level, the number of zero crossings for the extracted signals may be calculated. A high number of zero crossings are expected for false breathing signals as false breathing exhibits higher oscillations than true breathing signals. In some embodiments, extracted breathing signals are in the range of 0-1. Thus, one can consider 0.5 as the 0-th level when calculating the number of zero crossings.

Then, the breathing engine 230 may perform peak detection at operation 235. In some embodiments, if the difference between two consecutive peaks is in the range of the breathing cycle, those peaks are considered as the potential peaks to calculate the breathing rate.

Then, the breathing engine 230 may perform breathing rate calculation at operation 236. In some embodiments, breathing rate is calculated by the difference between two detected peaks from operation 235.

Then, the breathing engine 230 may generate a breathing indicator at operation 237. In some embodiments, if there are more than two/three/five breathing rates detected in a 10-sec window, it is indicated that a breathing is detected.

The breathing indicator may be sent to the operation child presence detection (CPD) indicator 250 to determine whether there is a child presence in the car. The CPD indicator 250 may be generated based on the breathing detection result from the breathing engine 230, as well as a motion detection result from the motion engine 240. The motion engine 240 may perform motion detection operation 242 based on the obtained CSI, to detect any non-breathing or non-vital motion in the car. In some embodiments, if breathing and/or motion is detected, the system indicates the presence of a baby inside the car.

This Wi-Fi based in-car CPD system utilizing the above described method has a higher performance capability than other Wi-Fi based CPD systems. The approach is robust to severe environmental conditions such as heavy rain, busy traffic around the car. Some image enhancement methods are utilized to increase the detection capabilities, while false alarm removal methods can make the system free of false detections.

In some embodiments, variable window length, instead of fixed window length, is used to calculate the breathing spectrum. Instead of using ACF spectrum directly, the system can employ image enhancement techniques including peak enhancement and histogram equalization to improve the detection performance. During the false alarm removal step, the system may utilize DTW to evaluate structural similarity between true breathing signal and estimated signal, and utilize the number of zero crossing to determine a noise level.

Figure 4:
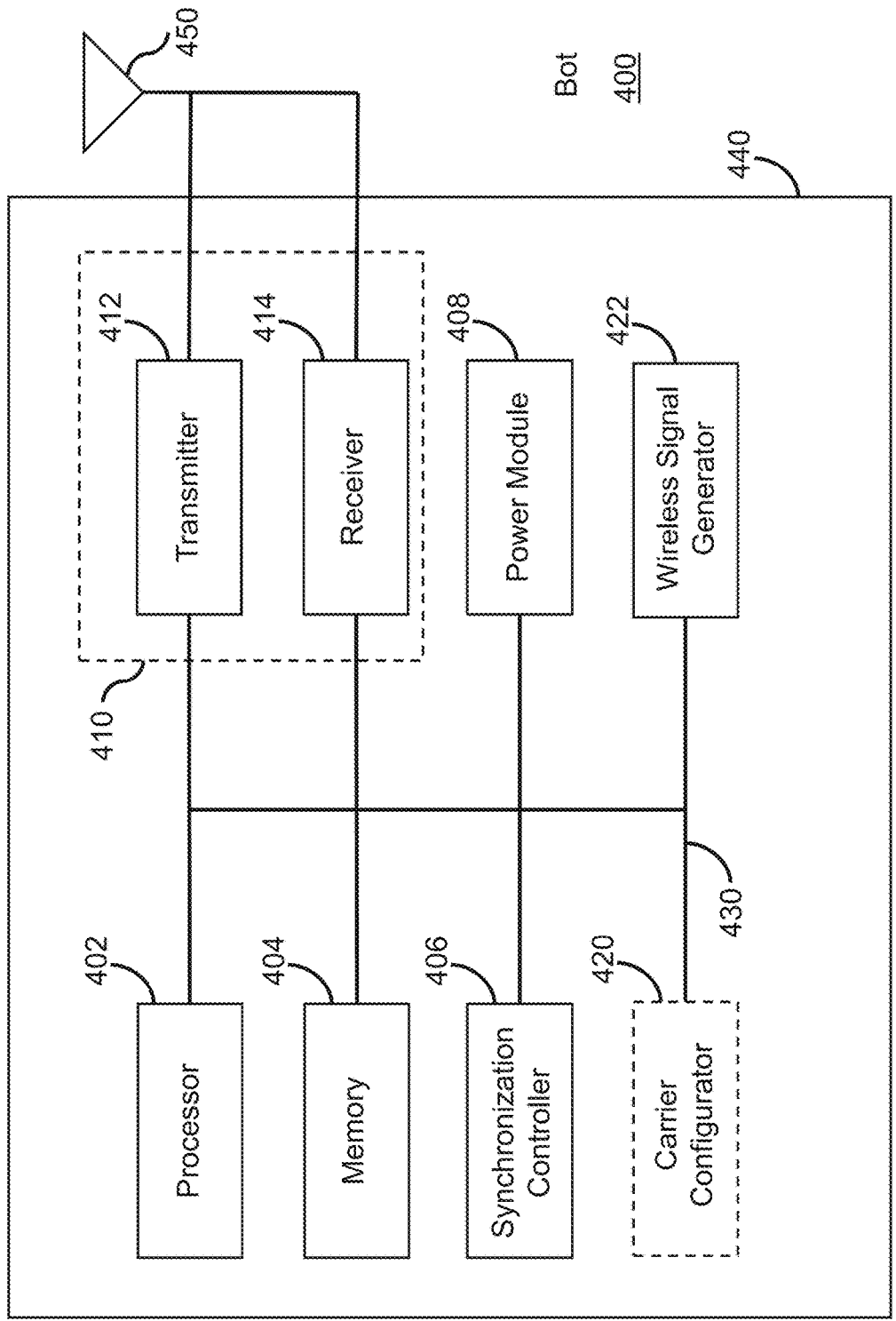
FIG. 4 illustrates an exemplary block diagram of a first wireless device of a system for wireless vital sign monitoring, according to some embodiments of the present disclosure.

FIG. 4 illustrates an exemplary block diagram of a first wireless device, e.g. a Bot 400, of a system for radio-assisted signal estimation, according to some embodiments of the present disclosure. The Bot 400 is an example of a device that can be configured to implement the various methods described herein. As shown in FIG. 4, the Bot 400 includes a housing 440 containing a processor 402, a memory 404, a transceiver 410 comprising a transmitter 412 and receiver 414, a synchronization controller 406, a power module 408, an optional carrier configurator 420 and a wireless signal generator 422.

In this embodiment, the processor 402 controls the general operation of the Bot 400 and can include one or more processing circuits or modules such as a central processing unit (CPU) and/or any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable circuits, devices and/or structures that can perform calculations or other manipulations of data.

The memory 404, which can include both read-only memory (ROM) and random access memory (RAM), can provide instructions and data to the processor 402. A portion of the memory 404 can also include non-volatile random access memory (NVRAM). The processor 402 typically performs logical and arithmetic operations based on program instructions stored within the memory 404. The instructions (a.k.a., software) stored in the memory 404 can be executed by the processor 402 to perform the methods described herein. The processor 402 and the memory 404 together form a processing system that stores and executes software. As used herein, "software" means any type of instructions, whether referred to as software, firmware, middleware, microcode, etc. which can configure a machine or device to perform one or more desired functions or processes. Instructions can include code (e.g., in source code format, binary code format, executable code format, or any other suitable format of code). The instructions, when executed by the one or more processors, cause the processing system to perform the various functions described herein.

The transceiver 410, which includes the transmitter 412 and receiver 414, allows the Bot 400 to transmit and receive data to and from a remote device (e.g., an Origin or another Bot). An antenna 450 is typically attached to the housing 440 and electrically coupled to the transceiver 410. In various embodiments, the Bot 400 includes (not shown) multiple transmitters, multiple receivers, and multiple transceivers. In one embodiment, the antenna 450 is replaced with a multi-antenna array 450 that can form a plurality of beams each of which points in a distinct direction. The transmitter 412 can be configured to wirelessly transmit signals having different types or functions, such signals being generated by the processor 402. Similarly, the receiver 414 is configured to receive wireless signals having different types or functions, and the processor 402 is configured to process signals of a plurality of different types.

The Bot 400 in this example may serve as Bot or AP 110 in FIG. 1A and FIG. 1B for wireless vital sign monitoring in a venue. For example, the wireless signal generator 422 may generate and transmit, via the transmitter 412, a wireless signal through a wireless channel in the venue. The received wireless signal would carry channel information of the wireless channel. Because the wireless channel is impacted by any vital sign motion (e.g. breathing, heartbeat, etc.) of an object in the venue, the channel information includes vital sign information from the object. As such, a vital sign can be detected and monitored based on channel information obtained from the received wireless signal. The generation of the wireless signal at the wireless signal generator 422 may be based on a request for wireless vital sign monitoring from another device, e.g. an Origin, or based on a system pre-configuration. That is, the Bot 400 may or may not know that the wireless signal transmitted will be used for wireless vital sign monitoring.

The synchronization controller 406 in this example may be configured to control the operations of the Bot 400 to be synchronized or un-synchronized with another device, e.g. an Origin or another Bot. In one embodiment, the synchronization controller 406 may control the Bot 400 to be synchronized with an Origin that receives the wireless signal transmitted by the Bot 400. In another embodiment, the synchronization controller 406 may control the Bot 400 to transmit the wireless signal asynchronously with other Bots. In another embodiment, each of the Bot 400 and other Bots may transmit the wireless signals individually and asynchronously.

The carrier configurator 420 is an optional component in Bot 400 to configure transmission resources, e.g. time and carrier, for transmitting the wireless signal generated by the wireless signal generator 422. In one embodiment, each CI of the time series of CI has one or more components each corresponding to a carrier or sub-carrier of the transmission of the wireless signal. The wireless sound sensing may be based on any one or any combination of the components.

The power module 408 can include a power source such as one or more batteries, and a power regulator, to provide regulated power to each of the above-described modules in FIG. 4. In some embodiments, if the Bot 400 is coupled to a dedicated external power source (e.g., a wall electrical outlet), the power module 408 can include a transformer and a power regulator.

The various modules discussed above are coupled together by a bus system 430. The bus system 430 can include a data bus and, for example, a power bus, a control signal bus, and/or a status signal bus in addition to the data bus. It is understood that the modules of the Bot 400 can be operatively coupled to one another using any suitable techniques and mediums.

Although a number of separate modules or components are illustrated in FIG. 4, persons of ordinary skill in the art will understand that one or more of the modules can be combined or commonly implemented. For example, the processor 402 can implement not only the functionality described above with respect to the processor 402, but also implement the functionality described above with respect to the wireless signal generator 422. Conversely, each of the modules illustrated in FIG. 4 can be implemented using a plurality of separate components or elements.

Figure 5:
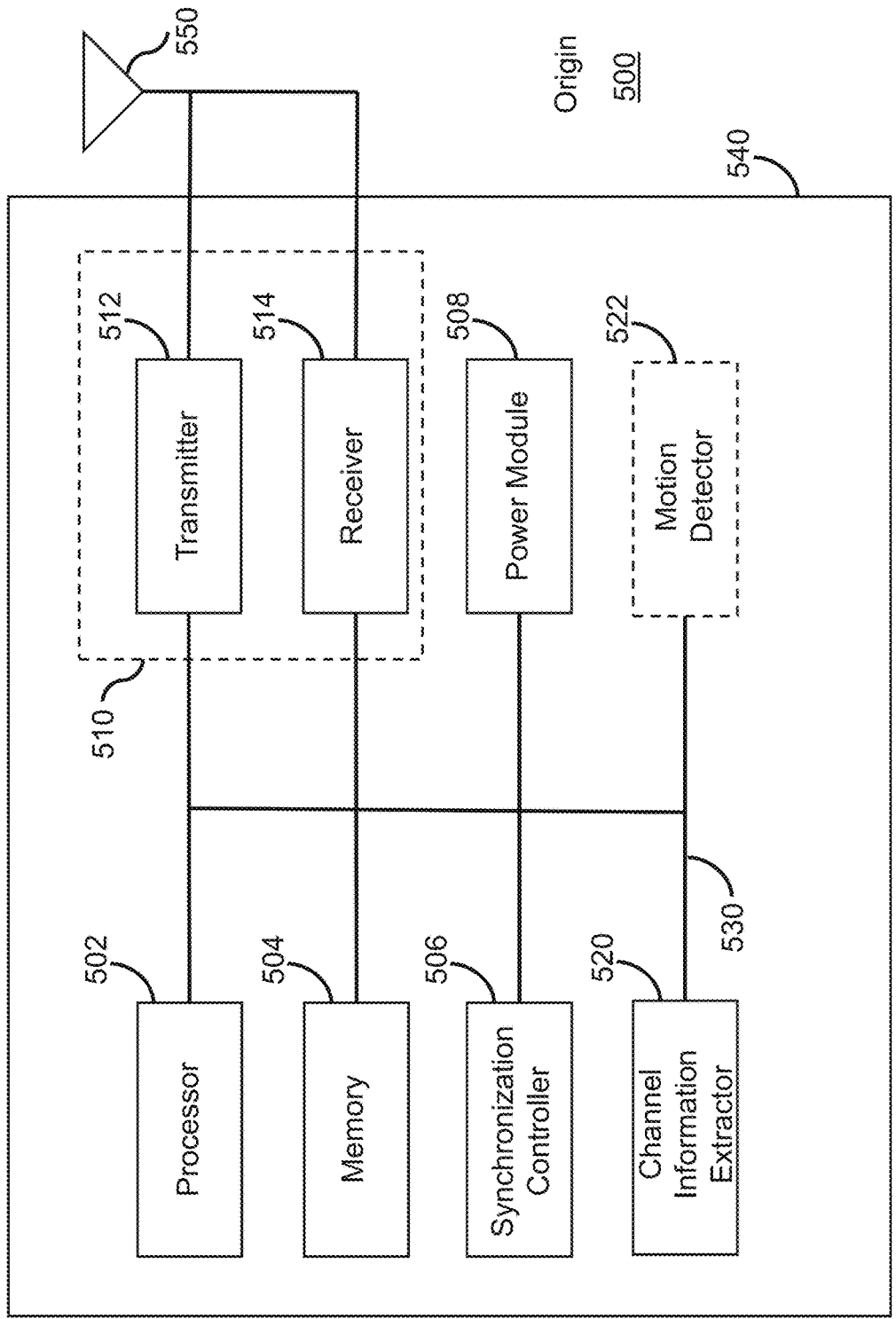
FIG. 5 illustrates an exemplary block diagram of a second wireless device of a system for wireless vital sign monitoring, according to some embodiments of the present disclosure.

FIG. 5 illustrates an exemplary block diagram of a second wireless device, e.g. an Origin 500, of a system for radio-assisted signal estimation, according to one embodiment of the present teaching. The Origin 500 is an example of a device that can be configured to implement the various methods described herein. The Origin 500 in this example may serve as Origin or STA 120 in FIG. 2 for wirelessly vital sign monitoring in a venue. As shown in FIG. 5, the Origin 500 includes a housing 540 containing a processor 502, a memory 504, a transceiver 510 comprising a transmitter 512 and a receiver 514, a power module 508, a synchronization controller 506, a channel information extractor 520, and an optional motion detector 522.

In this embodiment, the processor 502, the memory 504, the transceiver 510 and the power module 508 work similarly to the processor 402, the memory 404, the transceiver 410 and the power module 408 in the Bot 400. An antenna 550 or a multi-antenna array 550 is typically attached to the housing 540 and electrically coupled to the transceiver 510.

The Origin 500 may be a second wireless device that has a different type from that of the first wireless device (e.g. the Bot 400). In particular, the channel information extractor 520 in the Origin 500 is configured for receiving the wireless signal through the wireless channel, and obtaining a time series of channel information (CI) of the wireless channel based on the wireless signal. The channel information extractor 520 may send the extracted CI to the optional motion detector 522 or to a motion detector outside the Origin 500 for wireless sound sensing in the venue.

The motion detector 522 is an optional component in the Origin 500. In one embodiment, it is within the Origin 500 as shown in FIG. 5. In another embodiment, it is outside the Origin 500 and in another device, which may be a Bot, another Origin, a cloud server, a fog server, a local server, and an edge server. The optional motion detector 522 may be configured for detecting sound information from a vibrating object or source in the venue based on motion information. The motion information may be computed based on the time series of CI by the motion detector 522 or another motion detector outside the Origin 500.

The synchronization controller 506 in this example may be configured to control the operations of the Origin 500 to be synchronized or un-synchronized with another device, e.g. a Bot, another Origin, or an independent motion detector. In one embodiment, the synchronization controller 506 may control the Origin 500 to be synchronized with a Bot that transmits a wireless signal. In another embodiment, the synchronization controller 506 may control the Origin 500 to receive the wireless signal asynchronously with other Origins. In another embodiment, each of the Origin 500 and other Origins may receive the wireless signals individually and asynchronously. In one embodiment, the optional motion detector 522 or a motion detector outside the Origin 500 is configured for asynchronously computing respective heterogeneous motion information based on the respective time series of CI.

The various modules discussed above are coupled together by a bus system 530. The bus system 530 can include a data bus and, for example, a power bus, a control signal bus, and/or a status signal bus in addition to the data bus. It is understood that the modules of the Origin 500 can be operatively coupled to one another using any suitable techniques and mediums.

Although a number of separate modules or components are illustrated in FIG. 5, persons of ordinary skill in the art will understand that one or more of the modules can be combined or commonly implemented. For example, the processor 502 can implement not only the functionality described above with respect to the processor 502, but also implement the functionality described above with respect to the channel information extractor 520. Conversely, each of the modules illustrated in FIG. 5 can be implemented using a plurality of separate components or elements.

Figure 6:
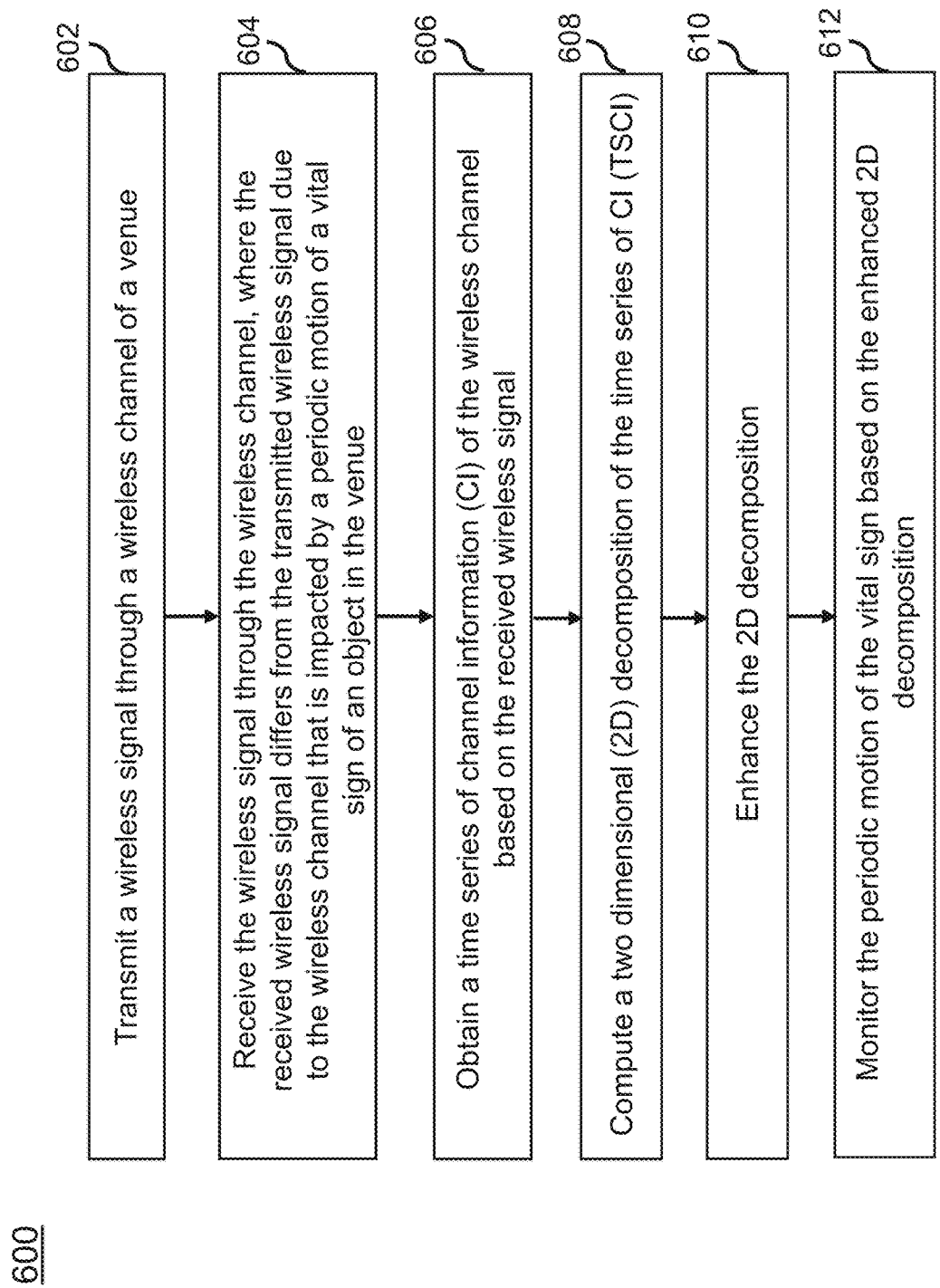
FIG. 6 illustrates a flow chart of an exemplary method for radio-assisted signal estimation, according to some embodiments of the present disclosure.

FIG. 6 illustrates a flow chart of an exemplary method 600 for radio-assisted signal estimation, according to some embodiments of the present disclosure. In various embodiments, the method 600 can be performed by the systems disclosed above. At operation 602, a wireless signal is transmitted through a wireless channel of a venue. At operation 604, the wireless signal is received through the wireless channel. The received wireless signal differs from the transmitted wireless signal due to the wireless channel that is impacted by a periodic motion of a vital sign of an object in the venue. At operation 606, a time series of channel information (CI) of the wireless channel is obtained based on the received wireless signal. At operation 608, a two dimensional (2D) decomposition of the time series of CI (TSCI) is computed. Then the 2D decomposition is enhanced at operation 610. At operation 612, the periodic motion of the vital sign is monitored based on the enhanced 2D decomposition. The order of the operations in FIG. 6 may be changed according to various embodiments of the present teaching.

In some embodiments, vital sign detection is based on 2D decomposition of TSCI obtained from wireless sounding signal from a Type 1 device to a Type 2 device.

The following numbered clauses provide examples for wireless vital sign monitoring.

Clause 1. A method/device/system/software of a wireless vital sign monitoring system, comprising: transmitting a wireless signal from a Type 1 heterogeneous wireless device of the wireless sensing system through a wireless multipath channel of a venue, wherein the wireless multipath channel is impacted by a vital sign motion of an object in the venue; receiving the wireless signal by a Type2 heterogeneous wireless device of the system through the wireless multipath channel, wherein the received wireless signal differs from the transmitted wireless signal due to the wireless multipath channel of the venue and the periodic vital sign motion of the object; obtaining a time series of channel information (CI) of the wireless multipath channel based on the received wireless signal using a processor, a memory and a set of instructions; computing a two dimensional (2D) decomposition of the time series of CI (TSCI); enhancing the 2D decomposition; monitoring the vital sign motion based on the enhanced 2D decomposition.

Clause 2. The method/device/system/software of the wireless vital sign monitoring system of clause 1, comprising: computing a time series of CI-feature (TSCF) based on the TSCI, each CI-feature (CF) comprising a concatenation of a basic feature of a respective CI and another basic feature of a corresponding denoised CI, wherein the basic feature of any CI comprises at least one of: the CI, a magnitude of the CI, a phase of the CI, a magnitude of a component of the CI (CI-component), a phase of the component of the CI, a function of a magnitude, or a function of a phase, wherein the denoised CI is computed by processing the TSCI with a first denoising filter, the first denoising filter comprising at least one of: a low-pass filter, a bandpass filter, a highpass filter, a weighted sum, a weighted difference, a weighted average, a median filter, a percentile filter, a CI-component-wise denoising filter; computing the 2D decomposition based on the TSCF.

In some embodiments, the system can compute 1D characteristic function for each sliding time window, and construct 2D decomposition based on the 1D characteristic function.

Clause 3. The method/device/system/software of the wireless vital sign monitoring system of clause 2, comprising: determining a series of sliding time windows, each sliding time window associated with a time stamp; computing a respective one dimensional (1D) characteristic function of the CF of the TSCF in each sliding time window; constructing the 2D decomposition based on the respective 1D characteristic function in each sliding time window.

In some embodiments, the system can compute 1D characteristic function based on a transformation such as ACF or STFT.

Clause 4. The method/device/system/software of the wireless vital sign monitoring system of clause 3, comprising: computing the respective 1D characteristic function based on a transformation of the CF of the TSCF in the respective sliding time window, wherein the transformation comprises at least one of: a frequency transformation, a transformation to frequency domain, a short-time Fourier transform (STFT), a wavelet transform, a filter-bank representation, a spectral analysis, a harmonic analysis, a Fourier analysis, a multi-resolution analysis, a time transformation, a transformation to a time-shift domain, an auto-correlation function (ACF), an auto-covariance function, a time-frequency decomposition, a time-frequency representation, or a spectrogram.

In some embodiments, the system can line up and align 1D characteristic function to construct a 2D matrix which is the 2D decomposition.

Clause 5. The method/device/system/software of the wireless vital sign monitoring system of clause 4, comprising: constructing a 2D matrix by lining up the 1D characteristic functions in time order in accordance with the associated time stamp and aligning them, wherein the i-th column of the 2D matrix is the 1D characteristic function associated with the i-th sliding time window, wherein the j-th row of the 2D matrix is associated with a time-shift of j time units, wherein the matrix element at i-th column and j-th row is the value of the 1D characteristic function in the i-th sliding time window with a time-shift of j time units, wherein the 2D matrix is the 2D decomposition.

In some embodiments, the system can enhance (process) 2D matrix with vertical highpass filtering and horizontal lowpass filter.

Clause 6. The method/device/system/software of the wireless vital sign monitoring system of clause 5, comprising: enhancing the 2D decomposition by applying to each matrix element of the 2D matrix either vertical highpass filtering, or horizontal lowpass filtering, or both.

In some embodiments, the filter may be 2D filter, which may be separable into a 1D vertical filter and a 1D horizontal filter. Different matrix elements may have different filter.

Clause 7. The method/device/system/software of the wireless vital sign monitoring system of clause 6, comprising: filtering each matrix element of the 2D matrix with a respective 2D vertical highpass horizontal lowpass filter, wherein the 2D filter is one of: separable or non-separable, wherein the 2D filter is either linear or nonlinear.

In some embodiments, the filter may be separable such that the 2D filter is decomposed into a 1D vertical highpass filter and a 1D horizontal lowpass filter.

Clause 8. The method/device/system/software of the wireless vital sign monitoring system of clause 7, comprising: enhancing the 2D decomposition by at least one of: filtering each matrix element of the 2D matrix with a respective vertical highpass filter, or filtering each matrix element of the 2D matrix with a respective horizontal lowpass filter, wherein any filter is either linear or nonlinear.

In some embodiments, same vertical highpass filter is for a whole column/part of a column, or a whole row/part of a row; or same horizontal lowpass filter is for a whole column/part of a column, or a whole row/part of a row.

Clause 9. The method/device/system/software of the wireless vital sign monitoring system of clause 8, comprising: enhancing the 2D decomposition by at least one of: filtering part of each column of the 2D matrix with a respective first common vertical highpass filter, or filtering part of each row of the 2D matrix with a respective second common vertical highpass filter, or filtering part of each column of the 2D matrix with a respective first common horizontal lowpass filter, or filtering part of each row of the 2D matrix with a respective second common horizontal lowpass filter.

In some embodiments, vertical highpass filter is a 1D filter applied in either vertical direction or near-vertical direction.

Clause 10. The method/device/system/software of the wireless vital sign monitoring system of clause 8, comprising: wherein a vertical highpass filter is a directional 1D highpass filter applied in the vertical direction or in a near-vertical direction.

In some embodiments, horizontal lowpass filter is a 1D filter applied in either horizontal direction or near-horizontal direction.

Clause 11. The method/device/system/software of the wireless vital sign monitoring system of clause 8, comprising: wherein a horizontal lowpass filter is a directional 1D lowpass filter applied in the horizontal direction or in a near-horizontal direction.

In some embodiments, there may be a succession of two or more filters, each being either vertical highpass or horizontal lowpass.

Clause 12. The method/device/system/software of the wireless vital sign monitoring system of clause 8, comprising: filtering each matrix element of the 2D matrix with a succession of at least two 1D filters, each being either vertical highpass filter or horizontal lowpass filter.

In some embodiments, histogram equalization is performed.

Clause 13. The method/device/system/software of the wireless vital sign monitoring system of clause 8, comprising: enhancing the 2D decomposition by applying histogram equalization to a number of consecutive columns of the 2D matrix.

In some embodiments, the system can compute matching score based on DTW. If matching score is larger than a threshold (i.e. bad match), there is no vital sign present.

Clause 14. The method/device/system/software of the wireless vital sign monitoring system of clause 13, comprising: computing a distance score based on dynamic time warping (DTW) between a reference column and a particular column of the enhanced 2D matrix associated with a particular time, wherein the reference column is computed in a training session by clustering a number of training columns matched based on DTW, wherein the training columns are computed based on training TSCI obtain from received training wireless signals transmitted when training objects with vital sign are present; if the distance score is larger than a first threshold, the vital sign motion of the object is tentatively not detected at the particular time.

In some embodiments, the system can compute zero crossing score. If zero crossing score is larger than a threshold (i.e. noisy), there is no vital sign present.

Clause 15. The method/device/system/software of the wireless vital sign monitoring system of clause 14, comprising: subtracting a quantity from each matrix element in the particular column of the enhanced 2D matrix; computing a zero-crossing count of the particular column; if the zero-crossing count is larger than a second threshold, the vital sign motion of the object is tentatively not detected at the particular time.

In some embodiments, the system can compute inter-peak distance. If inter-peak distance is not inside acceptable range, there is no vital sign present. If the inter-peak distance is inside acceptable range, vital sign is detected. Period/frequency of detected vital sign may be computed based on the inter-peak distance.

Clause 16. The method/device/system/software of the wireless vital sign monitoring system of clause 15, comprising: computing more than one peaks (local maxima) of the particular column of the enhanced 2D matrix; computing an inter-peak distance based on the more than one peaks; If the inter-peak distance is in an acceptable range, the vital sign motion of the object is tentatively detected at the particular time and one of: a frequency or a period, of the vital sign is equal to the inter-peak distance; If the inter-peak distance is not in an acceptable range, the vital sign motion of the object is tentatively not detected at the particular time.

In some embodiments, vital sign is detected if it is tentatively detection at a percentage higher than a threshold.

Clause 17. The method/device/system/software of the wireless vital sign monitoring system of clause 16, comprising: detecting the vital sign motion of the object if A is larger than a third threshold, wherein A is the percentage of vital sign being tentatively detected in a period of time.

In some embodiments, the system can detect voice activity based on radio signal (i.e. based on CI obtained from received radio signal) without using any media input (e.g. video, or image/visual, or audio or speech or sound) or any data transmitted in the radio signal by transmitter (Type 1 device).

Clause 18. A method/device/system/software of a wireless vital sign monitoring system, comprising: detecting voice activity based on a radio signal using a processor, a memory and a set of instruction of a device of the system, without using any media signal.

In some embodiments, radio signal is transmitted by Type 1 device and received by Type 2 device. TSCI obtained in Type 2 device based on received radio signal.

Clause 19. The method/device/system/software of the wireless vital sign monitoring system of clause 18, comprising: wherein the radio signal is a wireless signal transmitted by a Type 1 heterogeneous wireless device of the system in a venue; wherein the radio signal is received by a Type 2 heterogeneous wireless device of the system through a wireless multipath channel of the venue, wherein the wireless multipath channel is impacted by the voice activity in the venue; obtaining a time series of channel information (CI) of the wireless multipath channel based on the received radio signal; detecting the voice activity based on the time series of CI (TSCI) of the wireless multipath channel.

Clause 20. The method/device/system/software of the wireless vital sign monitoring system of clause 19, further comprising: wherein the radio signal comprises at least one of: a data communication signal, a wireless network signal, a standard compliant signal, a wireless local area network (WLAN) signal, a WiFi signal, an IEEE 802 signal, an IEEE 802.11 signal, an IEEE 802.1 1bf signal, an IEEE 802.11 directional multi-gigabit (DMG) signal, a wireless communication network signal, a 3GPP signal, a 4G/LTE/5G/6G/7G/8G signal, a wireless sensing signal, a wireless sounding signal, a radar signal, a millimeter wave (mmWave) signal, a UWB signal, or a electromagnetic signal above 40 kHz; wherein the media signal comprises at least one of: a microphone signal, a speech signal, a vocal signal, an audio signal, a signal less than 40 kHz, an acoustic signal, an audible signal, a telephone signal, a tele-conferencing signal, an audio-telephony signal, a conference call signal, a visual signal, a video signal, a video-telephony signal, a video-conferencing signal, a media streaming signal, or a multimedia signal.

In some embodiments, no data payload in radio signal is used.

Clause 21. The method/device/system/software of the wireless vital sign monitoring system of clause 20, comprising: wherein the radio signal is a data communication signal; detecting the voice activity without using any data payload communicated in the data communication signal.

In some embodiments, no media data in radio signal is used.

Clause 22. The method/device/system/software of the wireless vital sign monitoring system of clause 21, comprising: detecting the voice activity without using any media signal data communicated in the data communication signal.

In some embodiments, voice activity is produced by target voice source.

Clause 23. The method/device/system/software of a wireless vital sign monitoring system of clause 22, comprising: detecting the voice activity of a target voice source in the venue based on the radio signal, wherein the wireless multipath channel is impacted by a voice producing motion of the target voice source.

In some embodiments, the voice-related radio feature (TSRF) is bandlimited. Telephone speech signal may be bandlimited 4 kHz. Speech signal may be bandlimited to 7 kHz. Audio may be bandlimited to 20 kHz. TSRF may be bandlimited to half of sounding frequency, which may be half of 1/10/100/1000/10000/100000/1000000 Hz. To play safe here, TSRF may be bandlimited to 1 Mhz. It can be bandlimited to 100 kHz, or 10 kHz also.

Clause 24. The method/device/system/software of a wireless vital sign monitoring system of clause 23, comprising: computing a time series of radio feature (TSRF) based on the TSCI, each radio feature (RF) of the TSRF being computed based on a respective sliding window of the TSCI, wherein the TSRF is a baseband signal bandlimited to 1 MHz; detecting the voice activity based on the TSRF.

In some embodiments, the system can detect voice activity by detecting voice-related characteristics (e.g. pitch, harmonics of the pitch, time profile of pitch) that suggests the presence of voice/speech.

Clause 25. The method/device/system/software of a wireless vital sign monitoring system of clause 24, comprising: detecting a voice-related characteristics in the TSRF; detecting the voice activity based on the detected voice-related characteristics in the TSRF.

In some embodiments, there are many voice-related characteristics listed here that may be manifested in the TSRF (e.g. pitch, pitch profile, inter-mixed voice/unvoiced speech, etc.). These voice characteristics differentiate voice from non-voice (e.g. machine sound, wind sound, environmental sound, etc.). In particular, voiced speech (e.g. vowel, some consonants, liquid, etc.) has pitch. Unvoiced speech (e.g. most consonants, fricative, plosive) has no pitch. Vowels are voiced sound. Typical human pitch goes between 50 Hz and 250 Hz.

Clause 26. The method/device/system/software of a wireless vital sign monitoring system of clause 25, further comprising: wherein the voice-related characteristics comprises at least one of the following characteristics: a speech feature, a vowel, a consonant, a fricative, an affricate, a plosive, a nasal, an approximant, a liquid, a lateral, bilabial sound, velar sound, alveolar sound, a phone, a phoneme, voiced sound, unvoiced sound, a pitch of voiced speech, a foundation frequency, a voice-related frequency range, at least one harmonics of voiced-speech, at least one formant of speech, a time-varying pitch, a pitch profile, a voice-related time trend of pitch, a tone, a prosodic feature, a sequence of intermittent voiced and unvoiced sound, a musical feature, a speech timing, a speech pacing, a musical timing, a musical pacing, or an environmental sound.

In some embodiments, there is an instantaneous pitch at a current time, which may be observable in TSRF.

Clause 27. The method/device/system/software of a wireless vital sign monitoring system of clause 26, further comprising: detecting an instantaneous pitch associated with a current time instance in the TSRF, wherein an instantaneous fundamental frequency associated with the instantaneous pitch is greater than a lower threshold and less than a upper threshold; detecting the voice activity based on the detected instantaneous pitch.

Human speech often has many harmonics. Some harmonics may be observable in TSRF.

Clause 28. The method/device/system/software of a wireless vital sign monitoring system of clause 27, further comprising: detecting at least one instantaneous harmonics of the instantaneous pitch associated with the current time instance in the TSRF, wherein a frequency associated with each respective harmonics is an integer multiple of the instantaneous fundamental frequency of the instantaneous pitch; detecting the voice activity based on the detected instantaneous harmonic of the pitch.

Besides having an instantaneous pitch, human speech has a time-varying pitch. The human speech may use the time-varying pitch to express many things: tones in a tonal language, prosidy, vowel pronunciation, consonant pronunciation, etc. The time-varying pitch may comprise pitches within a certain time window.

Clause 29. The method/device/system/software of a wireless vital sign monitoring system of clause 28, further comprising: detecting a pitch profile comprising a plurality of instantaneous pitches associated with a plurality of respective time instances in the TSRF, wherein each instantaneous pitch associated with a respective time instance is associated with a respective instantaneous fundamental frequency greater than the lower threshold and less than the upper threshold; detecting a voice-related time trend of the plurality of instantaneous pitches in the pitch profile; detecting the voice activity based on the detected pitch profile and the detected voice-related time trend of the instantaneous pitches.

In some embodiments, there are some linguistically/phonetically meaningful time trends of the time-varying pitch.

Clause 30. The method/device/system/software of a wireless vital sign monitoring system of clause 29, further comprising: wherein the time trend comprises at least one of: a local continuity of instantaneous pitches, a local continuity of the instantaneous frequencies, a local continuity of frequency of the instantaneous harmonics, a habitual pitch, a long term pitch, a variation of pitch around the habitual pitch, a timing or pacing of pitch change, a fast pitch change within a tone, or a slow pitch change reflecting prosody.

In some embodiments, the voice-related characteristics may be detected in time domain using neural network.

Clause 31. The method/device/system/software of a wireless vital sign monitoring system of clause 30, further comprising: processing the TSRF with a neural network; detecting the voice-related characteristics based on the neural network processing of the TSFR.

In some embodiments, the voice-related characteristics may be detected in frequency domain; and the system can perform frequency decomposition of TSRF.

Clause 32. The method/device/system/software of a wireless vital sign monitoring system of clause 30, further comprising: computing a frequency decomposition of the TSRF by computing at least one of: a spectrogram, a short-time Fourier transform (STFT), a wavelet transform, a filter-bank representation, a harmonic analysis, a Fourier analysis, a multi-resolution analysis, a time-frequency decomposition, a time-frequency representation, a sonograph, a voiceprint, a voicegram, or a waterfall display; detecting the voice-related characteristics based on the frequency decomposition.

In some embodiments, the voice-related characteristics may be detected in frequency domain using neural network. An optional feature is to apply "overlap and concatenate" on the frequency decomposition to generate input to the neural network.

Clause 33. The method/device/system/software of a wireless vital sign monitoring system of clause 32, further comprising: processing the frequency decomposition of the TSRF with a neural network; detecting the voice-related characteristics based on the neural network processing of the frequency decomposition of the TSRF.

In some embodiments, the voice-related characteristics may be detected in frequency domain using some algorithm (i.e. not using neural network). The algorithm may detect the manifestation (e.g. pitch, harmonics, local continuity) of the voice-related characteristics in the TSRF.

Clause 34. The method/device/system/software of a wireless vital sign monitoring system of clause 32, further comprising: wherein the voice-related characteristics comprises a pitch of the voice activity; detecting an instantaneous pitch based on the frequency decomposition of the TSRF in a time window associated with the current time instance.

In some embodiments, speech signals may have harmonics in addition to the pitch. Some of the harmonics may be observable in the TSRF.

Clause 35. The method/device/system/software of a wireless vital sign monitoring system of clause 34, further comprising: wherein the voice-related characteristics further comprises a harmonics of the pitch of the voice activity; detecting an instantaneous harmonics based on the frequency decomposition of the TSRF in a time window associated with the current time instance.

In some embodiments, the system can identify target voice source based on beamforming. First TSCI are the raw TSCI. Second TSCI are computed based on beamforming performed on the set of raw TSCI.

Clause 36. The method/device/system/software of a wireless vital sign monitoring system of clause 30, further comprising: wherein the Type 1 device or Type 2 device has an array of antennas; obtaining a set of raw TSCI of the wireless multipath channel based on the received radio signal, each raw TSCI associated with a respective antenna; obtaining a set of directional TSCI based on a beamforming performed on the set of raw TSCI obtained based on the received radio signal associated with the array of antennas, each directional TSCI associated with a direction relative to the array of antennas, wherein the TSCI is a particular directional TSCI.

In some embodiments, the system can suppress non-target voice source based on beamforming.

Clause 37. The method/device/system/software of the wireless vital sign monitoring system of clause 36, further comprising: associating the target voice source with a component of the TSCI, wherein there is at least one non-target voice source undergoing respective asynchronous voice producing motion, wherein the wireless channel is impacted asynchronously by the respective asynchronous voice producing motion of the at least one non-target voice source; associating each non-target voice source with a different component of the TSCI or a different directional TSCI; selecting the component of the TSCI; and rejecting the at least one non-target voice source by computing the TSRF based on the selected component of the TSCI.

Clause 38. The method/device/system/software of the wireless vital sign monitoring system of clause 37, further comprising: detecting the voice activity of the target voice source based on the TSRF computed based on the TSCI; detecting another voice activity of a non-target voice source based on another TSRF computed based on another directional TSCI.

The features described above may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language (e.g., C, Java), including compiled or interpreted languages, and it may be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory may be supplemented by, or incorporated in, ASICs (application-specific integrated circuits).

While the present teaching contains many specific implementation details, these should not be construed as limitations on the scope of the present teaching or of what may be claimed, but rather as descriptions of features specific to particular embodiments of the present teaching. Certain features that are described in this specification in the context of separate embodiments may also be implemented in combination in a single embodiment. Conversely, various features that are described in the context of a single embodiment may also be implemented in multiple embodiments separately or in any suitable sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

Particular embodiments of the subject matter have been described. Any combination of the features and architectures described above is intended to be within the scope of the following claims. Other embodiments are also within the scope of the following claims. In some cases, the actions recited in the claims may be performed in a different order and still achieve desirable results. In addition, the processes depicted in the accompanying figures do not necessarily require the particular order shown, or sequential order, to achieve desirable results. In certain implementations, multitasking and parallel processing may be advantageous.

We claim:

1. A system for wireless vital sign monitoring, comprising:
   a transmitter configured to transmit a wireless signal through a wireless channel of a venue;
   a receiver configured to receive the wireless signal through the wireless channel, wherein the received wireless signal differs from the transmitted wireless signal due to the wireless channel that is impacted by a periodic motion of a vital sign of an object in the venue; and
   a processor configured for:
      obtaining a time series of channel information (CI) of the wireless channel based on the received wireless signal, wherein each CI is a vector associated with a time stamp with N components, computing a time series of denoised CI (DCI) by denoising the time series of CI (TSCI), wherein each DCI is a vector associated with a time stamp with N components, computing a time series of concatenated CI (TSCCI) based on a concatenation of the TSCI and the time series of DCI (TSDCI), wherein:

each concatenated CI (CCI) associated with a respective time stamp is a vector comprising 2N components and is computed by concatenating a respective CI associated with the same respective time stamp and a respective DCI associated with the same respective time stamp corresponding to the respective CI, a first set of N components among the 2N components are associated with the respective CI, each of the N components in the first set being associated with a respective component of the respective CI, a second set of N components among the 2N components are associated with the respective DCI, each of the N components in the second set being associated with a respective component of the respective DCI, computing a one dimensional (1D) characteristic function of CCI of the TSCCI in a sliding time window, computing a two dimensional (2D) decomposition of the TSCCI based on the 1D characteristic function in the sliding time window, enhancing the 2D decomposition based on a vertical highpass horizontal lowpass filtering, and monitoring the periodic motion of the vital sign based on the enhanced 2D decomposition.

2. The system of claim 1, wherein the processor is further configured for:

computing each CCI as a concatenation of a first basic feature of the respective CI and a second basic feature of the corresponding DCI, wherein the first basic feature of any CI comprises at least one of: the CI, a magnitude of the CI, a phase of the CI, a magnitude of a component of the CI, a phase of the component of the CI, or a function of any magnitude or phase of the CI, wherein the second basic feature of any DCI comprises at least one of: the DCI, a magnitude of the DCI, a phase of the DCI, a magnitude of a component of the DCI, a phase of the component of the DCI, or a function of any magnitude or phase of the DCI, wherein the TSDCI is computed by processing the TSCI with a first denoising filter, the first denoising filter comprising at least one of: a low-pass filter, a bandpass filter, a highpass filter, a median filter, or a percentile filter.

3. The system of claim 2, wherein the processor is further configured for:

determining a series of sliding time windows, each sliding time window being associated with a time stamp;

computing a respective one dimensional (1D) characteristic function of the CCI of the TSCCI in each sliding time window; and constructing the 2D decomposition based on the respective 1D characteristic function in each sliding time window.

4. The system of claim 3, wherein:

the respective 1D characteristic function is computed based on a transformation of the CCI of the TSCCI in each sliding time window; and the transformation comprises at least one of:

a frequency transformation, a transformation to frequency domain, a short-time Fourier transform (STFT), a wavelet transform, a filter-bank representation, a time transformation, a transformation to a time-shift domain, an auto-correlation function (ACF), an auto-covariance function, or a time-frequency decomposition.

5. The system of claim 4, wherein the processor is further configured for:

constructing a 2D matrix by lining up and aligning the 1D characteristic functions of the sliding time windows in time order according to the associated time stamps, wherein i-th column of the 2D matrix represents the 1D characteristic function associated with i-th sliding time window, j-th row of the 2D matrix is associated with a time-shift of j time units, a matrix element at the i-th column and the j-th row of the 2D matrix is a value of the 1D characteristic function in the i-th sliding time window with a time-shift of j time units, and the 2D matrix is a result of the 2D decomposition.

6. The system of claim 5, wherein the processor is further configured for:

enhancing the 2D decomposition by applying, to each matrix element of the 2D matrix, the vertical highpass horizontal lowpass filtering.

7. The system of claim 6, wherein the processor is further configured for:

filtering each matrix element of the 2D matrix with a respective 2D vertical highpass horizontal lowpass filter that is either separable or non-separable, either linear or nonlinear.

8. The system of claim 7, wherein the processor is further configured for:

enhancing the 2D decomposition by filtering each matrix element of the 2D matrix with at least one of: a respective vertical highpass filter or a respective horizontal lowpass filter, wherein each of the respective vertical highpass filter and the respective horizontal lowpass filter is either linear or nonlinear.

9. The system of claim 8, wherein the processor is further configured for enhancing the 2D decomposition by at least one of:

filtering part of each column of the 2D matrix with a respective first common vertical highpass filter;

filtering part of each row of the 2D matrix with a respective second common vertical highpass filter;

filtering part of each column of the 2D matrix with a respective first common horizontal lowpass filter; or filtering part of each row of the 2D matrix with a respective second common horizontal lowpass filter.

10. The system of claim 9, wherein:

each vertical highpass filter is a directional 1D highpass filter applied in a vertical direction or in a near-vertical direction.

11. The system of claim 10, wherein:

each horizontal lowpass filter is a directional 1D lowpass filter applied in a horizontal direction or in a near-horizontal direction.

12. The system of claim 11, wherein the processor is further configured for:

filtering each matrix element of the 2D matrix with a succession of at least two 1D filters, each being either the vertical highpass filter or the horizontal lowpass filter.

13. The system of claim 12, wherein the processor is further configured for:
enhancing the 2D decomposition by applying histogram equalization to a number of consecutive columns of the 2D matrix to generate an enhanced 2D matrix.

14. The system of claim 13, wherein the processor is further configured for:
computing a distance score based on dynamic time warping (DTW) between a reference column and a particular column of the enhanced 2D matrix associated with a particular time, wherein:
the reference column is computed in a training session by clustering a number of training columns matched based on DTW,
the training columns are computed based on training TSCI obtained from training wireless signals that are received through the wireless channel when training objects with vital signs are present and impacting the wireless channel, and
when the distance score is larger than a first threshold, the periodic motion of the vital sign of the object is tentatively not detected at the particular time.

15. The system of claim 14, wherein the processor is further configured for:
subtracting a quantity from each matrix element in the particular column of the enhanced 2D matrix; and
computing a zero-crossing count of the particular column,
wherein when the zero-crossing count is larger than a second threshold, the periodic motion of the vital sign of the object is tentatively not detected at the particular time.

16. The system of claim 15, wherein the processor is further configured for:
computing multiple peaks of the particular column of the enhanced 2D matrix; and
computing an inter-peak distance based on the multiple peaks.

17. The system of claim 16, wherein:
when the inter-peak distance is in an acceptable range, the periodic motion of the vital sign of the object is tentatively detected at the particular time, and the inter-peak distance is determined to be equal to a frequency or a period of the vital sign; and
when the inter-peak distance is not in an acceptable range, the periodic motion of the vital sign of the object is tentatively not detected at the particular time.

18. The system of claim 17, wherein the processor is further configured for:
detecting the vital sign of the object when P is larger than a third threshold, wherein P is a percentage of the periodic motion of the vital sign being tentatively detected in a period of time.

19. A wireless device of a system for wireless vital sign monitoring, comprising:
a processor;
a memory communicatively coupled to the processor; and
a receiver communicatively coupled to the processor, wherein:
an additional wireless device in the system is configured to transmit a wireless signal through a wireless channel of a venue,
the receiver is configured to receive the wireless signal through the wireless channel,
the received wireless signal differs from the transmitted wireless signal due to the wireless channel that is impacted by a periodic motion of a vital sign of an object in the venue, and
the processor is configured for:
obtaining a time series of channel information (CI) of the wireless channel based on the received wireless signal, wherein each CI is a vector associated with a time stamp with N components,
computing a time series of denoised CI (DCI) by denoising the time series of CI (TSCI), wherein each DCI is a vector associated with a time stamp with N components,
computing a time series of concatenated CI (TSCCI) based on a concatenation of the TSCI and the time series of DCI (TSDCI), wherein:
each concatenated CI (CCI) associated with a respective time stamp is a vector comprising 2N components and is computed by concatenating a respective CI associated with the same respective time stamp and a respective DCI associated with the same respective time stamp corresponding to the respective CI,
a first set of N components among the 2N components are associated with the respective CI, each of the N components in the first set being associated with a respective component of the respective CI,
a second set of N components among the 2N components are associated with the respective DCI, each of the N components in the second set being associated with a respective component of the respective DCI,
computing a one dimensional (1D) characteristic function of CCI of the TSCCI in a sliding time window,
computing a two dimensional (2D) decomposition of the TSCCI based on the 1D characteristic function in the sliding time window,
enhancing the 2D decomposition by applying a vertical highpass filter followed by a histogram equalization, and
monitoring the periodic motion of the vital sign based on the enhanced 2D decomposition.

20. A method for wireless vital sign monitoring, comprising:
transmitting a wireless signal through a wireless channel of a venue;
receiving the wireless signal through the wireless channel, wherein the received wireless signal differs from the transmitted wireless signal due to the wireless channel that is impacted by a periodic motion of a vital sign of an object in the venue;
obtaining a time series of channel information (CI) of the wireless channel based on the received wireless signal, wherein each CI is a vector associated with a time stamp with N components;
computing a time series of denoised CI (DCI) by denoising the time series of CI (TSCI), wherein each DCI is a vector associated with a time stamp with N components;
computing a time series of concatenated CI (TSCCI) based on a concatenation of the TSCI and the time series of DCI (TSDCI), wherein:
each concatenated CI (CCI) associated with a respective time stamp is a vector comprising 2N components and is computed by concatenating a respective CI associated with the same respective time stamp and a respective DCI associated with the same respective time stamp corresponding to the respective CI,
- a first set of N components among the 2N components are associated with the respective CI, each of the N components in the first set being associated with a respective component of the respective CI,
- a second set of N components among the 2N components are associated with the respective DCI, each of the N components in the second set being associated with a respective component of the respective DCI;

computing a one dimensional (1D) characteristic function of CCI of the TSCCI in a sliding time window;

computing a two dimensional (2D) decomposition of the TSCCI based on the 1D characteristic function in the sliding time window;

enhancing the 2D decomposition based on a vertical highpass filter and a histogram equalization; and monitoring the periodic motion of the vital sign based on the enhanced 2D decomposition.

* * * * *